US007601715B2

(12) United States Patent
Soundararajan et al.

(10) Patent No.: US 7,601,715 B2
(45) Date of Patent: Oct. 13, 2009

(54) PROCESS FOR PREPARING TRIAZOLE SUBSTITUTED AZAINDOLEOXOACETIC PIPERAZINE DERIVATIVES AND NOVEL SALT FORMS PRODUCED THEREIN

(75) Inventors: Nachimuthu Soundararajan, Kendall Park, NJ (US); Yuping Qiu, Glastonbury, CT (US); Wenhao Hu, Princeton, NJ (US); David R. Kronenthal, Yardley, PA (US); Pierre Sirard, St. Jean sur Richelieu (CA); Jean Lajeunesse, Candiac (CA); Robert Droghini, Candiac (CA); Ramakrishnan Chidambaram, Pennington, NJ (US); Xinhua Qian, Flemington, NJ (US); Kenneth J. Natalie, Flemington, NJ (US); Shawn K. Pack, Plainsboro, NJ (US); Nathan Reising, Evansville, IN (US); Erqing Tang, Somerset, NJ (US); Michael G. Fakes, Belle Mead, NJ (US); Qi Gao, Wallingford, CT (US); Feng Qian, Hillsborough, NJ (US); Blisse J. Vakkalagadda, North Brunswick, NJ (US); Chiajen Lai, Kendall Park, NJ (US); Shan-Ming Kuang, Florence, SC (US)

(73) Assignee: Bristol-Myers Squibb Company, Princeton, NJ (US)

( * ) Notice: Subject to any disclaimer, the term of this patent is extended or adjusted under 35 U.S.C. 154(b) by 222 days.

(21) Appl. No.: 11/455,338

(22) Filed: Jun. 19, 2006

(65) Prior Publication Data
US 2006/0293304 A1 Dec. 28, 2006

Related U.S. Application Data

(60) Provisional application No. 60/693,004, filed on Jun. 22, 2005.

(51) Int. Cl.
| | |
|---|---|
| A01N 43/58 | (2006.01) |
| A61K 31/50 | (2006.01) |
| A61K 31/497 | (2006.01) |
| C07D 239/00 | (2006.01) |
| C07D 239/02 | (2006.01) |
| C07D 241/00 | (2006.01) |
| C07D 241/02 | (2006.01) |
| C07D 295/00 | (2006.01) |

(52) U.S. Cl. .................. 514/247; 514/252.12; 544/242; 544/336; 544/358

(58) Field of Classification Search .................. None
See application file for complete search history.

(56) References Cited

U.S. PATENT DOCUMENTS

| 5,721,246 A | 2/1998 | Yoshino et al. |
| 6,476,034 B2 | 11/2002 | Wang et al. |
| 2004/0063744 A1 | 4/2004 | Wang et al. |
| 2005/0090522 A1 | 4/2005 | Wang et al. |
| 2005/0209246 A1* | 9/2005 | Ueda et al. ............. 514/253.04 |
| 2006/0100432 A1 | 5/2006 | Matiskella et al. |

FOREIGN PATENT DOCUMENTS

| EP | 0 657421 | 6/1995 |
| WO | WO 01/62255 | 8/2001 |
| WO | WO 02/062423 | 8/2002 |
| WO | WO 2004/014380 | 2/2004 |

OTHER PUBLICATIONS

J. E. Francis et al., "A convenient synthesis of 3,5-disubsituted-1,2,4-triazoles", Tetrahedron Letters vol. 28, No. 43, 1987, pp. 5133-5136.
Blair, W.S. et al., "HIV-1 entry—an expanding portal for drug discovery", Drug Discovery Today, vol. 5, No. 5, pp. 183-194 (2000).
Byrn, S.R. et al., Solid-State Chemistry of Drugs, $2^{nd}$ Ed., SSCI, Inc., publ., pp. ix-xvii (table of contents) (1999).
Hotoda, H., "Small-molecule inhibitors of HIV-1 entry via chemokine receptors", Drugs of the Future, vol. 24, No. 12, pp. 1355-1362 (1999).
Mullin, J.W. et al., "Programmed cooling of batch crystallizers", Chemical Engineering Science, vol. 26, pp. 369-377 (1971).
Sodroski, J.G. et al., "HIV-1 Entry Inhibitors in the Side Pocket", Cell, vol. 99, pp. 243-246 (1999).
Stout, G.H. et al., Chapter 3: "Symmetry Operations and Space Groups", X-ray Structure Determination, A Practical Guide, The Macmillan Company, publ., pp. 38-61 (1968).
Stout, G.H. et al., X-ray Structure Determination, A Practical Guide, The Macmillan Company, publ., pp. vii-xi (table of contents) (1968).

* cited by examiner

*Primary Examiner*—James O Wilson
*Assistant Examiner*—Noble Jarrell
(74) *Attorney, Agent, or Firm*—John F. Levis; Burton Rodney

(57) ABSTRACT

A process is provided for preparing triazole substituted azaindoleoxoacetic piperazine derivative. Novel intermediates produced in the above process, and novel N-1 and amorphous forms of a 1,2,3-triazole substituted azaindoloxoacetic piperazine derivatives and processes for producing such novel forms are also provided.

12 Claims, 5 Drawing Sheets

DSC thermogram of amorphous II/PVP (Flash Evaporation)

PXRD pattern of amorphous II/PVP (Flash Evaporation)

PXRD pattern of spray dried amorphous II/PVP-K30 (SDI)

Modulated DSC curves of amorphous II/PVP K30 prepared by spray-drying

N-1 PXRD

N-1 DSC

N-1 TGA

N-1 Moisture-Sorption Isotherms

PROCESS FOR PREPARING TRIAZOLE SUBSTITUTED AZAINDOLEOXOACETIC PIPERAZINE DERIVATIVES AND NOVEL SALT FORMS PRODUCED THEREIN

The present application takes priority from U.S. provisional application No. 60/693,004 filed Jun. 22, 2005, the disclosure of which is incorporated herein by reference.

FIELD OF THE INVENTION

The present invention relates to a process for preparing triazole substituted azaindoleoxoacetic piperazine derivatives, to novel intermediates produced therein, to novel crystalline N-1 and amorphous forms of a 1,2,3-triazole substituted azaindoleoxoacetic piperazine derivative, and to processes for producing such novel forms.

BACKGROUND OF THE INVENTION

U.S. patent application Ser. No. 10/969,675 filed Oct. 20, 2004 by Tao Wang et al., which is incorporated herein by reference, discloses substituted azaindoleoxoacetic piperazine derivatives which are antiviral agents, particularly inhibitors of HIV which have the formula

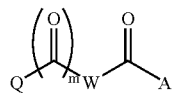

wherein:

Q is selected from the group consisting of:

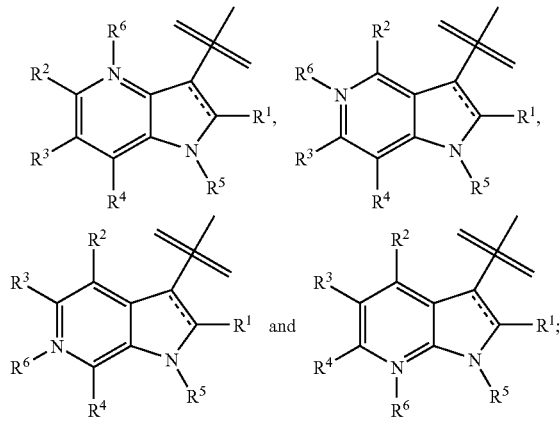

$R^1$, $R^2$, $R^3$, and $R^4$, are independently selected from the group consisting of hydrogen, halogen, cyano, nitro, $COOR^{56}$, $XR^{57}$, $C(O)R^7$, $C(O)NR^{55}R^{56}$, B, D, and E with the proviso that at least one of $R^1$-$R^4$ is selected from B or E; wherein —represents a carbon-carbon bond or does not exist;

m is 1 or 2;

$R^5$ is hydrogen or $(CH_2)_nCH_3$, $-C(O)(CH_2)_nCH_3$, $-C(O)O(CH_2)_nCH_3$, $-C(O)(CH_2)_nN(CH_3)_2$ wherein n is 0-5;

$R^6$ is O or does not exist;

A is selected from the group consisting of $C_{1-6}$alkoxy, aryl and heteroaryl; in which said aryl is phenyl or naphthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, $-C(O)NH_2$, $C_{1-6}$alkyl, $-NHC(O)CH_3$, halogen and trifluoromethyl;

—W— is

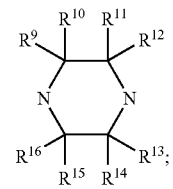

B is selected from the group consisting of $-C(=NR^{46})(R^{47})$, $C(O)NR^{40}R^{41}$, aryl, heteroaryl, heteroalicyclic, $S(O)_2R^8$, $C(O)R^7$, $XR^{8a}$, $(C_{1-6})$alkyl$NR^{40}R^{41}$, $(C_{1-6})$alkyl$COOR^{8b}$; wherein said aryl, heteroaryl, and heteroalicyclic are optionally substituted with one to thee same or different halogens or from one to thee same or different substituents selected from the group F; wherein aryl is naphthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

q is 0, 1, or 2;

D is selected from the group consisting of $(C_{1-6})$alkyl and $(C_{2-6})$alkenyl; wherein said $(C_{1-6})$alkyl and $(C_{2-6})$alkenyl are optionally substituted with one to thee same or different halogens or from one to thee same or different substituents selected from the group consisting of $C(O)NR^{55}R^{56}$, hydroxy, cyano and $XR^{57}$;

E is selected from the group consisting of $(C_{1-6})$alkyl and $(C_{2-6})$alkenyl; wherein said $(C_{1-6})$alkyl and $(C_{2-6})$alkenyl are independently optionally substituted with a member selected from the group consisting of phenyl, heteroaryl, SMe, SPh, $-C(O)NR_{56}R_{57}$, $C(O)R_{57}$, $SO_2(C_{1-6})$alkyl and $SO_2Ph$; wherein heteroaryl is a monocyclic system which contains from 3 to 7 ring atoms, including from 1 to 4 heteroatoms;

F is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, $-C(O)R^{57}$, benzyl, $-NR^{42}C(O)-(C_{1-6})$alkyl, $-NR^{42}C(O)-(C_{3-6})$cycloalkyl, $-NR^{42}C(O)$-aryl, $-NR^{42}C(O)$-heteroaryl, $-NR^{42}C(O)$-heteroalicyclic, a 4, 5, or 6 membered ring cyclic N-lactam, $-NR^{42}S(O)_2-(C_{1-6})$alkyl, $-NR^{42}S(O)_2-(C_{3-6})$cycloalkyl, $-NR^{42}S(O)$2-aryl, $-NR^{42}S(O)_2$-heteroaryl, $-NR^{42}S(O)_2$-heteroalicyclic, $S(O)_2(C_{1-6})$alkyl, $S(O)_2$aryl, $-S(O)2NR^{42}R^{43}$, $NR^{42}R^{43}$, $(C_{1-6})$alkyl$C(O)NR^{42}R^{43}$, $C(O)NR^{42}R^{43}$, $NHC(O)NR^{42}R^{43}$, $OC(O)NR^{42}R^{43}$, $NHC(O)OR^{54}$, $(C_{1-6})$alkyl$NR^{42}R^{43}$, $COOR^{54}$, and $(C_{1-6})$alkyl$COOR^{54}$; wherein said $(C_{1-6})$alkyl, $(C_{3-7})$cycloalkyl, aryl, heteroaryl, heteroalicyclic, $(C_{1-6})$alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, cyano, halogen, nitro, —C(O)R$^{57}$, benzyl, —NR$^{48}$C(O)—$(C_{1-6})$alkyl, —NR$^{48}$C(O)—$(C_{3-6})$cycloalkyl, —NR$^{48}$C(O)-aryl, —NR$^{48}$C(O)-heteroaryl, —NR$^{48}$C(O)-heteroalicyclic, a 4, 5, or 6 membered ring cyclic N-lactam, —NR$^{48}$S(O)$_2$—$(C_{1-6})$alkyl, —NR$^{48}$S(O)$_2$—$(C_{3-6})$cycloalkyl, —NR$^{48}$S(O)$_2$-aryl, —NR$^{48}$S(O)$_2$-heteroaryl, —NR$^{48}$S(O)$_2$-heteroalicyclic, sulfinyl, sulfonyl, sulfonamide, NR$^{48}$R$^{49}$, $(C_{1-6})$alkyl C(O)NR$^{48}$R$^{49}$, C(O)NR$^{48}$R$^{49}$, NHC(O)NR$^{48}$R$^{49}$, OC(O)NR$^{48}$R$^{49}$, NHC(O)OR$^{54'}$, $(C_{1-6})$alkylNR$^{48}$R$^{49}$, COOR$^{54}$, and $(C_{1-6})$alkylCOOR$^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

R$^7$ is selected from the group consisting of aryl, heteroaryl, and heteroalicyclic; wherein said aryl, heteroaryl, and heteroalicyclic are optionally substituted with one to thee same or different halogens or with from one to thee same or different substituents selected from the group F; wherein for R$^7$, R$^8$, R$^{8a}$, R$^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

R$^8$ is selected from the group consisting of hydrogen, $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F;

R$^{8a}$ is a member selected from the group consisting of aryl, heteroaryl, and heteroalicyclic; wherein each member is independently optionally substituted with one to six same or different halogens or from one to five same or different substituents selected from the group F;

R$^{8b}$ is selected from the group consisting of hydrogen, $(C_{1-6})$alkyl and phenyl;

R$^9$, R$^{10}$, R$^{11}$, R$^{12}$, R$^{13}$, R$^{14}$, R$^{15}$, R$^{16}$, are each independently selected from the group consisting of hydrogen and $(C_{1-6})$alkyl; wherein said $(C_{1-6})$alkyl is optionally substituted with one to thee same or different halogens;

X is selected from the group consisting of NH or NCH$_3$, O, and S;

R$^{40}$ and R$^{41}$ are independently selected from the group consisting of (a) hydrogen;

(b) $(C_{1-6})$alkyl or $(C_{3-7})$cycloalkyl substituted with one to thee same or different halogens or from one to two same or different substituents selected from the group F; and (c) $(C_{1-6})$alkoxy, aryl, heteroaryl or heteroalicyclic; or R$^{40}$ and R$^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to thee same or different halogens or from one to two same or different substituents selected from the group F; wherein for R$^{40}$ and R$^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is C(O)NR$^{40}$R$^{41}$, at least one of R$^{40}$ and R$^{41}$ is not selected from groups (a) or (b);

R$^{42}$ and R$^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or R$^{42}$ and R$^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to thee same or different halogens or from one to two same or different substituents selected from the group G; wherein for R$^{42}$ and R$^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

R$_a$ and R$_b$ are each independently H, $(C_{1-6})$alkyl or phenyl;

R$^{46}$ is selected from the group consisting of H, OR$^{57}$, and NR$^{55}$R$^{56}$;

R$^{47}$ is selected from the group consisting of H, amino, halogen, phenyl, and $(C_{1-6})$alkyl;

R$^{48}$ and R$^{49}$ are independently selected from the group consisting of hydrogen, $(C_{1-6})$alkyl and phenyl;

R$^{50}$ is selected from the group consisting of H, $(C_{1-6})$alkyl, $(C_{3-6})$cycloalkyl, and benzyl; wherein each of said $(C_{1-6})$alkyl, $(C_{3-7})$cycloalkyl and benzyl are optionally substituted with one to thee same or different halogen, amino, OH, CN or NO$_2$;

R$^{54}$ is selected from the group consisting of hydrogen and $(C_{1-6})$alkyl;

R$^{54'}$ is $(C_{1-6})$alkyl;

R$^{55}$ and R$^{56}$ are independently selected from the group consisting of hydrogen and $(C_{1-6})$alkyl; and R$^{57}$ is selected from the group consisting of hydrogen, $(C_{1-6})$alkyl and phenyl.

Among the over 350 compounds disclosed in application Ser. No. 10/969,675 are the 1,2,4-triazole derivative of the structure

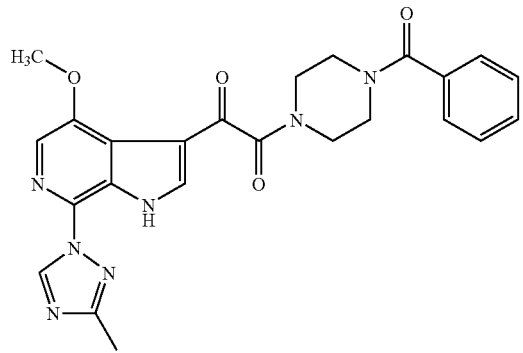

(hereinafter Compound I,
or 1,2,4-triazole derivative I
or 1,2,4-triazole compound I) disclosed in Example 316,
and the 1,2,3-triazole derivative of the structure

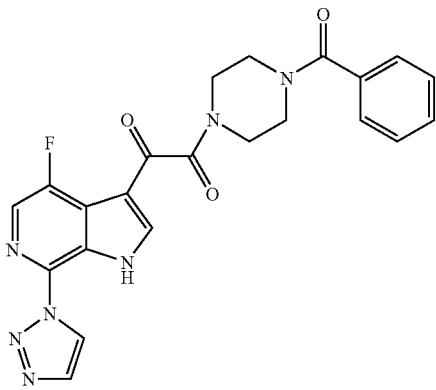

(hereinafter Compound II,
or 1,2,3-triazole derivative II
or 1,2,3-triazole compound II) disclosed in Example 216.

BRIEF DESCRIPTION OF THE INVENTION

In accordance with the present invention, compounds are provided which are intermediates for use in the preparation of azaindoleoxoacetic piperazine antiviral agents X as disclosed in U.S. application Ser. No. 10/969,675. The intermediate compounds of the invention have the following structures:

A

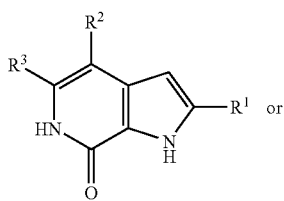

or

Aa

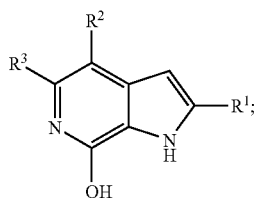

B

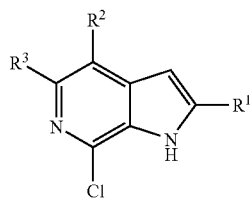

or its HCl salt;

C

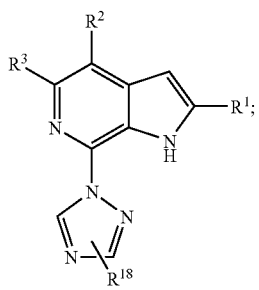

D

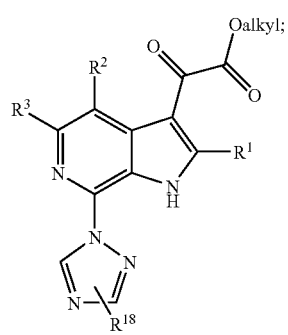

F

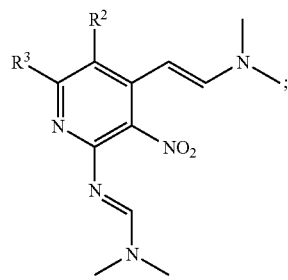

Fa

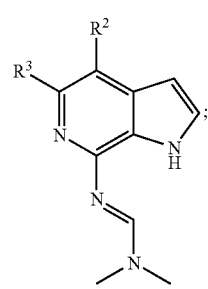

G

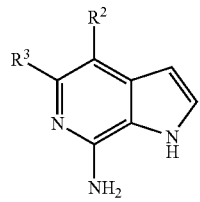

(or its HCl salt);

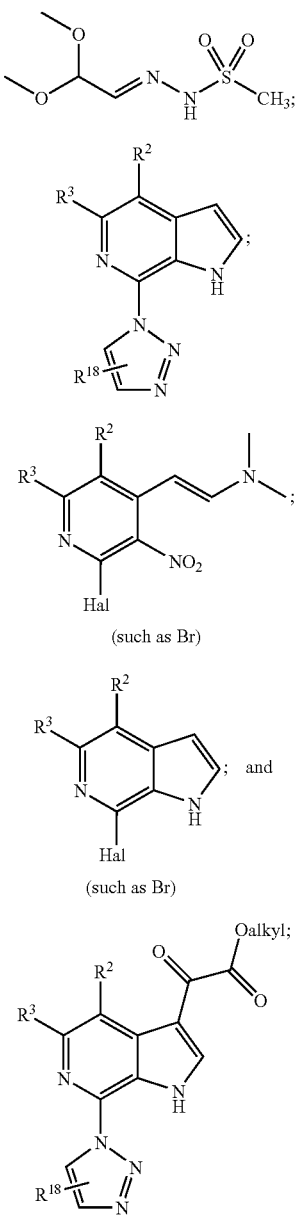

wherein R[18] is H or alkyl; Hal is a halogen; R[1], R[2] and R[3] are independently selected from the group consisting of hydrogen, halogen, cyano, nitro, COOR[56], XR[57], C(O)R[7], C(O)NR[55]R[56], B, D, and E;

B is selected from the group consisting of —C(=NR[46])(R[47]), C(O)NR[40]R[41], aryl, heteroaryl, heteroalicyclic, S(O)$_2$R[8], C(O)R[7], XR[8a], (C$_{1-6}$)alkylNR[40]R[41], (C$_{1-6}$)alkylCOOR[8b]; wherein said aryl, heteroaryl, and heteroalicyclic are optionally substituted with one to thee same or different halogens or from one to thee same or different substituents selected from the group F; wherein aryl is naphthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

D is selected from the group consisting of (C$_{1-6}$)alkyl and (C$_{2-6}$)alkenyl; wherein said (C$_{1-6}$)alkyl and (C$_{2-6}$)alkenyl are optionally substituted with one to thee same or different halogens or from one to thee same or different substituents selected from the group consisting of C(O)NR[55]R[56], hydroxy, cyano and XR[57];

E is selected from the group consisting of (C$_{1-6}$)alkyl and (C$_{2-6}$)alkenyl; wherein said (C$_{1-6}$)alkyl and (C$_{2-6}$)alkenyl are independently optionally substituted with a member selected from the group consisting of phenyl, heteroaryl, SMe, SPh, —C(O)NR[56]R[57], C(O)R[57], SO$_2$(C$_{1-6}$)alkyl and SO$_2$Ph; wherein heteroaryl is a monocyclic system which contains from 3 to 7 ring atoms, including from 1 to 4 heteroatoms;

F is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, (C$_{1-6}$)thioalkoxy, cyano, halogen, nitro, —C(O)R[57], benzyl, —NR[42]C(O)—(C$_{1-6}$)alkyl, —NR[42]C(O)—(C$_{3-6}$)cycloalkyl, —NR[42]C(O)-aryl, —NR[42]C(O)-heteroaryl, —NR[42]C(O)-heteroalicyclic, a 4, 5, or 6 membered ring cyclic N-lactam, —NR[42]S(O)$_2$—(C$_{1-6}$)alkyl, —NR[42]S(O)$_2$—(C$_{3-6}$)cycloalkyl, —NR[42]S(O)$_2$-aryl, —NR[42]S(O)$_2$-heteroaryl, —NR[42]S(O)$_2$-heteroalicyclic, S(O)$_2$(C$_{1-6}$)alkyl, S(O)$_2$aryl, —S(O)$_2$NR[42]R[43], N[42]R[43], (C$_{1-6}$)alkylC(O)NR[42]R[43], C(O)NR[42]R[43], NHC(O)NR[42]R[43], OC(O)NR[42]R[43], NHC(O)OR[54], (C$_{1-6}$)alkylNR[42]R[43], COOR[54], and (C$_{1-6}$)alkylCOOR[54]; wherein said (C$_{1-6}$)alkyl, (C$_{3-7}$)cycloalkyl, aryl, heteroaryl, heteroalicyclic, (C$_{1-6}$)alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, cyano, halogen, nitro, —C(O)R[57], benzyl, —NR[48]C(O)—(C$_{1-6}$)alkyl, —NR[48]C(O)—(C$_{3-6}$)cycloalkyl, —NR[48]C(O)-aryl, —NR[48]C(O)-heteroaryl, —NR[48]C(O)-heteroalicyclic, a 4, 5, or 6 membered ring cyclic N-lactam, —NR[48]S(O)$_2$—(C$_{1-6}$)alkyl, —NR[48]S(O)$_2$—(C$_{3-6}$)cycloalkyl, —NR[48]S(O)$_2$-aryl, —NR[48]S(O)$_2$-heteroaryl, —NR[48]S(O)$_2$-heteroalicyclic, sulfinyl, sulfonyl, sulfonamide, NR[48]R[49], (C$_{1-6}$)alkyl C(O)NR[48]R[49], C(O)NR[48]R[49], NHC(O)NR[48]R[49], OC(O)NR[48]R[49], NHC(O)OR[54'], (C$_{1-6}$)alkylNR[48]R[49], COOR[54], and (C$_{1-6}$)alkylCOOR[54]; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

R[7] is selected from the group consisting of aryl, heteroaryl, and heteroalicyclic; wherein said aryl, heteroaryl, and heteroalicyclic are optionally substituted with one to thee same or different halogens or with from one to thee same or different substituents selected from the group F;

wherein for R[7], R[8], R[8a], R[8b] aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

$R^8$ is selected from the group consisting of hydrogen, $(C_{1-6})$alkyl, $(C_{3-7})$cycloalkyl, $(C_{2-6})$alkenyl, $(C_{3-7})$ cycloalkenyl, $(C_{2-6})$alkynyl, aryl, heteroaryl, and heteroalicyclic; wherein said $(C_{1-6})$alkyl, $(C_{3-7})$cycloalkyl, $(C_{2-6})$alkenyl, $(C_{3-7})$cycloalkenyl, $(C_{2-6})$alkynyl, aryl, heteroaryl, and heteroalicyclic are optionally substituted with one to six same or different halogens or from one to five same or different substituents selected from the group F;

$R^{8a}$ is a member selected from the group consisting of aryl, heteroaryl, and heteroalicyclic; wherein each member is independently optionally substituted with one to six same or different halogens or from one to five same or different substituents selected from the group F;

$R^{8b}$ is selected from the group consisting of hydrogen, $(C_{1-6})$alkyl and phenyl;

$R^{40}$ and $R^{41}$ are independently selected from the group consisting of (a) hydrogen;

(b) $(C_{1-6})$alkyl or $(C_{3-7})$cycloalkyl substituted with one to thee same or different halogens or from one to two same or different substituents selected from the group F; and (c) $(C_{1-6})$alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to thee same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is $C(O)NR^{40}R^{41}$, at least one of $R^{40}$ and $R^{41}$ is not selected from groups (a) or (b);

$R^{42}$ and $R^{43}$ are independently selected from the group consisting of hydrogen, $(C_{1-6})$alkyl, allyl, $(C_{1-6})$alkoxy, $(C_{3-7})$cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said $(C_{1-6})$alkyl, $(C_{1-6})$alkoxy, $(C_{3-7})$cycloalkyl, aryl, heteroaryl, and heteroalicyclic are optionally substituted with one to thee same or different halogens or from one to two same or different substituents selected from the group G; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

$R^{46}$ is selected from the group consisting of H, $OR^{57}$, and $NR^{55}R^{56}$;

$R^{47}$ is selected from the group consisting of H, amino, halogen, phenyl, and $(C_{1-6})$alkyl;

$R^{48}$ and $R^{49}$ are independently selected from the group consisting of hydrogen, $(C_{1-6})$alkyl and phenyl;

$R^{54}$ is selected from the group consisting of hydrogen and $(C_{1-6})$alkyl;

$R^{56}$ is independently selected from the group consisting of hydrogen and $(C_{1-6})$alkyl; and $R^{57}$ is selected from the group consisting of hydrogen, $(C_{1-6})$alkyl and phenyl.

Preferred intermediates of the invention have the following structures:

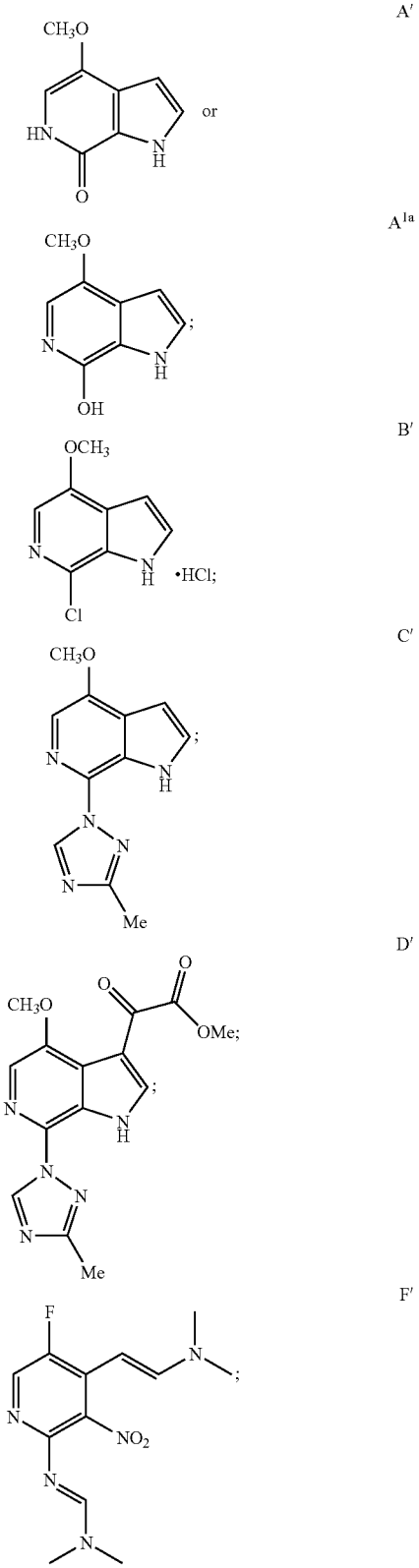

-continued

F'

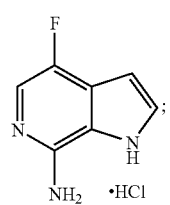
G'

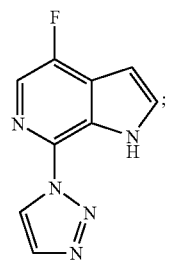
H'

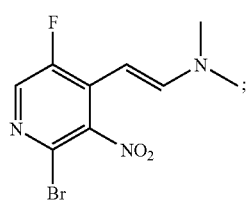
J'

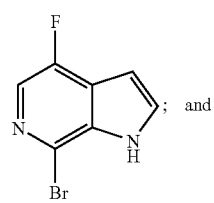
K'

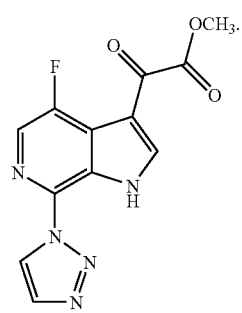
L'

In accordance with the present invention, a process is provided for preparing compound A or A$^a$ having the structure

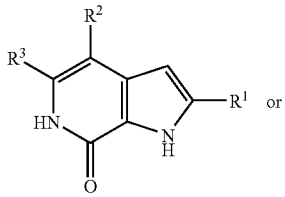
F$^c$
A
or
A$^a$ wherein R$^1$, R$^2$ and R$^3$ are as defined above, which includes the step of selectively hydrolyzing a compound of the structure a.

a or an acid salt thereof, such as the HCl salt to form compound A or A$^a$.

The selective hydrolysis step described above is preferably carried out by treating compound a with 1-methyl-2-pyrrolidinone (NMP) and water, and heating at a temperature within the range from about 80 to about 100° C., preferably from about 85 to about 90° C.

In accordance with the present invention, a process is provided for preparing compound B having the structure

B wherein R$^1$, R$^2$ and R$^3$ are as defined above, which includes the step of reacting compound A of the structure

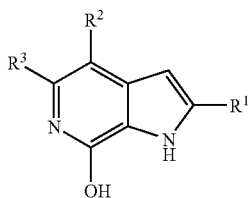

A<sup>1a</sup> with a chlorinating agent to form compound B.

In a preferred embodiment of the above process, compound A is reacted with POCl$_3$ under an inert atmosphere at a temperature within the range from about 85 to about 105° C., preferably from about 93 to about 97° C.

In accordance with the present invention, a process is provided for preparing compound C having the structure

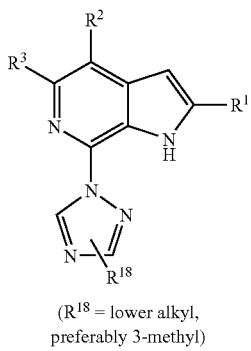

C ($R^{18}$ = lower alkyl, preferably 3-methyl)

wherein $R^1$, $R^2$ and $R^3$ are as defined above, which includes the step of reacting compound B

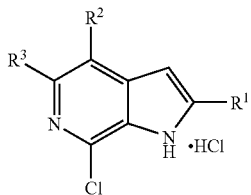

B with 3-methyl-1,2,4-triazole Y

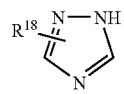

Y ($R^{18}$ is lower alkyl, preferably 3-methyl)

to form compound C. The above reaction is carried out at a temperature within the range from about 120 to about 150° C., preferably from about 140 to about 145° C.

In addition, in accordance with the present invention, a process is provided for preparing compound D having the structure

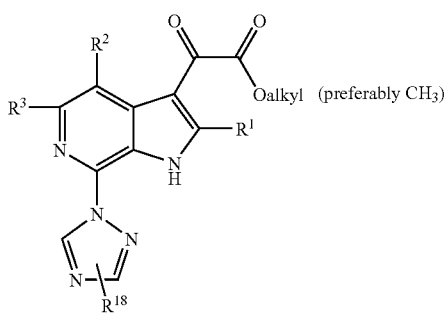

D wherein $R^1$, $R^2$ and $R^3$ are as defined above, which includes the step of subjecting compound C of the structure

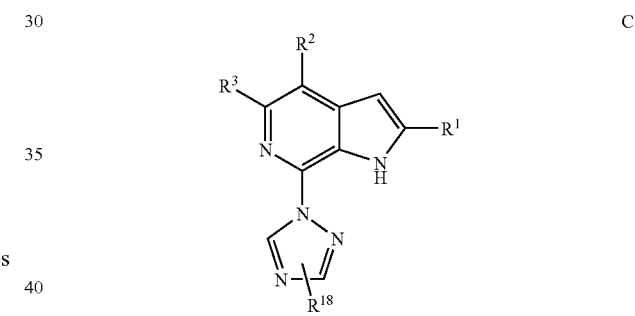

C to a Grignard acylation reaction wherein acid chloride 1

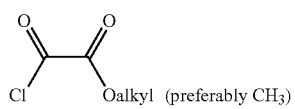

1 is reacted with compound C to form compound D.

The Grignard acylation reaction is carried out in the presence of a Grignard reagent, preferably RCH$_2$MgHal wherein R is lower alkyl and Hal is Cl or Br, preferably C$_2$H$_5$MgCl, in an organic solvent, such as THF and 2-CH$_3$THF and organic base, such as pyridine, at a temperature within the range from about −50 to about −25° C., preferably from about −50 to about −40° C.

In accordance with the present invention, there is also provided a process for preparing compound IA having the structure

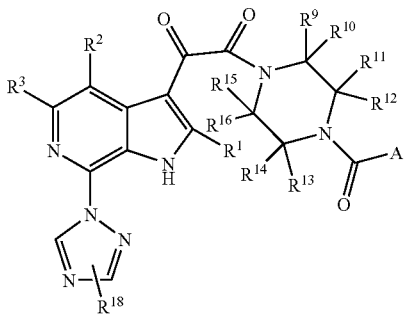

(R[18] is preferably CH$_3$ and
A is preferably phenyl)

wherein R[1], R[2] and R[3] are as defined above, R[18] is H or (C$_{1-6}$)alkyl and R[9], R[10], R[11], R[12], R[13], R[14], R[15] and R[16] are each independently selected from H and (C$_{1-6}$)alkyl which may optionally be substituted with 1, 2 or 3 same or different halogen, which includes the step of preparing compound D having the structure

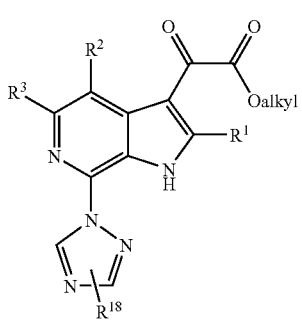

as described above, and reacting compound D with a compound of the structure

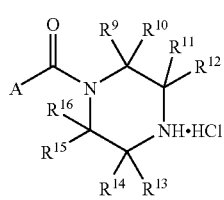

in the presence of an organometallic base to form compound IA;

A is selected from C$_{1-6}$alkoxy, aryl and heteroaryl; in which aryl is phenyl or naphthyl; the heteroaryl is selected from pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and aryl or heteroaryl is optionally substituted with one or two of the same or different members selected from amino, nitro, cyano, hydroxy, C$_{1-6}$alkoxy, —C(O)NH$_2$, C$_{1-6}$alkyl, —NHC(O)CH$_3$, halogen and trifluoromethyl;

A is preferably aryl and more preferably phenyl; and

R[9], R[10], R[11], R[12], R[13], R[14], R[15] and R[16] are as defined above and each is preferably H.

The above reaction is carried out at a temperature within the range from about −10 to about 30° C., preferably from about 5 to about 25° C. Regarding the processes for preparing compounds A, B, C, and D and IA, in such compounds R[1] is preferably H, R[3] is preferably H, and R[2] is preferably alkoxy, more preferably methoxy.

In another aspect of the present invention, a process is provided for preparing compound F having the structure

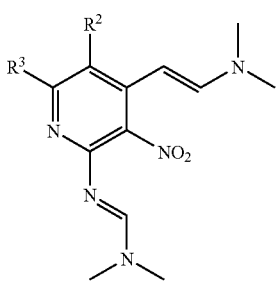

wherein R[2] and R[3] are as defined above, which includes the step of reacting a compound of the structure b.

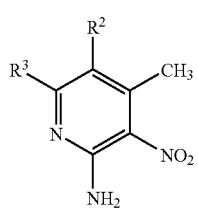

with a compound of the structure

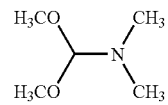

to form compound F.

The above reaction is carried out at a temperature within the range from about 80° C. to about 150° C., preferably from about 120° C. to about 130° C.

In still another aspect of the present invention, a process is provided for preparing compound G having the structure

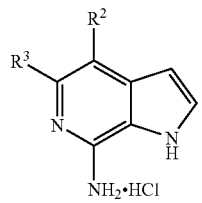

where $R^1$, $R^2$ and $R^3$ are as defined above, which includes the step of reducing compound F of the structure

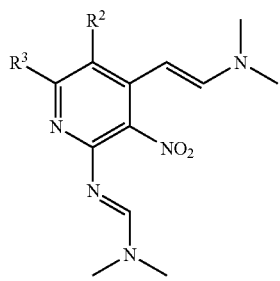

to form compound $F^a$ of the structure

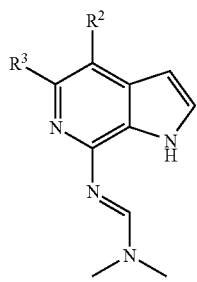

and hydrolyzing compound $F^a$ to form compound G, wherein the reduction is carried out by reacting compound F with hydrogen in the presence of a hydrogenation catalyst, preferably platinum on carbon, and the hydrolysis is carried out by reacting compound $F^a$ with an acid such as hydrochloric acid at a temperature within the range from about 65 to about 85° C., preferably from about 78 to about 82° C.

In addition, in accordance with the present invention, a process is provided for preparing compound H having the structure

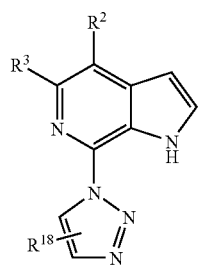

where $R^1$, $R^2$, $R^3$ and $R^{18}$ are as defined above. The process of the invention involves elaboration of amine G to triazole H and includes the step of option a) treating compound G of the structure

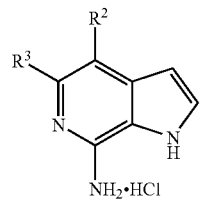

with a compound of the structure $G^a$

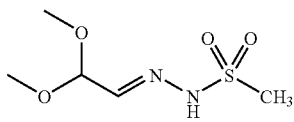

and potassium phosphate $K_3PO_4$; or (alternatively, the free amine of G and $K_2HPO_4$)

option b) treating compound G with methylsulfonyl hydrazide

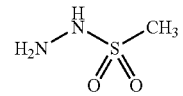

and 2,2-dimethoxyacetaldehyde

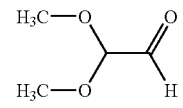

(to form compound $G^a$ in situ), and $K_3PO_4$ to form compound H.

In option a), the reaction is carried out at a temperature within the range from about 60° C. to about 120° C., preferably from about 80° C. to about 100° C.

In option b), the reaction is carried out at a temperature within the range from about 60 to about 100° C., preferably from about 65 to about 75° C.

In a preferred embodiment, option a) and option b) are each carried out in the presence of an organic solvents such as acetonitrile/dimethylformamide/ethylacetate.

In a further aspect of the present invention, a process is provided for preparing compound K having the structure

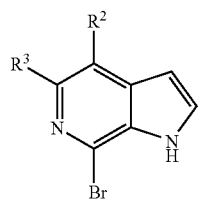

wherein $R^1$, $R^2$ and $R^3$ are as defined above, which includes the step of reducing compound J of the structure

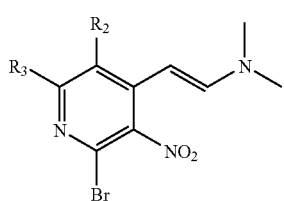

to form compound K, wherein the reduction is carried out by reacting compound J with hydrogen in the presence of a hydrogenation catalyst, preferably platinum or carbon (Escat 261), employing a temperature within the range from about 25 to about 45° C., preferably from about 30 to about 35° C.

In another aspect of the present invention, a process is provided for preparing compound J having the structure

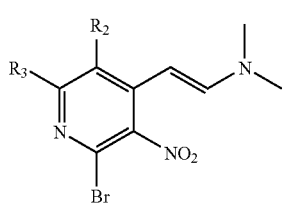

wherein $R^2$ and $R^3$ are as defined above, which includes the step of reacting a compound of the structure d.

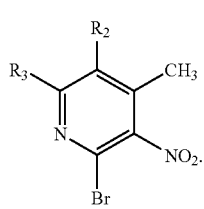

with a compound of the structure

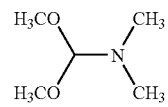

in the presence of an organometallic base, preferably lithium methoxide, to form compound J.

The above reaction is carried out at a temperature within the range from about 70 to about 90° C., preferably from about 80 to about 85° C.

In a further aspect of the present invention, a process is provided for preparing compound H

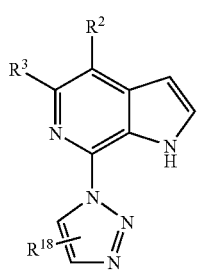

(where $R^{18}$ is preferably H)

wherein $R^1$, $R^2$, $R^3$ and $R^{18}$ are as defined above, which includes the step of reacting compound K having the structure

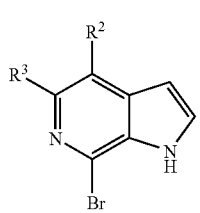

with a 1,2,3-triazole of the structure

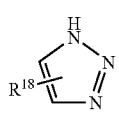

in the presence of an inorganic base like $K_2HPO_4$ or $NaHPO_4$, preferably $K_2HPO_4$, and a copper catalyst like CuO, $Cu_2I_2$, $CuI_2$, $Cu_2O$ (preferably $K_2HPO_4$ and $Cu_2O$) to form compound H.

The reaction is carried out at a temperature within the range from about 100 to about 160° C., preferably from about 130 to about 150° C.

In another aspect of the present invention, a process is provided for preparing compound L having the structure

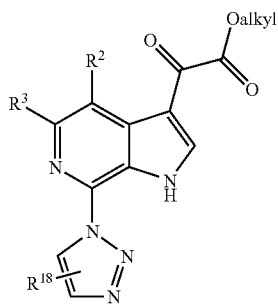

L which includes the step of subjecting compound H of the structure

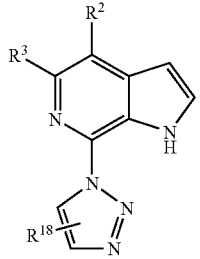

H to a Grignard acylation reaction where acid chloride 1

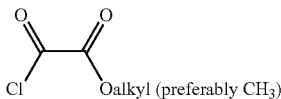

1 is reacted with compound H to form compound L.

The Grignard acylation reaction is carried out in the presence of a Grignard reagent ($RCH_2MgHal$ where R is lower alkyl and Hal is Cl or Br, preferably $C_2H_5MgCl$, in an organic solvent, such as THF, and $2$-$CH_3THF$, or toluene and $CH_2Cl_2$, and organic base such as pyridine, at a temperature within the range from about −50 to about 25° C., preferably from about −40 to about −50° C.

In addition, in accordance with the present invention, a process is provided for preparing compound IIA having the structure

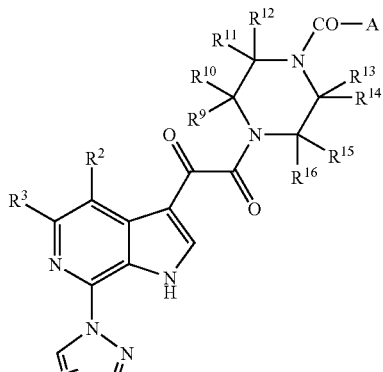

IIA ($R^{18}$ is preferably H and A is preferably phenyl)

wherein $R^2$, $R^3$, $R^9$ to $R^{16}$, $R^{18}$ and A are as defined above, which includes the step of preparing compound L of the structure

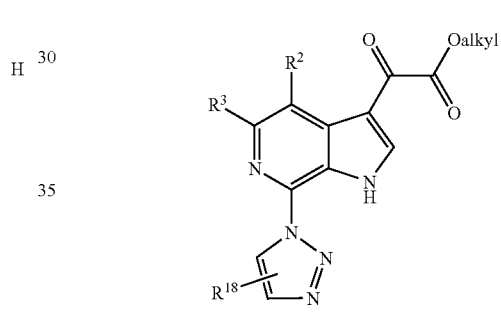

L as described above, and reacting compound L with a compound $D^a$ of the structure

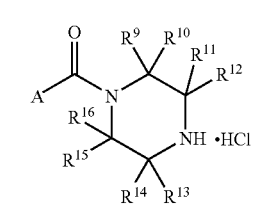

$D^a$ in the presence of an organometallic base to form compound IIA.

The above reaction is carried out at a temperature within the range from about −20 to about 50° C., preferably from about −5 to about 5° C.

Regarding the processes for preparing Compounds J, K, H, L, F, $F^a$, and G and IA and IIA, $R^1$ is preferably H, $R^3$ is preferably H and $R^2$ is halogen such as F, $R^9$ to $R^{16}$ are each H and A is phenyl.

In addition, in accordance with the present invention, the N-1 crystalline form of the 1,2,3-triazole derivative II is provided, whose crystal structure is established by single crystal analysis (Tables 1 and 2) and the bulk properties are characterized by powder X-ray diffraction (PXRD, FIG. 5), differential scanning calorimetry (DSC, FIG. 6), thermogravimetric analysis (TGA, FIG. 7), as will be described in detail hereinafter. Other techniques such as solid state nuclear magnetc resonance (SSNMR), IR, Fourier Transform-IR (FT-IR), and Raman spectroscopy.

Also, in accordance with the present invention, a stabilized amorphous form of the 1,2,3-triazole derivative II is also provided.

Still further in accordance with the present invention, a process is provided for preparing the N-1 crystalline form of the 1,2,3-triazole derivative II, which includes the step of recrystallizing or slurrying the 1,2,3-triazole derivative II in a suitable solvent, such as a mixture of ethanol and water, or other solvents such as aqueous acetonitrile or acetonitrile and methanol, or mixtures of solvents containing dichloromethane, methanol, ethanol, isopropyl alcohol and/or acetonitrile.

Another embodiment of the invention is a pharmaceutical formulation containing an antiviral effective amount of the crystalline N-1 form or any solubilized form thereof, or the stabilized amorphous form of the 1,2,3-triazole derivative II, including pharmaceutically acceptable salts thereof and a pharmaceutically acceptable carrier. When used for treating HIV infection, this formulation can optionally additionally contain an antiviral effective amount of an AIDS treatment agent selected from the group consisting of: an AIDS antiviral agent; an antiinfective agent; an immunomodulator; and HIV entry inhibitors.

Yet another embodiment of the invention is a method for treating mammals, including humans, infected with a virus, such as HIV, comprising administering to said mammal an antiviral effective amount of the N-1 form or any solubilized form thereof, or the stabilized amorphous form of the 1,2,3-triazole derivative II, including pharmaceutically acceptable salts thereof, a pharmaceutically acceptable carrier, optionally in combination with an antiviral effective amount of an AIDS treatment agent selected from the group consisting of: (a) an AIDS antiviral agent; (b) an anti-infective agent; (c) an immunomodulator; and (d) HIV entry inhibitors.

The N-1 form and the stabilized amorphous form of the 1,2,3-triazole derivative II according to the invention may be characterized using various techniques, the operation of which are well known to those of ordinary skill in the art. The forms may be characterized and distinguished using single crystal X-ray diffraction, which is based on unit cell measurements of a single crystal of a form at a fixed analytical temperature. A detailed description of unit cells is provided in Stout & Jensen, X-Ray Structure Determination: A Practical Guide, Macmillan Co., New York (1968), Chapter 3, which is herein incorporated by reference. Alternatively, the unique arrangement of atoms in spatial relation within the crystalline lattice may be characterized according to the observed fractional atomic coordinates. Another means of characterizing the crystalline structure is by powder X-ray diffraction analysis in which the experimental or observed diffraction profile is compared to that of pure powder material or to a simulated profile obtained from single crystal X-ray determination.

Other means of characterizing the form may be used, such as solid state nuclear magnetic resonance (SSNMR), IR, FT-IR, Raman, differential scanning calorimetry, thermogravimetric analysis and moisture-sorption isotherms. These parameters may also be used in combination to characterize the subject form.

In another aspect of the present invention, a stabilized amorphous form of the 1,2,3-triazole derivative II prepared by flash evaporation of a solution of Form N-1 of the 1,2,3-triazole derivative II in a suitable solvent may be characterized by a differential scanning calorimetry (DSC) thermogram substantially as shown in FIG. 1.

In a different aspect of the present invention, a stabilized amorphous form of the 1,2,3-triazole derivative II prepared by flash evaporation of a solution of Form N-1 of the 1,2,3-triazole derivative II in a suitable solvent may be characterized by an observed powder X-ray diffraction (PXRD) pattern substantially as shown in FIG. 2.

In another aspect of the present invention, a stabilized amorphous form of the 1,2,3-triazole derivative II prepared by spray drying of a solution of Form N-1 of the 1,2,3-triazole derivative II in a suitable solvent may be characterized by the powder X-ray diffraction pattern substantially as shown in FIG. 3.

In yet another aspect of the present invention, a stabilized amorphous form of the 1,2,3-triazole derivative II prepared by spray drying of a solution of Form N-1 of the 1,2,3-triazole derivative II in a suitable solvent may be characterized by the modulated differential scanning calorimetry thermogram (open pan) substantially as shown in FIG. 4a.

In still another aspect of the present invention, a stabilized amorphous form of the 1,2,3-triazole derivative II prepared by spray drying of a solution of Form N-1 of the 1,2,3-triazole derivative II in a suitable solvent may be characterized by the modulated differential scanning calorimetry thermogram (sealed pan) substantially as shown in FIG. 4b.

In another aspect of the present invention, crystalline Form N-1 of the 1,2,3-triazole derivative II may be characterized by unit cell parameters substantially equal to the following:

Cell Dimensions:
   a=39.2481(14)Å
   b=5.5577(2)Å
   c=21.8072(10)Å
   α=90°
   β=122.399(4)°
   γ=90°
   Space group C2/c wherein the crystalline form is at about 25° C. and the single crystal data shown in Table 1.

In a different aspect of the present invention, crystalline Form N-1 of the 1,2,3-triazole derivative II may be characterized by fractional atomic coordinates substantially as listed in Table 2.

In a different aspect of the present invention, crystalline Form N-1 of the 1,2,3-triazole derivative II may be characterized by simulated and observed powder X-ray diffraction patterns substantially as shown in FIG. 5.

In a different aspect of the present invention, crystalline Form N-1 of the 1,2,3-triazole derivative II may be characterized by a powder X-ray diffraction PXRD pattern having the following 2θ values (CuKα λ=1.5418 Å) 5.3±0.1, 8.1±0.1, 9.6±0.1, 16.2±0.1, 17.0±0.1, 19.6±0.1, 20.7±0.1, and 23.0±0.1.

In a different aspect of the present invention, crystalline Form N-1 of the 1,2,3-triazole derivative II may be characterized by a differential scanning calorimetry (DSC) thermogram (open pan) substantially as shown in FIG. 6 having endotherm onset at about 279° C.

In another aspect of the present invention, crystalline Form N-1 of the 1,2,3-triazole derivative II may be characterized by a thermal gravimetric analysis (TGA) curve (open pan) having a negligible weight loss up to about 100° C. substantially as shown in FIG. 7.

In a different aspect of the present invention, crystalline Form N-1 of the 1,2,3-triazole derivative II may be characterized by the moisture-sorption isotherm substantially as shown in FIG. 8 which shows about 0.1% weight gain in the range from about 25 to about 75% RH @ 25° C.

The various crystalline forms of the 1,2,4-triazole derivative I are disclosed in U.S. provisional application No. 60/626,148 filed Nov. 9, 2004, the disclosure of which is incorporated herein by reference.

DETAILED DESCRIPTION OF THE INVENTION

Figure 1:
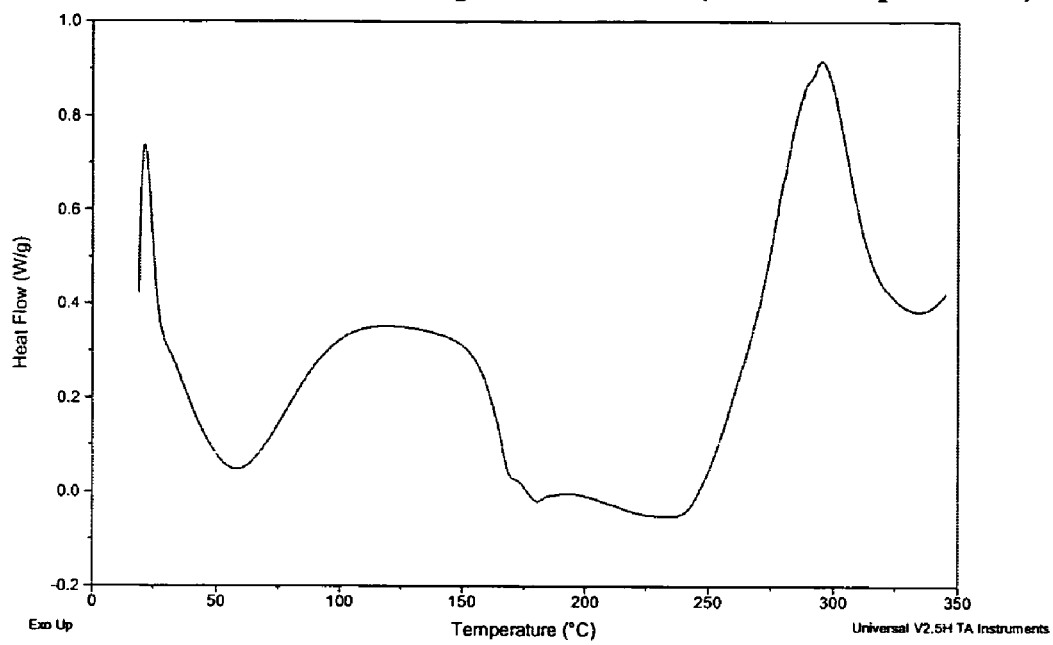
FIG. 1 shows a differential scanning calorimetry (DSC) thermogram of the stabilized amorphous form of the 1,2,3-triazole derivative II prepared by flash evaporation.

Since the compounds of the present invention, may possess asymmetric centers and, therefore, occur as mixtures of diastereomers and enantiomers, the present invention includes the individual diastereoisomeric and enantiomeric forms of the compounds of the invention in addition to the mixtures thereof.

Definitions

The term "$C_{1-6}$ alkyl" as used herein and in the claims (unless specified otherwise) mean straight or branched chain alkyl groups such as methyl, ethyl, propyl, isopropyl, butyl, isobutyl, t-butyl, amyl, hexyl and the like.

"Halogen" refers to chlorine, bromine, iodine or fluorine.

An "aryl" group refers to an all carbon monocyclic or fused-ring polycyclic (i.e., rings which share adjacent pairs of carbon atoms) groups having a completely conjugated pi-electron system. Examples, without limitation, of aryl groups are phenyl, napthalenyl and anthacenyl. The aryl group may be substituted or unsubstituted. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino and —$NR^xR^y$, wherein $R^x$ and $R^y$ are independently selected from the group consisting of hydrogen, alkyl, cycloalkyl, aryl, carbonyl, C-carboxy, sulfonyl, trihalomethyl, and, combined, a five- or six-member heteroalicyclic ring.

As used herein, a "heteroaryl" group refers to a monocyclic or fused ring (i.e., rings which share an adjacent pair of atoms) group having in the ring(s) one or more atoms selected from the group consisting of nitrogen, oxygen and sulfur and, in addition, having a completely conjugated pi-electron system. Unless otherwise indicated, the heteroaryl group may be attached at either a carbon or nitrogen atom within the heteroaryl group. It should be noted that the term heteroaryl is intended to encompass an N-oxide of the parent heteroaryl if such an N-oxide is chemically feasible as is known in the art. Examples, without limitation, of heteroaryl groups are furyl, thienyl, benzothienyl, thiazolyl, imidazolyl, oxazolyl, oxadiazolyl, thiadiazolyl, benzothiazolyl, triazolyl, tetrazolyl, isoxazolyl, isothiazolyl, pyrrolyl, pyranyl, tetrahydropyranyl, pyrazolyl, pyridyl, pyrimidinyl, quinolinyl, isoquinolinyl, purinyl, carbazolyl, benzoxazolyl, benzimidazolyl, indolyl, isoindolyl, pyrazinyl. diazinyl, pyrazine, triazinyltriazole, tetrazinyl, and tetrazolyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioaryloxy, thioheteroaryloxy, thioheteroalicycloxy, cyano, halogen, nitro, carbonyl, O-carbamyl, N-carbamyl, C-amido, N-amido, C-carboxy, O-carboxy, sulfinyl, sulfonyl, sulfonamido, trihalomethyl, ureido, amino, and —$NR^xR^y$, wherein $R^x$ and $R^y$ are as defined above.

As used herein, a "heteroalicyclic" group refers to a monocyclic or fused ring group having in the ring(s) one or more atoms selected from the group consisting of nitrogen, oxygen and sulfur. The rings may also have one or more double bonds. However, the rings do not have a completely conjugated pi-electron system. Examples, without limitation, of heteroalicyclic groups are azetidinyl, piperidyl, piperazinyl, imidazolinyl, thiazolidinyl, 3-pyrrolidin-1-yl, morpholinyl, thiomorpholinyl and tetrahydropyranyl. When substituted the substituted group(s) is preferably one or more selected from alkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halogen, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, silyl, guanyl, guanidino, ureido, phosphonyl, amino and —$NR^xR^y$, wherein $R^x$ and $R^y$ are as defined above.

An "alkyl" group refers to a saturated aliphatic hydrocarbon including straight chain and branched chain groups. Preferably, the alkyl group has 1 to 20 carbon atoms (whenever a numerical range; e.g., "1-20", is stated herein, it means that the group, in this case the alkyl group may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 4 carbon atoms. The alkyl group may be substituted or unsubstituted. When substituted, the substituent group(s) is preferably one or more individually selected from trihaloalkyl, cycloalkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalomethanesulfonamido, trihalomethanesulfonyl, and combined, a five- or six-member heteroalicyclic ring.

A "cycloalkyl" group refers to an all-carbon monocyclic or fused ring (i.e., rings which share and adjacent pair of carbon atoms) group wherein one or more rings does not have a completely conjugated pi-electron system. Examples, without limitation, of cycloalkyl groups are cyclopropane, cyclobutane, cyclopentane, cyclopentene, cyclohexane, cyclohexadiene, cycloheptane, cycloheptatriene and adamantane. A cycloalkyl group may be substituted or unsubstituted. When substituted, the substituent group(s) is preferably one or more individually selected from alkyl, aryl, heteroaryl, heteroalicyclic, hydroxy, alkoxy, aryloxy, heteroaryloxy, heteroalicycloxy, thiohydroxy, thioalkoxy, thioaryloxy, thioheteroaryloxy, thioheteroalicycloxy, cyano, halo, nitro, carbonyl, thiocarbonyl, O-carbamyl, N-carbamyl, O-thiocarbamyl, N-thiocarbamyl, C-amido, C-thioamido, N-amido, C-carboxy, O-carboxy, sulfinyl, sulfonyl, sulfonamido, trihalo-methanesulfonamido, trihalomethanesulfonyl, silyl, guanyl, guanidino, ureido, phosphonyl, amino and —$NR^xR^y$ with $R^x$ and $R^y$ as defined above.

An "alkenyl" group refers to an alkyl group, as defined herein, consisting of at least two carbon atoms and at least one carbon-carbon double bond.

An "alkynyl" group refers to an alkyl group, as defined herein, consisting of at least two carbon atoms and at least one carbon-carbon triple bond.

A "hydroxy" group refers to an —OH group.

An "alkoxy" group refers to both an —O-alkyl and an —O-cycloalkyl group as defined herein.

An "aryloxy" group refers to both an —O-aryl and an —O-heteroaryl group, as defined herein.

A "heteroaryloxy" group refers to a heteroaryl-O— group with heteroaryl as defined herein.

A "heteroalicycloxy" group refers to a heteroalicyclic-O— group with heteroalicyclic as defined herein.

A "thiohydroxy" group refers to an —SH group.

A "thioalkoxy" group refers to both an S-alkyl and an —S-cycloalkyl group, as defined herein.

A "thioaryloxy" group refers to both an —S-aryl and an —S-heteroaryl group, as defined herein.

A "thioheteroaryloxy" group refers to a heteroaryl-S— group with heteroaryl as defined herein.

A "thioheteroalicycloxy" group refers to a heteroalicyclic-S— group with heteroalicyclic as defined herein.

A "carbonyl" group refers to a —C(=O)—R" group, where R" is selected from the group consisting of hydrogen, alkyl, alkenyl, alkynyl, cycloalkyl, aryl, heteroaryl (bonded though a ring carbon) and heteroalicyclic (bonded though a ring carbon), as each is defined herein.

An "aldehyde" group refers to a carbonyl group where R" is hydrogen.

A "thiocarbonyl" group refers to a —C(=S)—R" group, with R" as defined herein.

A "Keto" group refers to a —CC(=O)C— group wherein the carbon on either or both sides of the C=O may be alkyl, cycloalkyl, aryl or a carbon of a heteroaryl or heteroaliacyclic group.

A "trihalomethanecarbonyl" group refers to a $Z_3CC$(=O)— group with said Z being a halogen.

A "C-carboxy" group refers to a —C(=O)O—R" groups, with R" as defined herein.

An "O-carboxy" group refers to a R"C(—O)O— group, with R" as defined herein.

A "carboxylic acid" group refers to a C-carboxy group in which R" is hydrogen.

A "trihalomethyl" group refers to a —$CZ_3$, group wherein Z is a halogen group as defined herein.

A "trihalomethanesulfonyl" group refers to an $Z_3CS$(=O)$_2$— groups with Z as defined above.

A "trihalomethanesulfonamido" group refers to a $Z_3CS$(=O)$_2NR^x$— group with Z and $R^x$ as defined herein.

A "sulfinyl" group refers to a —S(=O)—R" group, with R" as defined herein and, in addition, as a bond only; i.e., —S(O)—.

A "sulfonyl" group refers to a —S(=O)$_2$R" group with R" as defined herein and, in addition as a bond only; i.e., —S(O)$_2$—.

A "S-sulfonamido" group refers to a —S(=O)$_2NR^XR^Y$, with $R^X$ and $R^Y$ as defined herein.

A "N-Sulfonamido" group refers to a R"S(=O)$_2NR_X$— group with $R_x$ as defined herein.

A "O-carbamyl" group refers to a —OC(=O)$NR^xR^y$ as defined herein.

A "N-carbamyl" group refers to a $R^xOC$(=O)$NR^y$ group, with $R^x$ and $R^y$ as defined herein.

A "O-thiocarbamyl" group refers to a —OC(=S)$NR^xR^y$ group with $R^x$ and $R^y$ as defined herein.

A "N-thiocarbamyl" group refers to a $R^xOC$(=S)$NR^y$— group with $R^x$ and $R^y$ as defined herein.

An "amino" group refers to an —$NH_2$ group.

A "C-amido" group refers to a —C(=O)$NR^xR^y$ group with $R^x$ and $R^y$ as defined herein.

A "C-thioamido" group refers to a —C(=S)$NR^xR^y$ group, with $R^x$ and $R^y$ as defined herein.

A "N-amido" group refers to a $R^xC$(=O)$NR^y$— group, with $R^x$ and $R^y$ as defined herein.

A cyclic 4, 5, or six membered ring N-lactam refers to rings of 4, 5 or 6 atoms containing a single amide group as two of the ring atoms which is linked to the parent molecule at the amide nitrogen.

An "ureido" group refers to a —$NR^xC$(=O)$NR^yR^{y2}$ group with $R^x$ and $R^y$ as defined herein and $R^{y2}$ defined the same as $R^x$ and $R^y$.

A "guanidino" group refers to a —$R^xNC$(=N)$NR^yR^{y2}$ group, with $R^x$, $R^y$ and $R^{y2}$ as defined herein.

A "guanyl" group refers to a $R^xR^yNC$(=N)— group, with $R^x$ and $R^Y$ as defined herein.

A "cyano" group refers to a —CN group.

A "silyl" group refers to a —Si(R")$_3$, with R" as defined herein.

A "phosphonyl" group refers to a P(=O)(OR$^x$)$_2$ with $R^x$ as defined herein.

A "hydrazino" group refers to a —$NR^xNR^yR^{y2}$ group with $R^x$, $R^y$ and $R^{y2}$ as defined herein.

Any two adjacent R groups may combine to form an additional aryl, cycloalkyl, heteroaryl or heterocyclic ring fused to the ring initially bearing those R groups.

It is known in the art that nitrogen atoms in heteroaryl systems can be "participating in a heteroaryl ring double bond", and this refers to the form of double bonds in the two tautomeric structures which comprise five-member ring heteroaryl groups. This dictates whether nitrogens can be substituted as well understood by chemists in the art. The disclosure and claims of the present invention are based on the known general principles of chemical bonding. It is understood that the claims do not encompass structures known to be unstable or not able to exist based on the literature.

Physiologically acceptable salts and prodrugs of compounds disclosed herein are within the scope of this invention. The term "pharmaceutically acceptable salt" as used herein and in the claims is intended to include nontoxic base addition salts. Suitable salts include those derived from organic and inorganic acids such as, without limitation, hydrochloric acid, hydrobromic acid, phosphoric acid, sulfuric acid, methanesulfonic acid, acetic acid, tartaric acid, lactic acid, sulfinic acid, citric acid, maleic acid, fumaric acid, sorbic acid, aconitic acid, salicylic acid, phthalic acid, and the like. The term "pharmaceutically acceptable salt" as used herein is also intended to include salts of acidic groups, such as a carboxylate, with such counterions as ammonium, alkali metal salts, particularly sodium or potassium, alkaline earth metal salts, particularly calcium or magnesium, and salts with suitable organic bases such as lower alkylamines (methylamine, ethylamine, cyclohexylamine, and the like) or with substituted lower alkylamines (e.g. hydroxyl-substituted alkylamines such as diethanolamine, triethanolamine or tris(hydroxymethyl)-aminomethane), or with bases such as piperidine or morpholine.

In the method of the present invention, the term "antiviral effective amount" means the total amount of each active component of the method that is sufficient to show a meaningful patient benefit, i.e., healing of acute conditions characterized by inhibition of the HIV infection. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with HIV infection.

The present invention is also directed to combinations of the compounds with one or more agents useful in the treatment of AIDS. For example, the compounds of this invention may be effectively administered, whether at periods of pre-exposure and/or post-exposure, in combination with effective amounts of the AIDS antivirals, immunomodulators, antiinfectives, or vaccines, such as those in the following table.

ANTIVIRALS

| Drug Name | Manufacturer | Indication |
|---|---|---|
| 097 | Hoechst/Bayer | HIV infection, AIDS, ARC (non-nucleoside reverse transcriptase (RT) inhibitor) |
| Amprenivir 141 W94 GW 141 | Glaxo Wellcome | HIV infection, AIDS, ARC (protease inhibitor) |
| Abacavir (1592U89) GW 1592 | Glaxo Wellcome | HIV infection, AIDS, ARC (RT inhibitor) |
| Acemannan | Carrington Labs (Irving, TX) | ARC |
| Acyclovir | Burroughs Wellcome | HIV infection, AIDS, ARC, in combination with AZT |
| AD-439 | Tanox Biosystems | HIV infection, AIDS, ARC |
| AD-519 | Tanox Biosystems | HIV infection, AIDS, ARC |
| Adefovir dipivoxil AL-721 | Gilead Sciences Ethigen (Los Angeles, CA) | HIV infection ARC, PGL HIV positive, AIDS |
| Alpha Interferon | Glaxo Wellcome | Kaposi's sarcoma, HIV in combination w/Retrovir |
| Ansamycin LM 427 | Adria Laboratories (Dublin, OH) Erbamont (Stamford, CT) | ARC |
| Antibody which Neutralizes pH Labile alpha aberrant Interferon | Advanced Biotherapy Concepts (Rockville, MD) | AIDS, ARC |
| AR177 | Aronex Pharm | HIV infection, AIDS, ARC |
| Beta-fluoro-ddA | Nat'l Cancer Institute | AIDS-associated diseases |
| BMS-232623 (CGP-73547) | Bristol-Myers Squibb/Novartis | HIV infection, AIDS, ARC (protease inhibitor) |
| BMS-234475 (CGP-61755) | Bristol-Myers Squibb/Novartis | HIV infection, AIDS, ARC (protease inhibitor) |
| CI-1012 | Warner-Lambert | HIV-1 infection |
| Cidofovir | Gilead Science | CMV retinitis, herpes, papillomavirus |
| Curdlan sulfate | AJI Pharma USA | HIV infection |
| Cytomegalovirus Immune globin | MedImmune | CMV retinitis |
| Cytovene Ganciclovir | Syntex | Sight theatening CMV peripheral CMV retinitis |
| Delaviridine | Pharmacia-Upjohn | HIV infection, AIDS, ARC (RT inhibitor) |
| Dextran Sulfate | Ueno Fine Chem. Ind. Ltd. (Osaka, Japan) | AIDS, ARC, HIV positive asymptomatic |
| ddC Dideoxycytidine | Hoffman-La Roche | HIV infection, AIDS, ARC |
| ddI Dideoxyinosine | Bristol-Myers Squibb | HIV infection, AIDS, ARC; combination with AZT/d4T |
| DMP-450 | AVID (Camden, NJ) | HIV infection, AIDS, ARC (protease inhibitor) |
| Efavirenz (DMP 266) (−)-6-Chloro-4-(S)-cyclopropyl-ethynyl-4(S)-trifluoro-methyl-1,4-dihydro-2H-3,1-benzoxazin-2-one, STOCRINE | DuPont Merck | HIV infection, AIDS, ARC (non-nucleoside RT inhibitor) |
| EL10 | Elan Corp, PLC (Gainesville, GA) | HIV infection |
| Famciclovir | Smith Kline | herpes zoster, herpes simplex |
| FTC | Emory University | HIV infection, AIDS, ARC (reverse transcriptase inhibitor) |
| GS 840 | Gilead | HIV infection, AIDS, ARC (reverse transcriptase inhibitor) |
| HBY097 | Hoechst Marion Roussel | HIV infection, AIDS, ARC (non-nucleoside reverse transcriptase inhibitor) |
| Hypericin | VIMRx Pharm. | HIV infection, AIDS, ARC |
| Recombinant Human Interferon Beta | Triton Biosciences (Almeda, CA) | AIDS, Kaposi's sarcoma, ARC |

-continued

ANTIVIRALS

| Drug Name | Manufacturer | Indication |
|---|---|---|
| Interferon alfa-n3 | Interferon Sciences | ARC, AIDS |
| Indinavir | Merck | HIV infection, AIDS, ARC, asymptomatic HIV positive, also in combination with AZT/ddI/ddC |
| ISIS 2922 | ISIS Pharmaceuticals | CMV retinitis |
| KNI-272 | Nat'l Cancer Institute | HIV-assoc. diseases |
| Lamivudine, 3TC | Glaxo Wellcome | HIV infection, AIDS, ARC (reverse transcriptase inhibitor); also with AZT |
| Lobucavir | Bristol-Myers Squibb | CMV infection |
| Nelfinavir | Agouron Pharmaceuticals | HIV infection, AIDS, ARC (protease inhibitor) |
| Nevirapine | Boeheringer Ingleheim | HIV infection, AIDS, ARC (RT inhibitor) |
| Novapren | Novaferon Labs, Inc. (Akron, OH) | HIV inhibitor |
| Peptide T Octapeptide Sequence | Peninsula Labs (Belmont, CA) | AIDS |
| Trisodium Phosphonoformate | Astra Pharm. Products, Inc. | CMV retinitis, HIV infection, other CMV infections |
| PNU-140690 | Pharmacia Upjohn | HIV infection, AIDS, ARC (protease inhibitor) |
| Probucol | Vyrex | HIV infection, AIDS |
| RBC-CD4 | Sheffield Med. Tech (Houston, TX) | HIV infection, AIDS, ARC |
| Ritonavir | Abbott | HIV infection, AIDS, ARC (protease inhibitor) |
| Saquinavir | Hoffmann-LaRoche | HIV infection, AIDS, ARC (protease inhibitor) |
| Stavudine; d4T Didehydrodeoxythymidine | Bristol-Myers Squibb | HIV infection, AIDS, ARC |
| Valaciclovir | Glaxo Wellcome | Genital HSV & CMV infections |
| Virazole Ribavirin | Viratek/ICN (Costa Mesa, CA) | asymptomatic HIV positive, LAS, ARC |
| VX-478 | Vertex | HIV infection, AIDS, ARC |
| Zalcitabine | Hoffmann-LaRoche | HIV infection, AIDS, ARC, with AZT |
| Zidovudine; AZT | Glaxo Wellcome | HIV infection, AIDS, ARC, Kaposi's sarcoma, in combination with other therapies |
| Tenofovir disoproxil, fumarate salt (Viread ®) | Gilead | HIV infection, AIDS, (reverse transcriptase inhibitor) |
| Combivir ® | GSK | HIV infection, AIDS, (reverse transcriptase inhibitor) |
| abacavir succinate (or Ziagen ®) | GSK | HIV infection, AIDS, (reverse transcriptase inhibitor) |
| REYATAZ ® (or atazanavir) | Bristol-Myers Squibb | HIV infection AIDS, protease inhibitor |
| FUZEON (or T-20) | Roche/Trimeris | HIV infection AIDS, viral Fusion inhibitor |

IMMUNOMODULATORS

| Drug Name | Manufacturer | Indication |
|---|---|---|
| AS-101 | Wyeth-Ayerst | AIDS |
| Bropirimine | Pharmacia Upjohn | Advanced AIDS |
| Acemannan | Carrington Labs, Inc. (Irving, TX) | AIDS, ARC |
| CL246,738 | American Cyanamid Lederle Labs | AIDS, Kaposi's sarcoma |
| EL10 | Elan Corp, PLC (Gainesville, GA) | HIV infection |
| FP-21399 | Fuki ImmunoPharm | Blocks HIV fusion with CD4+ cells |
| Gamma Interferon | Genentech | ARC, in combination w/TNF (tumor necrosis factor) |
| Granulocyte Macrophage Colony Stimulating Factor | Genetics Institute Sandoz | AIDS |
| Granulocyte Macrophage Colony Stimulating Factor | Hoechst-Roussel Immunex | AIDS |
| Granulocyte Macrophage Colony Stimulating Factor | Schering-Plough | AIDS, combination w/AZT |
| HIV Core Particle Immunostimulant | Rorer | Seropositive HIV |
| IL-2 Interleukin-2 | Cetus | AIDS, in combination w/AZT |
| IL-2 Interleukin-2 | Hoffman-LaRoche Immunex | AIDS, ARC, HIV, in combination w/AZT |
| IL-2 Interleukin-2 (aldeslukin) | Chiron | AIDS, increase in CD4 cell counts |
| Immune Globulin Intravenous (human) | Cutter Biological (Berkeley, CA) | Pediatric AIDS, in combination w/AZT |
| IMREG-1 | Imreg (New Orleans, LA) | AIDS, Kaposi's sarcoma, ARC, PGL |
| IMREG-2 | Imreg (New Orleans, LA) | AIDS, Kaposi's sarcoma, ARC, PGL |
| Imuthiol Diethyl Dithio Carbamate | Merieux Institute | AIDS, ARC |
| Alpha-2 Interferon | Schering Plough | Kaposi's sarcoma w/AZT, AIDS |
| Methionine-Enkephalin | TNI Pharmaceutical (Chicago, IL) | AIDS, ARC |
| MTP-PE Muramyl-Tripeptide | Ciba-Geigy Corp. | Kaposi's sarcoma |
| Granulocyte Colony Stimulating Factor | Amgen | AIDS, in combination w/AZT |
| Remune | Immune Response Corp. | Immunotherapeutic |
| rCD4 Recombinant Soluble Human CD4 | Genentech | AIDS, ARC |
| rCD4-IgG hybrids | | AIDS, ARC |
| Recombinant Soluble Human CD4 | Biogen | AIDS, ARC |
| Interferon Alfa 2a | Hoffman-La Roche | Kaposi's sarcoma AIDS, ARC, in combination w/AZT |
| SK&F106528 Soluble T4 Thymopentin | Smith Kline Immunobiology Research Institute (Annandale, NJ) | HIV infection HIV infection |
| Tumor Necrosis Factor; TNF | Genentech | ARC, in combination w/gamma Interferon |

ANTI-INFECTIVES

| Drug Name | Manufacturer | Indication |
|---|---|---|
| Clindamycin with Primaquine | Pharmacia Upjohn | PCP |

-continued

ANTI-INFECTIVES

| Drug Name | Manufacturer | Indication |
| --- | --- | --- |
| Fluconazole | Pfizer | Cryptococcal meningitis, candidiasis |
| Pastille Nystatin Pastille | Squibb Corp. | Prevention of oral candidiasis |
| Ornidyl Eflornithine | Merrell Dow | PCP |
| Pentamidine Isethionate (IM & IV) | LyphoMed (Rosemont, IL) | PCP treatment |
| Trimethoprim | | Antibacterial |
| Trimethoprim/sulfa | | Antibacterial |
| Piritrexim | Burroughs Wellcome | PCP treatment |
| Pentamidine Isethionate for Inhalation | Fisons Corporation | PCP prophylaxis |
| Spiramycin | Rhone-Poulenc | Cryptosporidial diarrhea |
| Intraconazole-R51211 | Janssen-Pharm. | Histoplasmosis; cryptococcal meningitis |
| Trimetrexate | Warner-Lambert | PCP |
| Daunorubicin | NeXstar, Sequus | Kaposi's sarcoma |
| Recombinant Human Erythopoietin | Ortho Pharm. Corp. | Severe anemia assoc. with AZT therapy |
| Recombinant Human Growth Hormone | Serono | AIDS-related wasting, cachexia |
| Megestrol Acetate | Bristol-Myers Squibb | Treatment of anorexia assoc. w/AIDS |
| Testosterone | Alza, Smith Kline | AIDS-related wasting |
| Total Enteral Nutrition | Norwich Eaton Pharmaceuticals | Diarrhea and malabsorption related to AIDS |

Additionally, the compounds of the invention herein may be used in combination with another class of agents for treating AIDS which are called HIV entry inhibitors. Examples of such HIV entry inhibitors are discussed in Drugs of the Future 1999, 24(12), pp. 1355-1362; Cell, Vol. 9, pp. 243-246, Oct. 29, 1999; and Drug Discovery Today, Vol. 5, No. 5, May 2000, pp. 183-194.

It will be understood that the scope of combinations of the compounds of this invention with AIDS antivirals, immunomodulators, anti-infectives, HIV entry inhibitors or vaccines is not limited to the list in the above Table, but includes in principle any combination with any pharmaceutical composition useful for the treatment of AIDS.

Preferred combinations are simultaneous or alternating treatments with a compound of the present invention and an inhibitor of HIV protease and/or a non-nucleoside inhibitor of HIV reverse transcriptase. An optional fourth component in the combination is a nucleoside inhibitor of HIV reverse transcriptase, such as AZT, 3TC, ddC or ddI. A preferred inhibitor of HIV protease is indinavir, which is the sulfate salt of N-(2(R)-hydroxy-1-(S)-indanyl)-2(R)-phenylmethyl-4-(S)-hydroxy-5-(1-(4-(3-pyridyl-methyl)-2(S)—N'-(t-butyl-carboxamido)-piperazinyl))-pentaneamide ethanolate, and is synthesized according to U.S. Pat. No. 5,413,999. Indinavir is generally administered at a dose of 800 mg thee times a day. Other preferred protease inhibitors are nelfinavir and ritonavir. Another preferred inhibitor of HIV protease is saquinavir which is administered at a dose of 600 or 1200 mg tid. Preferred non-nucleoside inhibitors of HIV reverse transcriptase include efavirenz. The preparation of ddC, ddI and AZT are also described in EPO 0,484,071. These combinations may have unexpected effects on limiting the spread and degree of infection of HIV. Preferred combinations include those with the following (1) indinavir with efavirenz, and, optionally, AZT and/or 3TC and/or ddI and/or ddC; (2) indinavir, and any of AZT and/or ddI and/or ddC and/or 3TC, in particular, indinavir and AZT and 3TC; (3) stavudine and 3TC and/or zidovudine; (4) zidovudine and lamivudine and 141W94 and 1592U89; (5) zidovudine and lamivudine.

In such combinations the compound of the present invention and other active agents may be administered separately or in conjunction. In addition, the administration of one element may be prior to, concurrent to, or subsequent to the administration of other agent(s).

The preparative procedures and anti-HIV-1 activity of the novel azaindole piperazine diamide analogs of Formulas IA and IIA are summarized hereinafter:

Abbreviations

The following abbreviations, most of which are conventional abbreviations well known to those skilled in the art, are used thoughout the description of the invention and the examples. Some of the abbreviations used are as follows:

h=hour(s)
rt=room temperature
mol=mole(s)
mmol=millimole(s)
g=gram(s)
mg=milligram(s)
mL=milliliter(s)
TFA=Trifluoroacetic Acid
DCE=1,2-Dichloroethane
$CH_2Cl_2$=Dichloromethane
TPAP=tetrapropylammonium perruthenate
THF=Tetrahydofuran
DEPBT=3-(Diethoxyphosphoryloxy)-1,2,3-benzotriazin-4(3H)-one
DMAP=4-dimethylaminopyridine
P-EDC=Polymer supported 1-(3-dimethylaminopropyl)-3-ethylcarbodiimide
EDC=1-(3-dimethylaminopropyl)-3-ethylcarbodiimide
DMF=N,N-dimethylformamide
Hunig's Base=N,N-Diisopropylethylamine
DMA=dimethylacetamide
AcOH=acetic acid
IPA=isopropyl alcohol
PVP=Polyvinylpyrrolidone (Plasdone, Povidone)
SDI=Spray dried intermediate
PEG=Polyethylene glycol
mCPBA=meta-Chloroperbenzoic Acid
azaindole=1H-Pyrrolo-pyridine
4-azaindole=1H-pyrrolo[3,2-b]pyridine
5-azaindole=1H-Pyrrolo[3,2-c]pyridine
6-azaindole=1H-pyrrolo[2,3-c]pyridine
7-azaindole=1H-Pyrrolo[2,3-b]pyridine
PMB=4-Methoxybenzyl
DDQ=2,3-Dichloro-5,6-dicyano-1,4-benzoquinone
OTf=Trifluoromethanesulfonoxy
NMM=4-Methylmorpholine
PIP-COPh=1-Benzoylpiperazine
NaHMDS=Sodium hexamethyldisilazide
EDAC=1-(3-Dimethylaminopropyl)-3-ethylcarbodiimide
TMS=Trimethylsilyl
DCM=Dichloromethane
DCE=Dichloroethane
MeOH=Methanol
THF=Tetrahdrofuran
EtOAc=Ethyl Acetate
LDA=Lithium diisopropylamide
TMP-Li=2,2,6,6-tetramethylpiperidinyl lithium DME=Dimethoxyethane
DIBALH=Diisobutylaluminum hydride
HOBT=1-hydroxybenzotriazole
CBZ=Benzyloxycarbonyl
PCC=Pyridinium chlorochomate
Me=Methyl
Ph=Phenyl New Forms The present invention includes crystalline Form N-1 and the stabilized amorphous form of the 1,2,3-triazole derivative II, their pharmaceutical formulations, and their use in patients suffering from or susceptible to HIV infection. The compounds of Formula II include pharmaceutically acceptable salts thereof.

The present invention provides, at least in part, N-1 crystalline form of 1,2,3-triazole derivative II as a novel material, in particular in pharmaceutically acceptable form. The term "pharmaceutically acceptable", as used herein, refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. In certain preferred embodiments, the N-1 form and stabilized amorphous form of 1,2,3-triazole derivative II and salts thereof are in substantially pure form. The term "substantially pure", as used herein, means a compound having a purity greater than about 90% including, for example, about 91%, about 92%, about 93%, about 94%, about 95%, about 96%, about 97%, about 98%, about 99%, and about 100%.

As used herein "polymorph" refers to crystalline forms having the same chemical composition but different spatial arrangements of the molecules, atoms, and/or ions forming the crystal.

As used herein "solvate" refers to a crystalline form of a molecule, and/or ions that further contains molecules of a solvent or solvents incorporated into the crystalline structure. The solvent molecules in the solvate may be present in a regular arrangement and/or a non-ordered arrangement. The solvate may contain either a stoichiometric or nonstoichiometric amount of the solvent molecules. For example, a solvate with a nonstoichiometric amount of solvent molecules may result from partial loss of solvent from the solvate.

Samples of the crystalline forms may be provided with substantially pure phase homogeneity, indicating the presence of a dominant amount of a single crystalline form and optionally minor amounts of one or more other crystalline forms. The presence of more than one crystalline form in a sample may be determined by techniques such as powder X-ray diffraction (PXRD) or solid state nuclear magnetic resonance spectroscopy (SSNMR). For example, the presence of extra peaks in the comparison of an experimentally measured PXRD pattern with a simulated PXRD pattern may indicate more than one crystalline form in the sample. The simulated PXRD may be calculated from single crystal X-ray data (see Powder Diffraction Simulation and Structure Display, Materials Data Inc., Livermore, Calif., USA, 2001). Preferably, the crystalline form has substantially pure phase homogeneity as indicated by less than 10%, preferably less than 5%, and more preferably less than 2% of the total peak area in the experimentally measured PXRD pattern arising from the extra peaks that are absent from the simulated PXRD pattern. Most preferred is a crystalline form having substantially pure phase homogeneity with less than 1% of the total peak area in the experimentally measured PXRD pattern arising from the extra peaks that are absent from the simulated PXRD pattern.

Procedures for the preparation of crystalline forms are known in the art. The crystalline forms may be prepared by a variety of methods, including for example, crystallization or recrystallization from a suitable solvent, sublimation, growth from a melt, solid state transformation from another phase, crystallization from a supercritical fluid, and jet spraying. Techniques for crystallization or recrystallization of crystalline forms from a solvent mixture include, for example, evaporation of the solvent, decreasing the temperature of the solvent mixture, crystal seeding a supersaturated solvent mixture of the molecule and/or salt, freeze drying the solvent mixture, and addition of antisolvents (countersolvents) to the solvent mixture. High thoughput crystallization techniques may be employed to prepare crystalline forms including polymorphs.

Crystals of drugs, including polymorphs, methods of preparation, and characterization of drug crystals are discussed in *Solid-State Chemistry of Drugs*, S. R. Byrn, R. R. Pfeiffer, and J. G. Stowell, $2^{nd}$ Edition, SSCI, West Lafayette, Ind. (1999).

For crystallization techniques that employ solvent, the choice of solvent or solvents is typically dependent upon one or more factors, such as solubility of the compound, crystallization technique, and vapor pressure of the solvent. Combinations of solvents may be employed, for example, the compound may be solubilized into a first solvent to afford a solution, followed by the addition of an antisolvent to decrease the solubility of the compound in the solution and to afford the formation of crystals. An antisolvent is a solvent in which the compound has low solubility. Suitable solvents for preparing crystals include polar and nonpolar solvents.

In one method to prepare crystals, 1,2,3-triazole derivative II or a salt thereof is suspended and/or stirred in a suitable solvent to afford a slurry, which may be heated to promote dissolution. The term "slurry", as used herein, means a saturated solution of Compound II or a salt thereof, which may also contain an additional amount of Compound II or salt thereof to afford a heterogeneous mixture of Compound II or salt thereof and a solvent at a given temperature. Suitable solvents in this regard include, for example, polar aprotic solvents, and polar protic solvents, and mixtures of two or more of these as disclosed herein.

Seed crystals may be added to any crystallization mixture to promote crystallization. As will be clear to the skilled artisan, seeding is used as a means of controlling growth of a particular crystalline form or as a means of controlling the particle size distribution of the crystalline product. Accordingly, calculation of the amount of seeds needed depends on the size of the seed available and the desired size of an average product particle as described, for example, in "Programmed cooling of batch crystallizers," J. W. Mullin and J. N'yvlt, *Chemical Engineering Science* (1971) 26:369-377. In general, seeds of small size are needed to effectively control the growth of crystals in the batch. Seeds of small size may be generated by sieving, milling, or micronizing of larger crystals, or by micro-crystallization of solutions. Care should be taken that milling or micronizing of crystals does not result in any change in crystallinity from the desired crystal form (i.e. change to amorphous or to another polymorph).

A cooled mixture may be filtered under vacuum, and the isolated solids may be washed with a suitable solvent, such as cold recrystallization solvent, and dried under a nitrogen purge to afford the desired crystalline form. The isolated solids may be analyzed by a suitable spectroscopic or analytical technique, such as SSNMR, IR, FT-IR, Raman, DSC, PXRD, or the like, to assure formation of the preferred crystalline form of the product. The resulting crystalline form is typically produced in an amount of greater than about 70 weight % isolated yield, but preferably greater than 90 weight % based on the weight of 1,2,3-triazole derivative II originally employed in the crystallization procedure. The product may be comilled or passed though a mesh screen to delump the product, if necessary.

Crystalline forms may be prepared directly from the reaction medium of the final process step for preparing 1,2,3-triazole derivative II. This may be achieved, for example, by employing in the final process step a solvent or mixture of solvents from which 1,2,3-triazole derivative II may be crystallized. Alternatively, crystalline forms may be obtained by evaporation, by distillation or solvent addition techniques. Suitable solvents for this purpose include any of those solvents described herein, including protic polar solvents such as alcohols, and aprotic polar solvents such as ketones.

By way of general guidance, the reaction mixture may be filtered to remove any undesired impurities, inorganic salts, and the like, followed by washing with reaction or crystallization solvent. The resulting solution may be concentrated to remove excess solvent or gaseous constituents. If distillation is employed, the ultimate amount of distillate collected may vary, depending on process factors including, for example, vessel size, stirring capability, and the like. By way of general guidance, the reaction solution may be distilled to about {fraction (1/10)} the original volume before solvent replacement is carried out. The reaction may be sampled and assayed to determine the extent of the reaction and the wt % product in accordance with standard process techniques. If desired, additional reaction solvent may be added or removed to optimize reaction concentration. Preferably, the final concentration is adjusted to about 50 wt % at which point a slurry typically results.

It may be preferable to add solvents directly to the reaction vessel without distilling the reaction mixture. Preferred solvents for this purpose are those which may ultimately participate in the crystalline lattice as discussed above in connection with solvent exchange. Although the final concentration may vary depending on the desired purity, recovery and the like, the final concentration of 1,2,3-triazole derivative II in solution is preferably about 4% to about 7%. The reaction mixture may be stirred following solvent addition and simultaneously warmed. By way of illustration, the reaction mixture may be stirred for about 1 hour while warming to about 70° C. The reaction is preferably filtered hot and washed with either the reaction solvent, the solvent added or a combination thereof. Seed crystals may be added to any crystallization solution to initiate crystallization.

The various forms described herein may be distinguishable from one another though the use of various analytical techniques known to one of ordinary skill in the art. Such techniques include, but are not limited to, solid state nuclear magnetic resonance (SSNMR) spectroscopy, IR, FT-IR, Raman, X-ray powder diffraction (PXRD), differential scanning calorimetry (DSC), and/or thermogravimetric analysis (TGA).

One of ordinary skill in the art will appreciate that an X-ray diffraction pattern may be obtained with a measurement error that is dependent upon the measurement conditions employed. In particular, it is generally known that intensities in a X-ray diffraction pattern may fluctuate depending upon measurement conditions employed and the shape or morphology and the orientation of the crystal. It should be further understood that relative intensities may also vary depending upon experimental conditions and, accordingly, the exact order of intensity should not be taken into account. Additionally, a measurement error of diffraction angle for a conventional X-ray diffraction pattern is typically about 0.2% or less, preferably about 0.1% (as discussed hereinafter), and such degree of measurement error should be taken into account as pertaining to the aforementioned diffraction angles. Consequently, it is to be understood that the crystal forms of the current invention are not limited to the crystal forms that provide X-ray diffraction patterns completely identical to the X-ray diffraction patterns depicted in the accompanying Figures disclosed herein. Any or all crystal forms that provide X-ray diffraction patterns substantially identical to those disclosed in the accompanying Figures fall within the scope of the present invention. The ability to ascertain substantial identities of X-ray diffraction patterns is within the purview of one of ordinary skill in the art.

New Processes

The process of the invention for preparing the 1,2,4-triazole derivative IA and the 1,2,3-triazole derivative IIA, and intermediates useful for their synthesis, are shown in detail in Schemes I and II, respectively.

The sequence of reactions in Schemes I and II show a general organization of the steps from the starting material a. to the final step resulting in the 1,2,4-triazole derivative IA (or I) (Scheme I) and from the starting material b. to the final step resulting in the 1,2,3-triazole derivative IIA (or II) (Scheme II). As is shown below, each of the steps may include a variety of reaction conditions to achieve the desired product. This is further shown in the working examples set out hereinafter.

SCHEME 1
Synthesis Scheme for Compounds I and IA

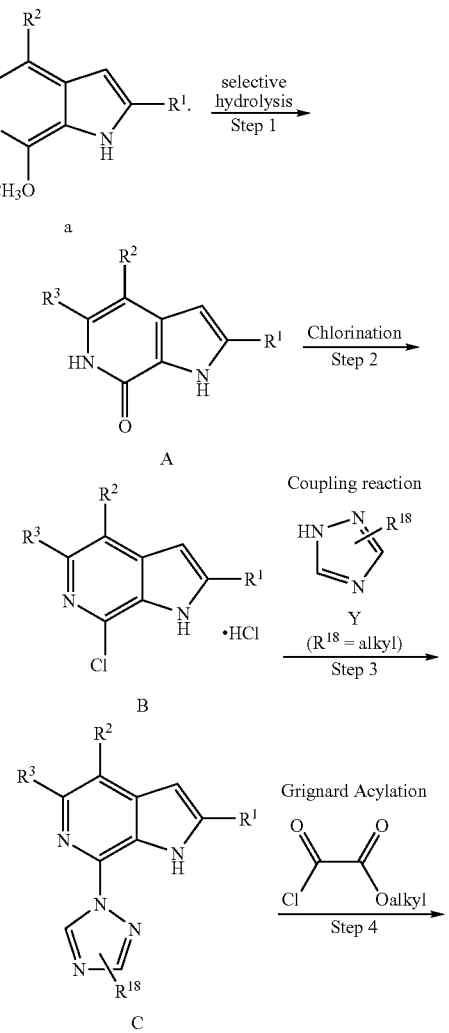

-continued

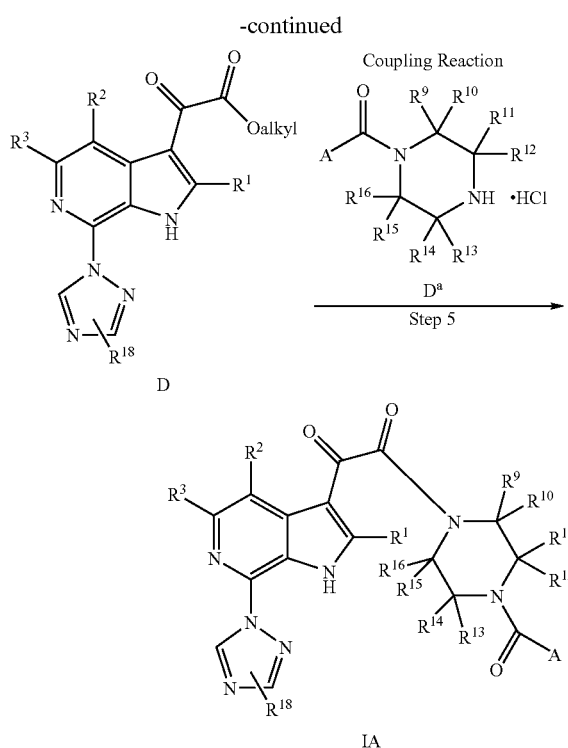

D

IA

Referring to Scheme I, in Step 1, compound a (where $R^2$ is preferably alkoxy, more preferably methoxy, $R^3$ is preferably H, and $R^1$ is preferably H), is subjected to selective hydrolysis wherein compound a. is mixed with an organic solvent such as 1-methyl-2-pyrrolidinone, DMSO, DMF, DMA or AcOH/HBr—HCl—HI, and/or water and the mixture is heated at a temperature within the range from about 80 to about 100° C. to form compound A.

Compound A is chlorinated by reacting A with a chlorine source, such as $POCl_3$ (employing a molar ratio of chlorine source: Compound a. within the range from about 20:1 to about 25:1, (preferably from about 22:1 to about 23:1) under an inert atmosphere such as argon, while maintaining the temperature at or less than about 24° C., to form a slurry, and heating the slurry at a temperature, from about 85 to about 105° C. with stirring to form the chlorinated compound B.

Compound B is then made to undergo a coupling reaction with 1,2,4-triazole Y, that is

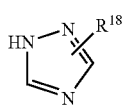

Y wherein $R^{18}$ is alkyl, preferably 3-methyl or 3-ethyl, to form compound C. The coupling reaction is carried out employing a molar ratio of compound Y: Compound B within the range from about 3:1 to about 10:1, preferably from about 4:1 to about 6:1 and a temperature within the range from about 140 to about 145° C.

Compound C is then subjected to a Grignard acylation wherein compound C is mixed with an organic solvent THF, and MeTHF, as well as toluene, and methylene chloride, and the resulting suspension is cooled to a temperature within the range from about −40 to about −25° C. The cooled slurry is treated with a solution of a Grignard reagent such as $C_2H_5MgCl$ (employing a molar ratio of $C_2H_5MgCl$:compound C within the range from about 3.4:1 to about 4:1, preferably from about 3.5:1 to about 3.6:1) in THF or other organic solvent such as toluene or methylene chloride, while maintaining a temperature within the range from about −50° C. to about 25°. Organic base such as pyridine, or picoline or lutidine is added to the reaction mixture in a molar ratio to compound C within the range from about 0.5:1 to about 1:1. The reaction is cooled to a temperature from about −40° C. to about −50° C. and methyl chlorooxoacetate is added (molar ratio of added chloride:compound C within the range from about 3.4:1 to about 5:1, preferably from about 3.5:1 to about 3.6:1) while maintaining internal temperature within the range from about −50° C. to about −40° C. The reaction is warmed to a temperature within the range from about −15 to about −5° C. and compound D is recovered.

Compound D is then coupled with piperazine derivative $D^a$

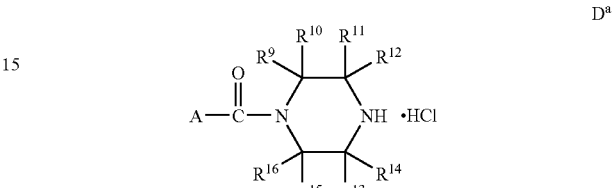

$D^a$ employing a molar ratio of $D^a$:D within the range from about 1.3 to about 1.1:1, preferably from about 1.2 to about 1.1:1. An organic base such as sodium t-butoxide, potassium t-butoxide or lithium t-butoxide (molar ratio:D within the range from about 2.5:1 to about 3:1) is added and the reaction is stirred at a temperature within the range from about 15 to about 22° C. and then cooled to about 3 to about 110° C. Compound IA is formed and may be recrystallized as described hereinafter in the examples.

Still further in accordance with the present invention, a process is provided for preparing 3-methyl-1,2,4-triazole

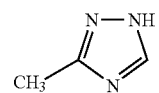

$Y^a$ which includes the steps of a) preparing a reaction mixture of acetamidine hydrochloride, ethanol and sodium methoxide, having a temperature below about 20° C., preferably within the range from about 10 to about 19° C., b) reacting formic hydrazine with the reaction mixture from step a) at a temperature within the range from about 25° C. to about 60° C., preferably from about 50 to about 60° C., and c) recovering 3-methyl-1,2,4-triazole.

The starting material a. in Scheme I is prepared as outlined in Scheme IA below.

SCHEME IA

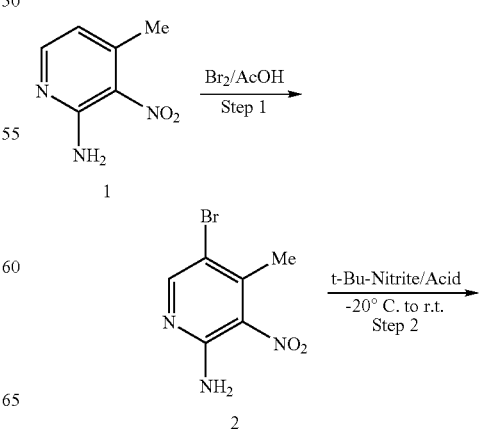

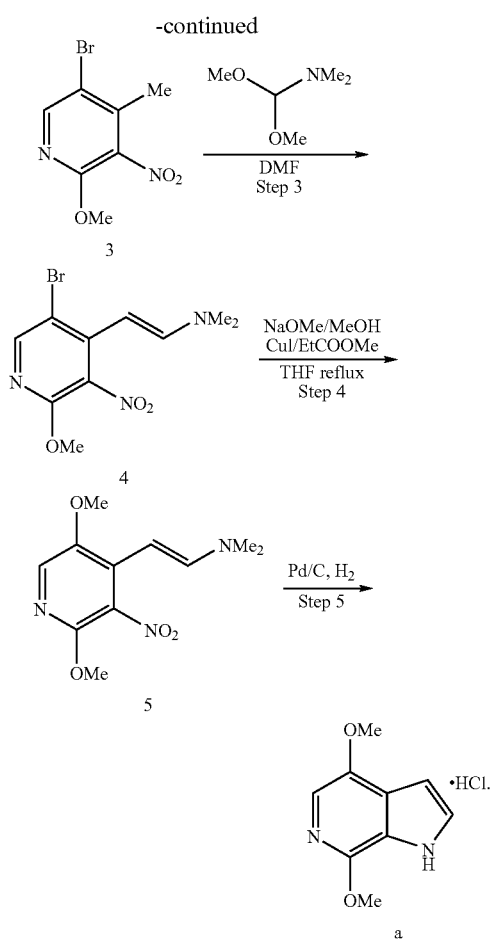

Referring to Scheme IA, Step 1, the conversion of the compound of formula 1 to the compound of formula 2 is achieved though the introduction of bromine ($Br_2$) in acetic acid (AcOH). The amount of bromine is in the range of about 0.5 to about 2 equivalents (eq.)

Step 2 is conducted with the addition of tert-butyl nitrite (t-Bu-Nitrite) in the presence of an acid. The acid may be generated in situ using acetyl chloride and alcohol. The reaction is exothermic and therefore cooling may be added as necessary. Also, to neutralize acid at the end of the reaction sodium bicarbonate solution may be added.

Step 3 includes the use of N,N-dimethyl formamide-dimethyl acetal in addition to dimethyl formamide (DMF) as a solvent and lithium methoxide (LiOMe) in methanol (MeOH). The reaction is endothermic. Therefore, heat may be added as necessary.

Step 4 is also a slightly exothermic reaction. Copper iodide (CuI) is added in a range of 0.05 to 0.8 eq., desirably from 0.2 to about 0.3 eq. This is followed by the addition of methyl propionate (EtCOOMe) (from about 5 to about 20 eq.), tetrahydrofuran (THF) (from about 5 to about 20 eq.), and sodium methoxide (NaOMe) (from about 5 to about 25 eq.). The reaction mixture is heated to reflux temperature (65° C. to about 75° C.) until the reaction is complete.

Step 5 is the cyclization of the compound of formula 5 to the compound of formula 6 by reduction reaction. A variety of catalysts are useful for this including palladium over carbon (Pd/C) (Pd—C transfer hydrogenation conditions) and precious metal catalysts such as Pt/C available as Escat 261 or Escat 160 from Englehard (reductions can also be done using other metals such as Zn and Fe, as well as with sodium dithionate). The reaction is conducted in the presence of ethyl acetate (EtOAc) under hydrogen ($H_2$) pressure in a range from about 10 PSI to about 50 PSI.

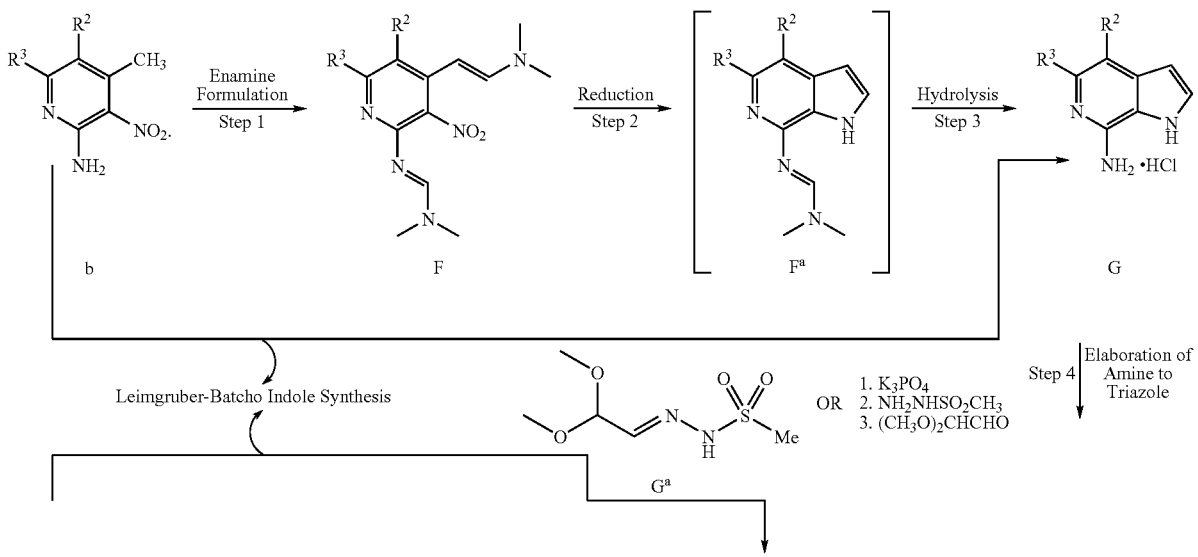

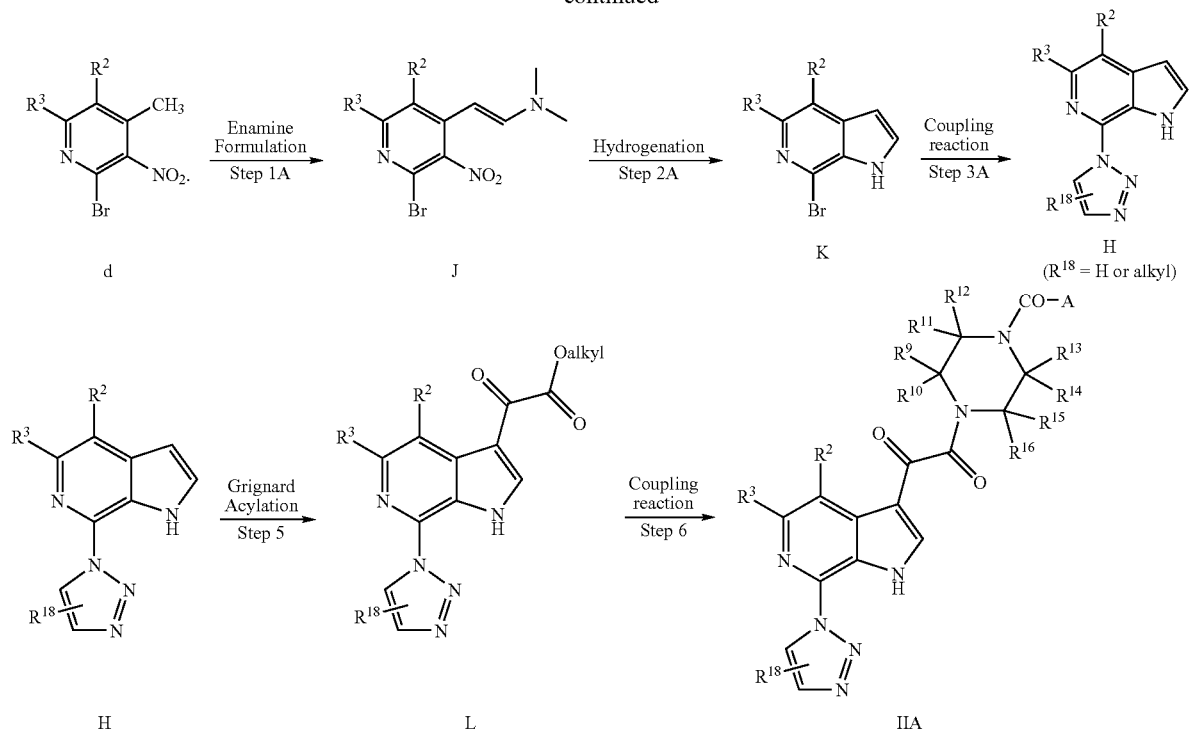

Referring to Scheme II, a Leimgruber-Batcho indole synthesis is outlined in Steps 1, 2 and 3. Thus, in Step 1, compound b. is subjected to enamine formation wherein compound b is mixed with an organic solvent such as N,N-dimethyl formamide (DMF), and DMF-dimethyl acetal c.

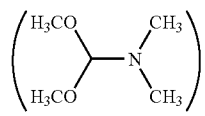

employing a molar ratio of acetal c:compound b within the range from about 3.5:1 to about 5:1, preferably from about 3.75:1 to about 4:1. The reaction mixture is warmed to a temperature within the range from about 110 to about 130° C. and distilling off the volatiles to form compound F. The reaction mixture is cooled to a temperature within the range from about 5 to about 15° C., water is added and after stirring, compound F is recovered.

In Step 2, compound F is cyclized via a reduction reaction to form compound $F^\alpha$. The reduction is carried out in the presence of platinum on carbon (available as CP126 catalyst, Escat 261 or Escat 160—Englehard Industries), although a variety of catalysts are useful in such reduction including palladium over carbon (Pd/C), Pd—C, Zn, Fe or sodium dithionate. The reduction is carried out under hydrogen ($H_2$) pressure in a range from about 15 to about 60 psi at a temperature within the range from about 15 to about 35° C.

Compound $F^\alpha$ is formed which is treated with acid such as hydrochloric acid to hydrolyze compound $F^\alpha$ and form amine compound G HCl salt (Step 3).

In Step 4, amine compound G HCl salt is converted to 1,2,3-triazole derivative H by treating compound G HCl salt with a base such as $K_3PO_4$, methylsulfonyl hydrazide, an organic solvent such as acetonitrile, and 2,2-dimethoxyacetaldehyde in water. The elaboration of amine compound G HCl salt to the 1,2,3-triazole derivative H is carried out employing a molar ratio of $K_3PO_4$ to compound G HCl salt within the range from about 0.5:1 to about 2:1, preferably from about 1.0:1 to about 1.1:1, a molar ratio of methylsulfonyl hydrazide:compound G HCl salt within the range from about 1.0:1 to about 2.5:1, preferably from about 1.4:1 to about 1.7:1, and a molar ratio 2,2-dimethoxyacetaldehyde: compound G HCl salt within the range from about 1.0:1 to about 2.2:1, preferably from about 1.2:1 to about 1.4:1, at a temperature within the range from about 30 to about 130° C., preferably from about 50 to about 80° C.

As seen in Scheme II, 1,2,3-triazole derivative H can also be prepared starting with compound d. A Leimgruber-Batcho indole synthesis is outlined in Steps 1A and 2A. In Step 1A, compound d. is converted via enamine formation to compound J wherein compound d. is treated with an organic base such as lithium methoxide (employing a molar ratio of base: compound d. within the range from about 0.05:1 to about 0.15:1), an organic solvent such as N,N-dimethylformamide (DMF), and DMF-dimethyl acetal c.

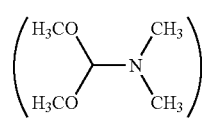

employing a molar ratio of acetal c:compound d within the range from about 3:1 to about 8:1. The reaction mixture is warmed to a temperature within the range from about 80 to about 85° C. Compound J is thereby formed.

In Step 2A, compound J is cyclized via a reduction reaction employing any of the catalysts and reaction conditions set out above with respect to Step 2 in Scheme II wherein compound F is cyclized to compound F'. However, the reduction of compound J to compound K is carried out at a temperature within the range from about 25 to about 50° C.

In Step 3A compound K is made to undergo a coupling reaction wherein compound K is treated with a base such as $K_2HPO_4$, a copper catalyst such as $Cu_2O$ and 1,2,3-triazole Y'.

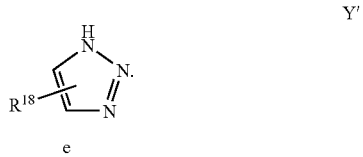

where $R^{18}$ is H or alkyl, and the reaction is heated at a temperature within the range from about 120 to about 160° C. to form 1,2,3-triazole derivative H. The coupling reaction is carried out employing a molar ratio of base:compound K within the range from about 0.8:1 to about 1.2:1, preferably from about 0.9:1 to about 1.1:1, a molar ratio of $Cu_2O$:compound K within the range from about 0.1:1 to about 1.0:1, preferably from about 0.15:1 to about 0.25:1, and a molar ratio of 1,2,3-triazole e:compound K within the range from about 10:1 to about 30:1, preferably from about 13:1 to about 18:1.

Compound H may also be prepared by reacting compound $G^a$

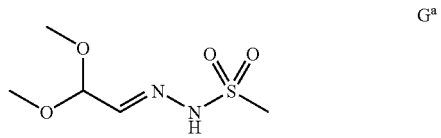

with neutralized compound G, and $K_2HPO_4$ (potassium phosphate, dibasic) in the presence of organic solvents like dimethylacetamide/acetonitrile/ethyl acetate. In carrying out the above reaction, compound $G^a$ will be employed in a molar ratio to compound G within the range from about 1.5:1 to about 1.2:1, preferably from about 1.2:1 to about 1.3:1 and the $K_2HPO_4$ will be employed in a molar ratio to compound G within the range from about 1.4:1 to about 1:1, preferably from about 1.2:1 to about 1.3:1.

In Step 5, compound H is subjected to a Grignard acylation wherein compound H is mixed with an organic solvent such as 2-methyltetrahydrofuran (2-MeTHF), or a mixture of toluene:methylene chloride (1:2 to 2:1, preferably 2:1), the resulting suspension is cooled to a temperature within the range from about −5 to about −15° C., and the cooled slurry is treated with a solution of a Grignard reagent such as $C_2H_5MgCl$ in THF (molar ratio Grignard:THF from about 2:1 to about 2.5:1, preferably 2.2:1) (molar ratio of $C_2H_5MgCl$:compound H within the range from about 3.4:1 to about 4:1, preferably from about 3.5:1 to about 3.6:1) while maintaining temperature within the range from about −15° C. to about 0° C. Organic base such as pyridine, picoline or lutidine is added to the reaction mixture in a molar ratio to substrate H within the range from about 0.5:1 to about 1.5:1. The reaction is cooled to a temperature from about −40° C. to about −50° C. and methyl chlorooxoacetate is added (molar ratio of acid chloride:substrate H within the range from about 3.4:1 to about 5:1, preferably from about 3.5:1 to about 4:1) while maintaining internal temperature within the range from about −50° C. to about −40° C. The reaction is warmed to a temperature within the range from about −15 to about −5° C. and compound L is recovered.

In Step 5, compound L is then coupled with piperazine derivative $D^a$

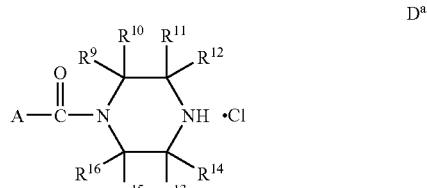

employing a molar ratio of $D^a$:L within the range from about 1.3:1 to about 1.1:1, preferably from about 1.22:1 to about 1.1:1, an organic base such as sodium t-butoxide, potassium t-butoxide or lithium t-butoxide (molar ratio base to L within the range from about 2.5:1 to about 3.1:1) is added and the reaction is stirred at a temperature within the range from about 15 to about 22° C. and then cooled to about −5° C. to about 5° C. The compound II is formed and may be recrystallized as described hereinafter and in the examples.

The starting materials, b. and d. in Scheme II, are known in the art.

The 1,2,3-triazole derivative IIA produced as described above (where $R^{18}$ is H, $R^2$ is F, $R^3$ is H, $R^9$ to $R^{16}$ are H and A is phenyl, compound II) is in the from of Form N-1 crystals which are characterized as described above.

The crystalline N-1 form of the 1,2,3-triazole derivative II are obtained by recrystallizing or slurrying of the 1,2,3-triazole derivative II (such as the P-2 form or the P-6 form of the 1,2,3-triazole derivative II) in a suitable solvent, preferably a mixture of ethanol and water in a v/v ratio ethanol:water within the range from about 6:1 to about 1:1, preferably from about 4:1 to about 2:1. Recrystallization or slurrying in other solvents such as (1) aqueous acetonitrile or (2) acetonitrile, methanol and dichloromethane (such as where the starting material is the P-6 form) or (3) isopropyl alcohol (such as where the starting material is the P-2 form) or (4) mixtures of solvents containing dichloromethane, methanol, ethanol, isopropyl alcohol, and/or acetonitrile may also be employed to produce crystalline Form N-1 material.

The crystalline N-1 form of the 1,2,3-triazole derivative II may also be obtained by heating the P-2 form of the 1,2,3-triazole derivative II to a temperature of about 265° C. (at about 10° C./min) and cooling to room temperature.

The P-2 form of the 1,2,3-triazole derivative II may be prepared by crystallization of crude 1,2,3-triazole derivative II with methanol or by crystallization of crude 1,2,3-triazole derivative II with methanol followed by chomatography on silica gel using hexane/ethyl acetate/trichloromethane and methanol.

The P-6 form of the 1,2,3-triazole derivative II may be prepared by the crystallization of the crude 1,2,3-triazole derivative II with methanol followed by chomatography of silica gel using hexane/ethyl acetate/dichloromethane/methanol.

The crystalline N-1 Form of the 1,2,3-triazole derivative II may be converted to a preferred stabilized amorphous form which may be prepared in accordance with the present invention by flash evaporation or spray drying or any other techniques thereof.

In accordance with the present invention, stabilized amorphous form of the 1,2,3-triazole derivative II is prepared by solubilizing or slurrying or suspending a mixture of Form N-1 and stabilizer in an appropriate solvent system, heating the resulting mixture to a temperature to effect solubilization and subjecting the resulting solution to flash evaporation to form the desired stabilized amorphous form of the 1,2,3-triazole derivative II.

The resulting stabilized amorphous form of the 1,2,3-triazole derivative II will have improved solubility over the starting Form N-1 and will have improved oral bioavailability. The stabilizer employed in forming the stabilized amorphous form of the 1,2,3-triazole derivative II will function to inhibit conversion of the amorphous form back to the crystalline N-1 form. Examples of stabilizers suitable for use herein include but are not limited to polyvinylpyrrolidone (PVP), PVP-vinyl acetate copolymer, or PVP-vinyl acetate copolymer and d-α-tocopheryl polyethylene glycol 1000 succinate (TPGS). However, the amorphous 1,2,3-triazole derivative II may be stabilized by other excipients such as hydroxypropyl cellulose (HPC), hydroxypropyl methyl cellulose (HPMC) or any other pharmaceutically acceptable excipients.

The compounds prepared by the processes of the invention and the N-1 and amorphous forms of the 1,2,3-triazole derivative II may be administered orally, parenterally (including subcutaneous injections, intravenous, intramuscular, intrasternal injection or infusion techniques), by inhalation spray, or rectally, in dosage unit formulations containing conventional non-toxic pharmaceutically-acceptable carriers, adjuvants and vehicles.

Thus, in accordance with the present invention, there is further provided a method of treating and a pharmaceutical composition for treating viral infections such as HIV infection and AIDS. The treatment involves administering to a patient in need of such treatment a pharmaceutical composition which includes a pharmaceutical carrier and a therapeutically-effective amount of a compound of Form N-1 or amorphous form of the 1,2,3-triazole derivative II.

The pharmaceutical composition may be in the form of orally-administrable suspensions, solutions, capsules or tablets; nasal sprays, sterile injectable preparations, for example, as sterile injectable aqueous or oleagenous suspensions or suppositories.

When administered orally as a suspension, these compositions are prepared according to techniques well-known in the art of pharmaceutical formulation and may contain microcrystalline cellulose for imparting bulk, alginic acid or sodium alginate as a suspending agent, methylcellulose as a viscosity enhancer, and sweetners/flavoring agents known in the art. As immediate release capsules/tablets, these compositions may contain microcrystalline cellulose, dicalcium phosphate, starch, calcium carbonate, magnesium stearate and lactose and/or other excipients, binders, surfactants, extenders, disintegrants, diluents and lubricants known in the art.

A vehicle for an oral solution is set out below:

(1) 75% (w/w) Polyethylene Glycol 400 (PEG 400)

(2) 10% (w/w) d-alpha Tocopheryl Polyethylene Glycol 1000-Succinate (TPGS)

(3) 15% (w/w) Ethyl Alcohol

The injectable solutions or suspensions may be formulated according to known art, using suitable non-toxic, parenterally-acceptable diluents or solvents, such as mannitol, 1,3-butanediol, water, Ringer's solution or isotonic sodium chloride solution, or suitable dispersing or wetting and suspending agents, such as sterile, bland, fixed oils, including synthetic mono- or diglycerides, and fatty acids, including oleic acid.

The compounds prepared by the processes of the invention (including the 1,2,4-triazole derivatives IA and the 1,2,3-triazole derivatives IIA) and the N-1 and amorphous forms of the 1,2,3-triazole derivative II can be administered orally to humans in a dosage range of 1 to 100 mg/kg body weight in divided doses. One preferred dosage range is 1 to 10 mg/kg body weight orally in divided doses. Another preferred dosage range is 1 to 20 mg/kg body weight orally in divided doses. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The invention is intended to cover isomers, diasteroisomers, stereoisomers, and enantiomers of the depicted formulas when one or more asymmetric carbons are present in the molecules. An asymmetric carbon is one in which the carbon is attached to four different substitutions. In particular, the invention is intended to cover isomers or a single enantiomer especially when one enantiomer displays superior properties. Enantiomers differ from one another in that the spacial arrangement of the substituents around the chiral centers of the asymmetric carbons result in each molecule being a non-superimposable mirror image of the other. In this application, the configuration of the substituents around an asymmetric carbon are defined unambiguously as either (R) which is a standard representation which stands for Latin rectus, right or (S) which is the standard representation for Latin sinister, left in the Cahn-Ingold-Prelog nomenclature system which has been in use since the 1960s. Standard rules for defining the configuration of these centers are found in any basic organic chemistry textbook. In particular, for this application and based on initial examples, when $D^a$ contains a single methyl group, when the carbon bearing the methyl group is in the (R) configuration it may show a potency advantage over the (S) enantiomer. Occasionally the (R)-methyl piperazine may show a potency advantage over the unsubstituted piperazine. These observations are compound specific effect and are not always present. The unsubstituted piperazine and (S) enantiomers are still potent antiviral compounds despite occasionally being less potent than the (R) enantiomer.

The effective treatment of HIV and other viruses requires compounds that are potent inhibitors of the virus, are selective for the virus, and have the properties which allow them to safely achieve and maintain plasma level concentrations which are a maximum number multiples above the concentration required to minimally inhibit the virus. Higher exposures suppress viral replication and reduced rates of replication mean that strains of virus with resistance to the drug treatment will develop at a slower rate. Potent drugs exhibit equivalent activity from a lower concentration or lower dose than that needed to achieve the same effect from a less potent drug. Drugs which intrinsically produce higher exposures from an equivalent dose in animal models or patients (as determined by pharmacokinetic measurements such as AUC, the sum of the concentration of drug in blood or plasma over a particular time, Cmax, or Cmin) will also provide greater benefit to the patient. Drugs which have higher stability in the presence of metabolizing pathways and enzymes will maintain their concentrations longer and thus require less frequent dosing or dosing of smaller quantities. In animals or people the rate of clearance is a frequently measured parameter to assess this property but mean retention time is also used. For accuracy, the determined measure of viral inhibition is an EC50; but the minimum plasma concentrations which should be maintained in a patient is generally believed to be at least four or five fold higher. Thus the antiviral or anti HIV drug candidates which will be most likely to provide maximum benefits in patients and those that preclinical research programs strive to identify will exhibit 1) maximum potency 2) no general cytotoxicity vs the cell line used for the assay 3) low predicted rates of metabolism in human based on in vitro models 4) high exposure after oral dosing. Many other properties of potential drug candidates are evaluated in order to determine which compounds will have the best chance of showing optimal utility in human patients but the compounds of this invention were evaluated initially in part by determining:

1) Potency vs HIV as determined by an EC50 in an initial pseudotype assay as described in the biology section.

2) Lack of general cytotoxicity vs a Hela cell line. >100 uM was used as an arbitrary cut off for safety.

3) Measurement of the rate of metabolism vs human liver microsomal preparations and from this data projecting human rate of clearance. Lower is better.

4) Estimating potential exposure in man by measuring parameters such as AUC and rate of clearance by oral and iv dosing in rats. High exposure and low clearance was desired.

Azaindoleoxoacetic piperazine amides have been disclosed in the following series of patent applications. The first series discloses azaindole derivatives which have promising potential as antiviral agents (hereinafter called, reference 94) Wang, Tao et al, U.S. Pat. No. 6,476,034 and WO 0162255 A1, filed Jan. 19, 2001, published Aug. 30, 2001. The second series (hereinafter called, reference 106) Wang, Tao, et al discloses HIV Antiviral Activity of Substituted Azaindoleoxoacetic piperazine Derivatives in U.S. patent application Ser. No. 10/214,982 filed Aug. 7, 2002, which is a continuation-in-part application of U.S. patent application Ser. No. 10/038,306 filed Jan. 2, 2002 (corresponding to PCT Int. Appl. (PCT/US02/00455), WO 02/062423 A1, filed Jan. 2, 2002, published Aug. 15, 2002. The third series discloses azaindoleoxoacetic piperazine derivatives including compounds IA and/or IIA disclosed herein in U.S. patent application Ser. No. 10/969,675 filed Oct. 20, 2004 and in U.S. Provisional Application No. 60/626,148 filed Nov. 9, 2004. All of the references for these thee series are incorporated by reference herein.

The following Examples are illustrative of the present invention.

EXAMPLES

Example 1

Preparation of Compound A' from Compound a

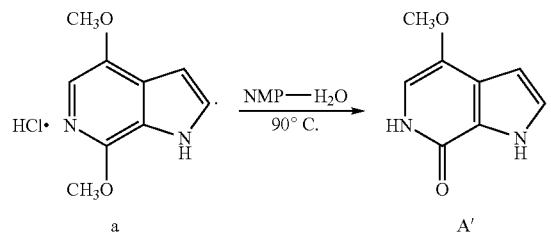

A mixture of Compound a. (hydrochloride) (60.00 g, 0.279 mol) in 1-methyl-2-pyrrolidinone (NMP) (240 mL) and water (12 mL) was heated with stirring to 90° C. under argon for 2 h. To the resulting solution was slowly added (over 40 min.) water (960 mL), resulting in crystallization of the product. The slurry was slowly cooled further to 5° C. and held overnight. The cold slurry was filtered, the cake was washed with cold (0-5° C.) water (240 mL), and dried in vacuo at 50° C. for 16 h affording 41.28 g of Compound A' as a light beige solid (89.9%) with 99.6% purity (hplc). $^1$H NMR (500 MHz, d$_6$-DMSO) δ 3.70 (s, 3H), 6.32 (dd, 1H, J=2.4 Hz), 6.37 (d, 1H, J=4.8 Hz), 7.24 (dd, 1H, J=2.8 Hz), 10.46 (bs, 1H), 12.01 (bs, 1H).

Anal. Calcd for $C_8H_8N_2O_2$: C, 58.53; H, 4.91; N, 17.06. Found: C, 58.48; H, 4.82; N, 17.12.

Example 1A

Preparation of Example 1 Starting Material

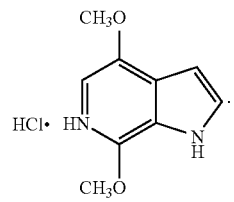
(Compound a)

Part A:

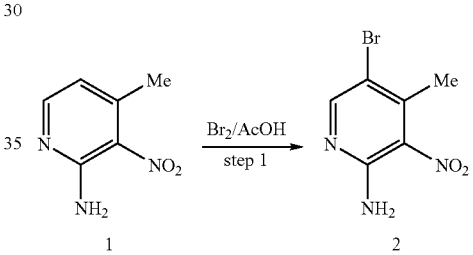

A reaction vessel was purged with inert gas. All steps were performed under inert gas protection.

The vessel was then charged with 7.50 L of acetic acid at 20-25° C. Next, 1.00 kg of the compound of formula 1 was added to the vessel. A yellow suspension was formed. This was followed by the addition of 1.07 kg of sodium acetate. A very thick, yellow suspension was formed and the reaction was noted to be slightly exothermic. The temperature was raised to about 27° C.

The mixture was then cooled to about 15-20° C. and a sample was taken for high pressure liquid chomatography (HPLC) monitoring.

A solution of 1.15 kg of bromine (1.1 eq.) and 2.5 L of acetic acid was prepared. A 10/11 portion of the solution, i.e., 1.0 eq. at 15-20° C. was added to the vessel over about 10-15 minutes. The addition was slightly exothermic and some cooling was necessary (T$_{max}$=20° C.). HPLC was used to monitor the reactions progress immediately after the addition and then at 60 min. Less than 10% of the starting material was observed. Then the remainder of the solution was added and the reaction mixture stirred until completion, approximately 30-60 additional minutes.

After the reaction was complete 10.0 L of ice water was added, dropping the temperature to 10° C. and forming a suspension. The suspension was stirred for another 30-60 minutes and the product was filtered, then washed with 3×2.50 L of ice water. The product was dried at 40° C. to a constant LOD. The yield was 1.45 kg (96%), yellow crystals. mp. 132° C. IR (KBr, cm$^{-1}$): 1633, 1581, 1538, 1512, 1458, 1377, 1344, 1321, 1244, 869, 779. $^1$H-NMR (CDCl$_3$) (δ, ppm): 2.55 (s, 3H), 5.85 (bs, 2H), 8.25 (s, 1H): $^{13}$C-NMR (CDCl$_3$) (δ, ppm): 20.81, 112.14, 144.49, 151.91, 153.78 (2C); MS; (M+1): 232; Elemental Analysis: calcd for C$_6$H$_6$BrN$_3$O$_2$: C, 31.05; H, 2.60; N, 18.11; Br, 34.43; found: C, 30.95; H, 2.42; N, 17.45; Br, 34.80.

Part B:

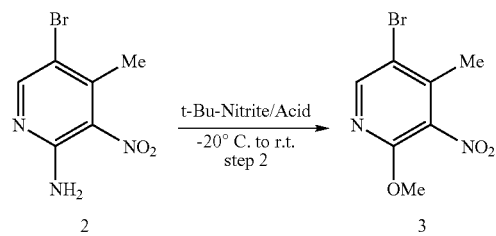

This reaction was conducted under inert gas protection.

The reaction vessel was first charged with 2000 mL methanol and cooled to about 0° C. with slight agitation. Then 9.1 kg acetyl chloride was added. The exothermic reaction was then cooled and agitated for 10 minutes.

The next addition was 100 g of 2-amino-5-bromo-3-nitro-4-picoline (the compound of formula 2) at 0° C. Then 236.5 g of t-butyl nitrite was added at a rate such that the temperature did not exceed 5° C. The slight evolution of nitrogen gas was noted. After the completion of the reaction, cooling was removed and the reaction mixture within the vessel was allowed to warm to 25° C. in about 30 minutes.

The mixture was agitated at 25° C. for about 3-4 hours. After 4-5 hours a clear solution was obtained. Reaction completeness was monitored by HPLC after about 4 hours. The reaction was complete after about 5 hours.

The reaction mixture was concentrated in vacuo to about 1000 mL. Then 500 mL of water was added and the product precipitated. Then 250 mL saturated sodium bicarbonate solution was added with good agitation to neutralize the HCl and dissolve the hydroxy impurity. The mixture was agitated at 20-25° C. for about 15 minutes and then the precipitate was collected and washed with 1000 mL of water. The product was then dried at 40° C. in vacuo. Yield was 75.0 g (70.44%), mp. 132° C. IR (KBr, cm$^{-1}$): 1633, 1581, 1538, 1512, 1458, 1377, 1344, 1321, 1244, 869, 779. $^1$H-NMR (DMSO-d$_6$) (δ, ppm): 2.31 (s, 3H), 3.96 (s, 3H), 8.55 (s, 1H): $^{13}$C-NMR (DMSO-d6) (δ, ppm): 17.49, 54.91, 99.41, 114.39, 141.02, 149.23, 153.46; HMS calcd for C$_7$H$_7$BrN$_2$O$_3$ 245.96401 found (M+1): 246.97184; Elemental Analysis: calcd for C$_7$H$_7$BrN$_2$O$_3$: C, 34.03; H, 2.85; N, 11.34; found: C, 33.81; H, 2.91; N, 11.24.

Part C:

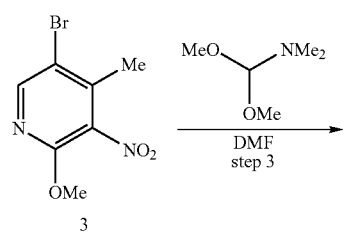

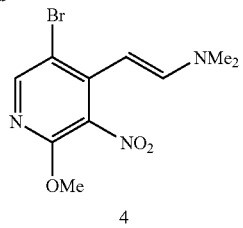

The reaction vessel was purged with inert gas and all steps were performed under inert gas protection.

The vessel was charged with 100 g of the compound of formula 3. Then 800 mL of dimethyl formamide (DMF) was added followed by 39.5 mL of 1.0 M solution of LiOMe in MeOH (32.25 g, 0.0395 mmol). The reaction was heated to 80° C.

The next addition to the vessel was 430.17 mL N,N-dimethyl formamide-dimethyl acetal (3.23 mmol, 8 eq.) over 10 minutes. An endothermic reaction was noted. The reaction was heated to 95° C. and completed in about 8-10 hours as confirmed by HPLC. After the reaction was complete, it was cooled to room temperature. 1200 mL water was added, while maintaining the temperature of the reaction mixture above about 40° C.

A red solid precipitated which was filtered and then washed with two 300 mL portions of water. The product was dried to obtain the compound of formula 4. Karl Fischer (KF) titration revealed the water content to be about 0.08-0.11%. mp. 132° C. IR (KBr, cm$^{-1}$): 1629, 1582, 1487, 1407, 1309, 1081. $^1$H-NMR (CDCl$_3$) (δ, ppm): 2.92 (s, 6H), 3.94 (s, 3H), 4.92(d, 1H), 7.0 (d, 1H), 8.15 (s, 1H): $^{13}$C-NMR (CDCl$_3$) (δ, ppm): 54.79, 87.94, 112.08, 140.15, 147.59, 148.57, 155.03; MS calcd for C$_{10}$H$_{12}$BrN$_3$O$_3$ 301.01 found (M+1): 302.0.

Part D:

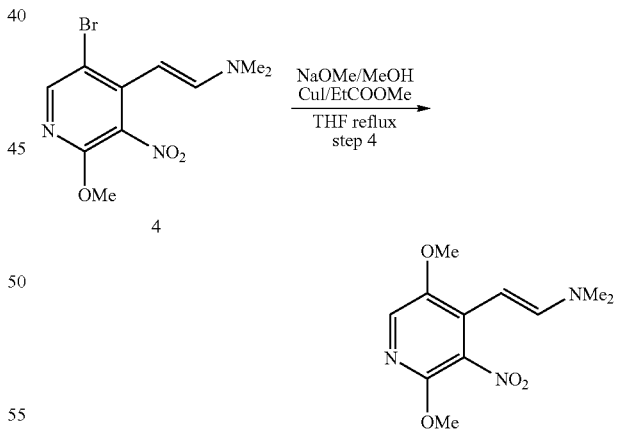

The reaction vessel was purged with inert gas and then charged with 250 g (0.827) of the compound of formula 4, then 31.52 g CuI (0.165 mol, 0.2 eq.), 875 mL methyl propionate (about 9.102 mol, 11 eq.), 875 mL tetrahydrofuran (about 10.787 mol, 13 eq.), and 2838 mL NaOMe (25% in MeOH)(12.412 mol, 15 eq.). There was a 6° C. exotherm during the course of the addition. The reaction was heated to reflux (about 69-71° C.) until the reaction was complete (about 20 hours).

The reaction mixture was cooled to around 5° C. Then the vessel was charged with 4960 mL of 3.7 M NH₄Cl (aq.) (about 3.5-3.9M). There was a 3° C. exotherm during the course of the addition with a concomitant pH change from 13-13.5 to about 9.2-9.7.

The reaction mixture was filtered to collect the precipitate. The product was then washed until the washings were free of halide (AgNO₃ test negative). The product was then dried under vacuum at 50° C. until KF<0.1% obtaining 165.3 g of the compound of formula 5. mp. 167~168° C. IR (KBr, cm⁻¹): 1629, 1582, 1487, 1408, 1309, 1081. ¹H-NMR (DMSO-d₆) (δ, ppm): 2.87 (s, 6H), 3.82 (s, 3H), 3.89 (s, 3H), 4.51 (d, 1.2 Hz, 1H), 7.74 (s, 1H), 7.83 (d, 1.5 Hz, 1H). ¹³C-NMR (DMSO-d₆) (δ, ppm): 53.6, 56.8, 82.2, 128.6, 130.2, 131.2, 146.6, 148.9, 150.3. H-MS: calcd for C₁₁H₁₆N₃O₄ (M+H⁺): 254.1141; found: 254.1138. Elemental Analysis: calcd for C₁₁H₁₅N₃O₄: C, 52.16; H, 5.97; N, 16.59; found: C, 51.91; H, 5.73; N, 16.43.

Part E:

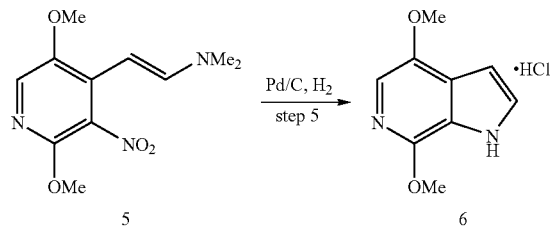

The compound of formula 5 (15 g) was charged into a 1 L glass buchii hydrogenation reactor followed by 1.5 g of Escat-261 (1% Pt/C, ~59% wet), 300 mL of ethyl acetate, and the reactor was purged thee times with nitrogen (25 PSI each). The first purge was without stirring, followed by second and third with 100-200 rpm stirring. Then the reactor was purged thee times, while stirring with hydrogen gas and the reactor was pressurized at 25 PSI with hydrogen at 25° C. internal temperature.

The reaction RPM was set to 800 and the hydrogen uptake was followed. The reaction was stopped when the hydrogen uptake stabilized after which time in process HPLC indicated reaction completion. The catalyst was filtered off and the solids washed with 10 mL ethyl acetate. The rich ethyl acetate streams were combined and 150 mL water was added followed by addition of 7.1 mL of acetic acid. The mixture was agitated for 0.5 h. Agitation was stopped and layers allowed to separate. The lower spent aqueous stream was drawn off for futher processing. The rich organic stream was washed with an additional 2×150 mL of deionized water. The spent aqueous streams were combined and back extracted with 50 mL ethyl acetate. The organic streams were combined and 16 mL isopropanol (IPA) was added followed by 7.7 mL of TMSCl added dropwise at room temperature over a ten minute period. The resulting slurry was stirred for one hour at 20-22° C. The crystals were collected via filtration, washed with 2×20 mL ethyl acetate, deliquored for 0.5 h and dried under vacuum at 40° C. for 15 h to yield 11.1 g (87.2%), white solids, mp. 294.81° C. IR (KBr, cm⁻¹): 1629, 1582, 1487, 1408, 1309, 1081. ¹H-NMR (DMSO-d₆) (δ, ppm): 3.90 (s, 3H), 4.20 (s, 3H), 6.58 (bs, 1H), 7.12 (s, 1H), 7.74 (bs, 1H). ¹³C-NMR (DMSO-d₆) (δ, ppm): 56.41, 58.06, 100.83, 107.13, 107.17, 119.84, 128.61, 132.20, 145.61, 145.75. MS: calcd for C₉H₁₀N₂O₂: 178.07; found: 179 (M+1).

Example 2

Preparation of Compound B' from Compound A' (Example 1)

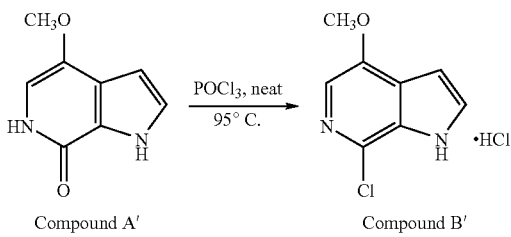

Compound A' (117.4 g, 0.715 mol) was added in portions to POCl₃ (1520 mL, 16.307 mol) under argon keeping the temperature at about 24° C. in a 3000 mL flask equipped with a mechanical stirrer. The resulting slurry was heated at 95° C. for 27 h then cooled and stirred at 0° C. for about 1 h. The cold slurry was filtered, the cake was washed with EtOAc (3×200 mL)), and dried in vacuo at 30° C. for 20 h giving 210.7 g Compound B' (HPO₂Cl₂ salt) as a white solid. The solid was added in portions to preheated (45° C.) MeOH (250 mL) so as to control the exotherm at 50-60° C. To the resulting clear solution, was added EtOAc (415 mL) slowly, while maintaining the temperature at 45-55° C. wtih gentle heating. The solution was allowed to cool slowly to 21° C., resulting in crystallization of the product. The slurry was slowly cooled further to 5° C. and held overnight. The cold slurry was filtered, the cake was washed with cold (5° C.) EtOAc (3×100 mL), and dried in vacuo at 40° C. for 20 h affording 111.0 g Compound B' (hydrochloride) as a white solid (70.8%) with HPLC AP 99.3. KF 5.49%; ¹H NMR (400 MHz, CDCl₃): δ 4.05 (s, 3H), 6.92 (dd, 1H, J=2.9, 1.9 Hz), 7.62 (s, 1H), 7.96 (dd, 1H, J=2.9, 2.9 Hz), 13.10 (bs, 1H). Anal. Calcd for C₈H₈Cl₂N₂O.0.7H₂O: C, 41.46; H, 4.09; Cl, 30.59; N, 12.09. Found: C, 41.60; H, 3.89; Cl, 30.72; N, 12.06.

Example 3

Preparation of 3-Methyl-1,2,4-triazole

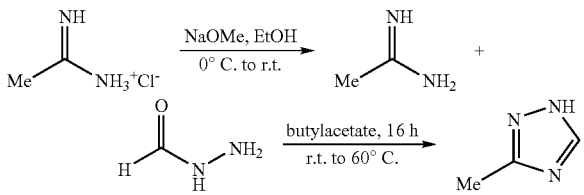

To a 20-L reactor equipped with a temperature probe and an overhead stirrer, was added acetamidine hydrochloride (2.0 kg, 21.16 mol) and absolute ethanol (10.0 L). The resulting slurry was cooled to 0-5° C. Sodium methoxide (1.15 kg, 21.2 mol) was added to the reactor with stirring while maintaining the batch temperature below 20° C. Subsequently, formic hydrazine (1.28 kg, 21.2 mol) was added to the reaction mixture. The resulting slurry was continuously stirred and heated to 55° C. over a period of 1 h and was allowed to agitate at 55° C. degree for 16 h. Then the reaction mixture was cooled to 20° C. and solids were filtered off. The filtrate was transferred back to the reactor and concentrated to ~2.0-2.5 L though distillation under reduced pressure. To this concentrated ethanol solution, was charged butyl acetate (4 L) at room temperature. The resulting solution was concentrated to ~2.0-2.5 L by distillation under reduced pressure. To this concentrated solution, was added additional butyl acetate (4.0 L) at room temperature and GC analysis of the solution was conducted. The above solvent exchange process was repeated until butyl acetate/ethanol wt/wt % is greater than 19 by GC analysis. After the completion of solvent exchange process, the batch was heated to 70-75° C. and held for 15 min. Then the rich organic solution was cooled to ambient temperature (20-22° C.) over a 1 h period and was agitated at that temperature for 14 hours. The resulting slurry was cooled to 0-5° C. and agitated at that temperature for additional 1 hour. The crystals were collected by filtration. The cake was washed with 4.0 L of a mixture of heptane:butyl acetate (v/v: 3:1). The wet cake was de-liquored for 1 hour, and dried under vacuum (25 mmHg) at 30-35° C. for 48 h. 3-Methyl-1,2,4-triazole (1.59 kg, 19.1 mol) was obtained in 90.3% yield as a light pink solids. $^1$H NMR (300 MHz) δ 2.53 (s, 3H), 8.03 (s, 1H), 11.52 (s, 1H); $^{13}$C NMR (300 MHz) δ 156.5, 149.8, 13.5. Anal. Calc. for $C_3H_5N_3$: C, 43.36; H, 6.06; N, 50.57. Found: C, 43.29; H, 6.15; N, 50.54

Example 4

Preparation of Compound C' from Compound B' (Example 2)

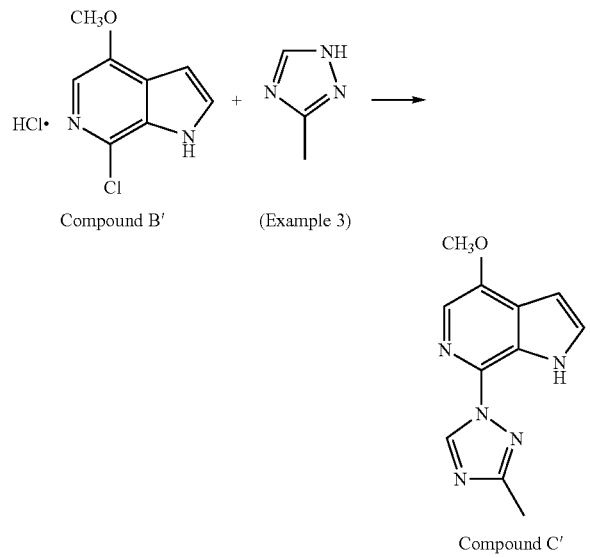

Compound B'  (Example 3)

Compound C'

Compound B' (60.00 g, 0.274 mol) (prepared as in Example 2) was added in portions to a melt of 3-methyl-1,2,4-triazole (113.8 g, 1.369 mol) under argon at 110-120° C. The mixture was heated to about 143° C. and the resulting solution was stirred at 142-44° C. for 17 h. After cooling to 120° C., 1-methyl-2-pyrrolidinone (NMP) (60 mL) was added quickly. The solution was further cooled to about 95° C. and water (300 mL) was added slowly (about 30 min.) keeping the temperature at 85 and 95° C. resulting in crystallization of the product. The slurry was cooled slowly to 0-5° C. and held for about 1 h. The cold slurry was filtered and the cake washed with cold $H_2O$ (2×75 mL) then dried in vacuo at 55° C. for 16 h affording 34.5 g Compound C' as a crystalline, tan solid (54.9%), HPLC AP 98.2. If necessary, the product could be further purified by recrystallization from ethyl acetate. $^1$H NMR (400 MHz, CDCl3) δ 2.55 (s, 3H), 4.05 (s, 3H), 6.73 (dd, 1H, J=2.9, 2.6), 7.42 (dd, 1H, J=2.9, 2.8), 7.57 (s, 1H), 9.16 (s, 1H), 10.29 (bs, 1H). Anal. Calcd for $C_{11}H_{11}N_5O$: C, 57.63; H, 4.84; N, 30.55. Found: C, 57.37; H, 4.74; N, 30.79.

Example 5

Preparation of Compound D' from Compound C' (Example 4)

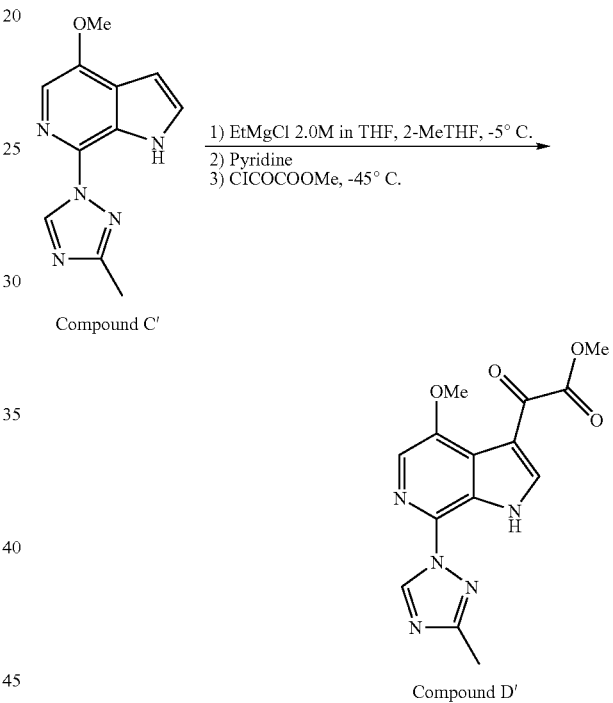

A mixture of Compound C' (65.4 mmoles) and 2-methyl THF (600 mL) is cooled to −10° C. EtMgCl 2.0M/THF (3.5 eq) is added dropwise at −10° C., followed by the addition of pyridine (0.5 eq). The slurry is cooled further to −45° C. and the acid chloride (4.0 eq) is added dropwise at −45° C. The slurry is allowed to warm to −10° C. and stirred 1 hour at this temperature. The suspension is then quenched with IPA (30 mL) and water (375 mL) and stirred overnight at r.t. The solid is collected by vacuum filtration and washed with water and IPA. The desired compound D' is dried in vacuo at 50-60° C. to afford 15.4 g (74.4% yield) of a white solid, HPLC AP 99.7. $^1$H-NMR (CDCl$_3$) (δ, ppm): 2.61 (s, 3H), 3.99 (s, 3H), 4.08 (s, 3H), 7.79 (s, 1H), 8.38 (s, 1H), 9.18 (s, 1H), 11.01 (s, 1H): $^{13}$C-NMR (DMSO-d6) (δ, ppm): 14.66, 53.55, 57.58, 113.99, 121.64, 123.95, 124.25, 130.58, 139.11, 142.99, 149.76, 162.31, 165.50, 182.23; Elemental Analysis: calcd for $C_{14}H_{13}N_5O_4$: C, 53.43; H, 4.15; N, 22.21; found: C, 53.51; H, 3.99; N, 21.96.

Example 6

Preparation of Compound I from Compound D' (Example 5)

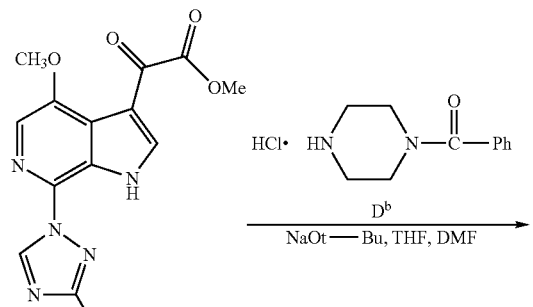

Compound D'

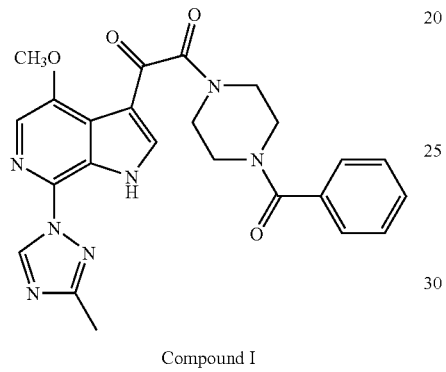

Compound I

N-Benzoylpiperazine HCl, Compound D$^b$, (11.73 g, 51.74 mmol) was added to a mixture of Compound D' (14.83 g, 47.03 mmol) (prepared in Example 5) in dry THF (265 mL) and dry DMF (29.5 mL). NaOt-Bu, 30% w/w (52.3 mL, 147 mmol) was added dropwise (30 min.) keeping the temperature at 17-21° C. The resulting yellow slurry was stirred at 17-20° for 1 h more, then cooled to about 5° C. The mixture was slowly poured into cold water (90 mL) and the flask rinsed with additional water (10 mL). The pH of the resulting yellow solution was adjusted to 6-7 with slow addition (~20 min., 5-12° C.) of 1 N HCl (105 mL). The resulting slurry was warmed and stirred at room temperature for 1.5 h. The slurry was filtered and the cake washed with water (2×60 mL) then dried in vacuo at 65-70° C. for 5 h giving 18.4 g Compound I as a white solid (82.6%), HPLC AP 99.4. $^1$H NMR (400 MHz, d$_6$-DMSO): δ 2.48 (s, 3H), 3.43 (b, 4H), 3.67 (b, 4H), 3.99 (s, 3H), 7.45 (s, 5H), 7.88 (s, 1H), 8.24 (s, 1H), 9.22 (s, 1H), 12.39 (s, 1H). $^{13}$C NMR (100 MHz, d$_6$-DMSO): 13.85, 40.65, 45.22, 56.85, 114.19, 121.02, 122.78, 123.65, 127.06, 128.42, 129.61, 129.70, 135.51, 138.59, 142.18, 149.23, 161.38, 166.25, 169.30, 185.51.

If necessary, the product could be further purified by recrystallization from acetic acid-water-ethanol, ethanol-water, or acetone-water. For example: A mixture of Compound I (25.0 g), glacial acetic acid (260 mL) and DI water (13.8 mL) was heated to 80° C. and held with stirring (overhead) until a solution was obtained (40 min.). The batch was cooled to 70° C. and seeded (0.5 g). With slow agitation (100 rpm), EtOH (300 mL) was added slowly (1 h), keeping the temperature at 70° C. The resulting slurry was kept at 70° C. for 1 h more with very slow stirring. The slurry was cooled to 20° C. over 2 hours and held at 20° C. for over 4 hours. The slurry was filtered, the wet cake washed with EtOH (125 mL), and the solid dried in vacuo at 70° C. (≧16 h), giving 22.6 g Compound I as a white solid (88.4%).

Example 7

Preparation of Compound J' from Compound d$^a$

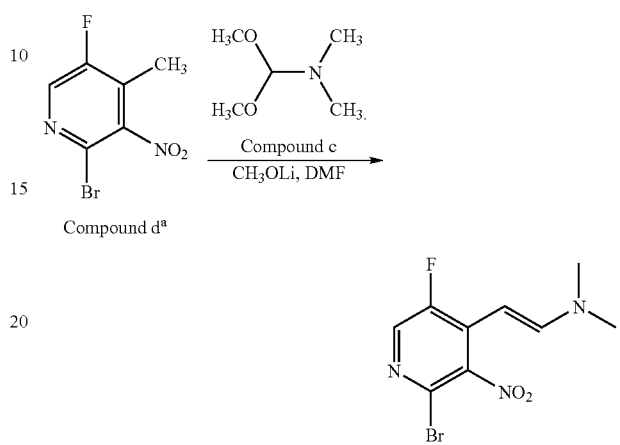

Compound d$^a$ (800 g, 3.404 mol), lithium methoxide (12.9 g, 0.34 mol) and DMF (5.6 L) was charged to an inert 20 L Korzun reactor. Then DMF-dimethyl acetal c. (2.02 kg, 17.1 mol) was added. The resulting homogeneous solution was warmed to 80-85° C. and held at this temperature until HPLC analysis of the crude reaction mixture indicated that less than 0.5 relative area percent (RAP) of compound d$^a$ remained. The reaction mixture was cooled to 5-10° C. Water (9 L) was charged to the reactor maintaining the temperature below 45° C. The resulting slurry was cooled to 0-5° C. and held at this temperature for 1 h. The crystals were collected via filtration. The cake was washed with deionized water (6 L) and dried at 45° C. under vacuum to give J' as a light brown solid (890 g, 90%, HPLC AP 98.1). $^1$H NMR (300 MHz, d$_6$-DMSO) δ 8.02 (d, J$_{F-H}$=4.2 Hz, 1H), 7.47 (dd, J=13.0 Hz, J$_{F-H}$=1.7 Hz, 1H), 4.20 (d, J=13.0 Hz, 1H), 3.14 (s, 6H); $^{13}$C NMR (75 MHz, d$_6$-DMSO): δ 153.9 (d, J$_{F-C}$=255 Hz), 151.6, 151.4, 141.9, 136.4 (d, J$_{F-C}$=27 Hz), 131.0 (d, J$_{F-C}$=15 Hz), 126.1 (d, J$_{F-C}$=2 Hz), 78.8.

Example 8

Preparation of Br,F-Azaindole, Compound K' from Compound J' (Example 7)

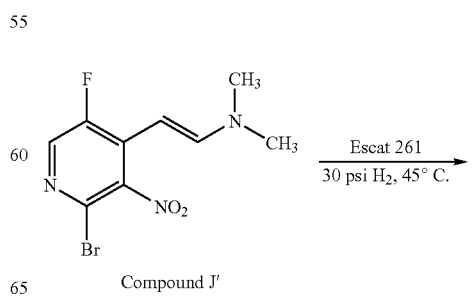

Compound J'

-continued

Compound J'

Compound J' (450 g, 1.557 mol), Escat 261 catalyst (Pt/C) (90.0 g, 20 wt % in water) and THF (3.6 L) were charged to an inerted 5-liter hydrogenation reactor. The resulting slurry was allowed to agitate at ambient temperature for 1 h. Hydrogen was added to a final pressure of 30 psi. The reactor was gently heated to 45° C. and held at this temperature until the reaction was determined to be complete by in process HPLC analysis. The catalyst was removed via filtration and the cake washed with THF (0.36 L). The solution was concentrated to minimum agitation volume via distillation under reduced pressure. Acetone was charged to the reactor to bring the total volume to 5.4 L. The acetone solution was heated just to reflux and water (3.5 L) was added maintaining the temperature between 50-55° C. The resulting slurry was cooled to 0-5° C. over a 1 h period and held at this temperature for 1 h. The crystals were collected via filtration, washed with deionized water and deliquored for 1 h. The cake was dried at 40° C. under vacuum to give K' as an off-white solid (580 g, 87% yield, HPLC AP 99.5). $^1$H NMR (300 MHz, d$_6$-DMSO) δ 7.94 (d, $J_{F-H}$=1.9 Hz, 1H), 7.75 (d, J=3.0 Hz, 1H), 6.78 (d, J=3.0 Hz, 1H); $^{13}$C NMR (75 MHz, d$_6$-DMSO) δ 153.3 (d, $J_{F-C}$=252 Hz), 133.7 (d, $J_{F-C}$=9 Hz), 131.1, 123.6 (d, $J_{F-C}$=25 Hz), 122.8 (d, $J_{F-C}$=21 Hz), 119.0, 98.6; MS ES$^+$ 216.9 (M+1).

Example 9

Preparation of Compound H' from Compound K' (Example 8)

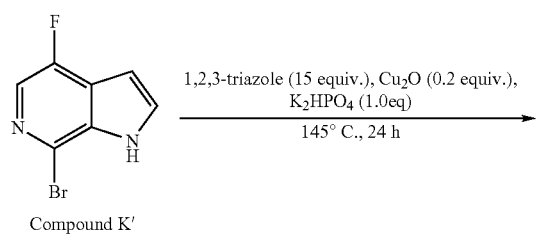

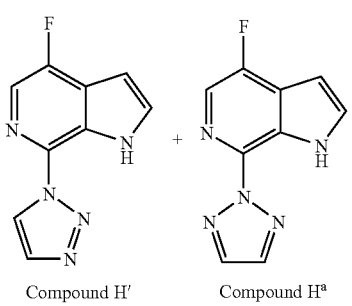

Compound K' (650 g, 3.02 mol) was charged to an inerted 12-liter reactor and followed by addition of K$_2$HPO$_4$ (527 g, 3.02 mol), Cu$_2$O (59 g, 0.60 mol) and 1,2,3-triazole (3133 g, 45.3 mol) in sequence. The mixture was agitated and heated to 145° C. under nitrogen for 24 h. The batch was cooled to 60° C. and THF (6.5 L) was charged. The batch was filtered and the filter cake was washed with THF (5.2 L). The combined THF streams were concentarted to minimum agitation volume. The batch was cooled to <30° C. and 2 N HCl (13 L) was added. The batch was aged at 20~25° C. for 20 min. with stirring and then filtered. The filter cake was washed with 2 N HCl (5.2 L) and deionized DI water. The wet cake was washed with 95% EtOH (2.6 L) and dried to produce H' as a light yellow solid (552 g, 45% yield). mp. 205~206° C.; $^1$H NMR (300 MHz, d$_6$-DMSO) δ 12.12 (s, 1H), 8.91 (s, 1H), 8.03 (s, 1H), 8.01 (d, $J_{F-H}$=1.7 Hz, 1H), 7.68 (d, J=3.2 Hz, 1H), 6.75 (d, J=3.2 Hz, 1H), 3.30 (s, 1H); $^{13}$C NMR (75 MHz, d$_6$-DMSO) δ 152.5 (d, $J_{F-C}$=252 Hz), 133.8, 132.3, 130.7, 125.2 (d, $J_{F-C}$=22 Hz), 124.4 (d, $J_{F-C}$=10 Hz), 122.3, 121.1 (d, $J_{F-C}$=26 Hz), 98.0; HMS calcd for C$_9$H$_7$FN$_5$ 204.0685, found 204.0684; Anal. Calcd for C$_9$H$_7$FN$_5$: C, 53.20; H, 2.97; N, 34.47. Found: C, 52.99; H, 2.88; N, 34.55.

Example 10

Preparation of Compound F' from Compound b$^a$

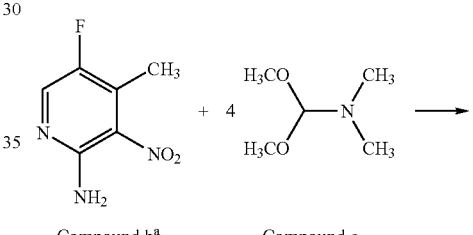

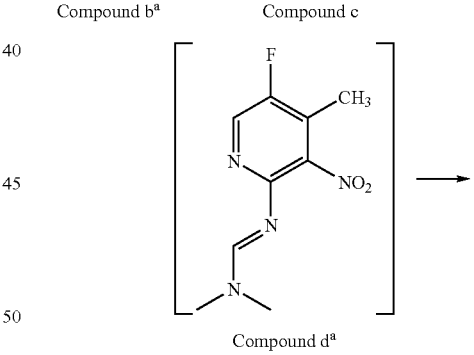

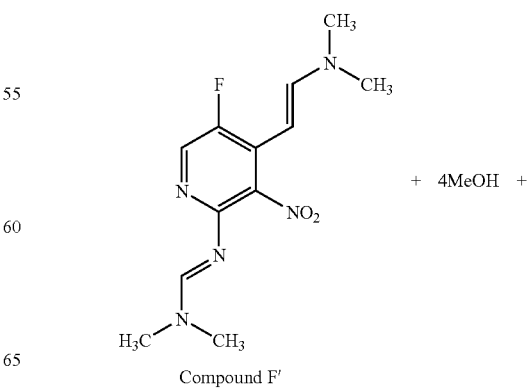

Compound F'

-continued

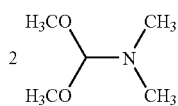

To a 2 L vessel equipped with an overhead stirrer, a Dean-Stark trap, and a temperature probe was charged 2-amino 5-fluoro 3-nitro 4-picoline (Compound b$^a$) (50.0 g, 292 mmol). DMF-DMA (Compound c) (158.5 mL, 1.17 mol, 4 eq.) was added followed by DMF (292 mL) and the mixture was heated to 120° C. After stirring at this temperature for 25 h, in process HPLC analysis of the crude reaction mixture indicated that <2 RAP of d$^a$ remained. Water (500 mL) was charged slowly, maintaining temperature <35° C. The slurry was cooled to 0-5° C. and held at this temperature for 1 h. The crystals were collected by filtartion. The filter cake was washed with water (2×250 mL). The solid product was dried in a vacuum oven (15-25 mm, 35-45° C.) to an LOD<1% (wt/wt). The solid (79.7 g, 97.0%) (Compound F') had a HPLC AP 99.6. $^1$HNMR: (500 MHz, DMSO-d$_6$) δ 8.45 (s, 1H), 8.01 (s,1H), 7.47 (d, J=13.5 Hz, 1H), 4.37 (d, J=13.5 Hz, 1H), 3.08 (s, 6H), 2.89 (s, 6H); LRMS (ESI) 282.08 [(M+Li)$^+$ calcd for C$_{12}$H$_{16}$FN$_5$O$_2$ 282.29].

Example 11

Preparation of Compound G' from Compound F' (Example 10)

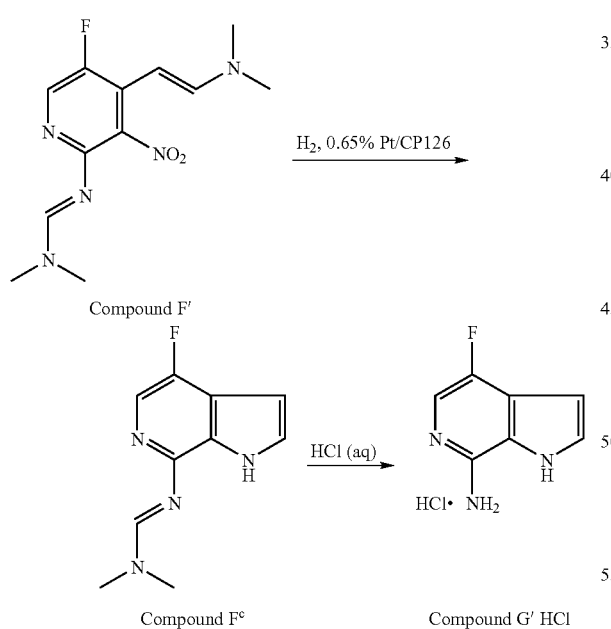

50 g (0.177 moles) of Compound F' (prepared as in Example 10) was charged to the hydrogenator followed by 7.25 g of platinum on carbon (0.65% Pt/CP126 catalyst, 1% wet). The reactor was inerted with nitrogen. 443.0 (g) (500 mL, 10 mL/g Compound F) of THF was charged to the hydrogenator. Hydrogen was charged subsurface to the reactor maintaining the temperature between 15-35° C. The reaction was determined to be complete when <1 RAP of Compound F' remains. The rich THF stream was purged with nitrogen and then filtered though a 10μ filter followed by 1μ filter to remove the platinum catalyst. The rich THF stream was transferred to the crystallizer and distilled to minimum agitation volume. 175 mL (3-3.5 L/kg Compound F' input) of 4 N HCl was charged to the crystallizer. The batch was warmed to 70-80° C. with the condenser in distillation mode to distill off the remaining THF. The batch was maintained at 70-80° C. for 15 min. and sampled for in-process HPLC analysis. The reaction was determined complete when <1 RAP of Compound F$^c$ remained. 75 mL (1.5-2 L/kg input Compound F') of water was charged to the batch while maintaining the temperature above 50° C. The batch was cooled to 0-5° C. and filtered. The mother liquor was recycled to transfer batch onto the filter. The cake was de-liquored for 1 h. The cake was dried at 45-50° C. under house vacuum to a constant LOD. The isolated yield of Compound G' HCl was 83.3% from Compound F'. Analytical data: $^1$H NMR (300 MHz, d$_6$-DMSO): δ 13.30 (s, 1H), 13.03 (br s, 1H), 8.44 (s, 2H), 7.87 (t, J=2.6 Hz, 1H), 7.60 (d, J$_{F-H}$=4.7 Hz, 1H), 6.61 (dd, J=2.6 Hz, J$_{F-H}$=2.0 Hz, 1H); $^{13}$C NMR (75 MHz, d$_6$-DMSO) δ 148.0 (d, J$_{F-C}$=237 Hz), 144.1, 134.0, 126.2 (d, J$_{F-C}$=24 Hz), 120.8 (d, J$_{F-C}$=11 Hz), 111.5 (d, J$_{F-C}$=37 Hz), 101.7. LCMS: 152 (M+1).

Example 12

Preparation of Compound H' from Compound G' HCl (Alternate Method 1)

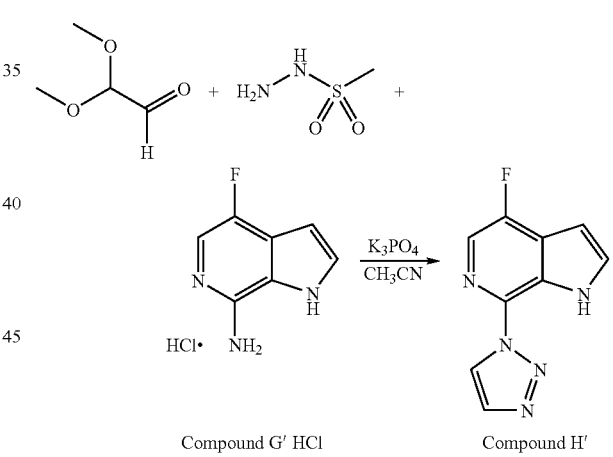

Compound G' HCl salt (20.0 g, 0.107 mol), K$_3$PO$_4$ (23.0 g, 0.111 mol), methylsulfonyl hydrazide (18.9 g, 0.138 mol) and MeCN (500 mL) were charged to a 1-liter thee-neck flask. The resulting slurry was stirred at ambient temperature for about 0.5 h. Then 2,2-Dimethoxyacetaldehyde (60% in water, 24.1 g, 0.138 mol) was added and the mixture heated to 70° C. over a 20~30 min period. After stirring at this temperature for additional 2 h, the MeCN solvent was removed via distillation at atmosphere pressure. DMA (100 mL) was charged to the flask and the mixture heated to 105° C. The batch was held at this temperature for 2 h and then cooled to below 50° C. Deionized water (200 mL) was added over a 10 min period and the resulting slurry cooled to 0-5° C. The crystals were collected via filtration. The cake was washed with deionized water (400 mL), deliquored for 1 h and dried under vacuum at 50° C. to produce H' as a yellow solid (17.4 g, 80% yield).

Example 13

Preparation of Compound G' for Use in Preparation of Compound H' from Compound G' (Alternative Method 2, Part I), as Described in Example 14

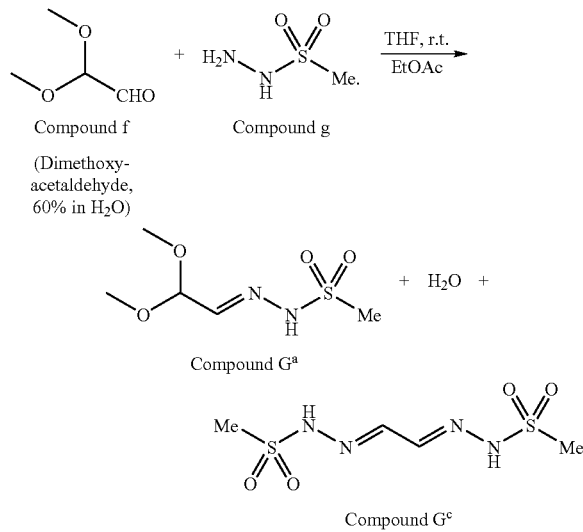

Methanesulfonohydrazide, compound g. (90.85 mmoles; 10.01 g) was charged into a 500 mL thee-neck flask, followed by tetrahydrofuran (50.0 mL) and 2,2-dimethoxyacetaldehyde, compound f (99.97 mmoles; 15.22 mL; 17.35 g). The mixture was stirred at room temperature, and the reaction was monitored with TLC (silica, EtOAc). After 3.5 h at room temperature, ethylacetate (2.13 moles; 250.00 mL; 217.80 g) was added. The solvent was distilled in a 45° C. oil bath under 80±1 mmHg vacuum to ~50 mL of residual white suspension; the internal temperature was raised from ~23° C. to ~34° C. KF of the residue was 0.463, and a crystalline suspension was obtained. Heptane (100.00 mL) was added to the suspension over ~0.5 h, which was stirred overnight. The suspension was filtered, the flask washed with the mother liquor, and the solid with heptane (2×30 mL), furnishing (E)-N'-(2,2-dimethoxyethylidene)methanesulfonohydrazide as white crystalline powder (16.2438 g, 91.1% yield). Mp 82.4° C.; decomposition, 123.8° C.; $^1$H NMR (500 MHz, d-DMSO), δ 11.01 (s, 1H), 7.16 (d, J=5.50 Hz, 1H), 4.74 (d, J=5.50 Hz, 1H), 3.31 (s, 6H), 3.00 (s, 3H); $^{13}$C NMR (125 MHz, d-DMSO), δ 145.3, 101.5, 53.3, 38.4; Elemental analysis, Calcd for $C_5H_{12}N_2O_4S$: C, 30.60; H, 6.16; N, 14.27; S, 16.34.

Found: C, 30.72; H, 6.02; N, 14.41; S, 16.08.

Example 14

Preparation of Compound H' from Compound G' (Alternative Method 2, Part II)

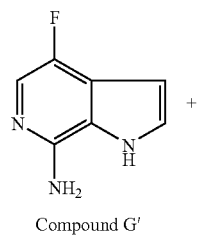

Compound G'

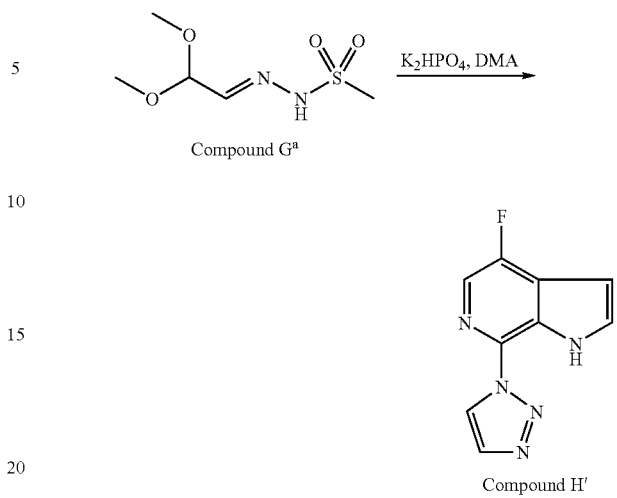

15.00 g of G (HCl salt) was neutralized with 90 mL of 1.0 N NaOH, then extracted with 200 mL of EtOAc. The EtOAc layer was washed with 2×100 mL of H$_2$O, dried with MgSO$_4$, filtered, and concentrated via roto-evaporation, giving solid G' (9.872 g). 4-Fluoro-1H-pyrrolo[2,3-c]pyridin-7-amine (G', 1.00 equiv, 65.3156 mmoles; 9.8720 g), potassium phosphate, dibasic (1.00 equiv; 65.3894 mmoles; 11.5043 g), (E)-N'-(2,2-dimethoxyethylidene)methanesulfonohydrazide (G$^a$, 1.29 equiv 84.2901 mmoles; 16.5400 g) and dimethylacetamide (100.00 mL) were added into a 250 mL flask which was degassed and purged with N$_2$. The suspension was stirred at room temperature for ~10 min. The suspension was gradually heated over ~50 min to 100° C., and the reaction monitored with HPLC. After 4 h, the reaction mixture was cooled to 20-22° C. 300 mL of H$_2$O was added, and the suspension stirred for ~0.5 h. The suspension was filtered and the solid washed with H$_2$O (3×100 mL) and dried at 50° C. under vacuum, furnishing H' as brown solid (11.5141 g, 87% yield, 99.2 AP).

Example 15

Preparation of Compound L' from Compound H' (Example 12 or 14)

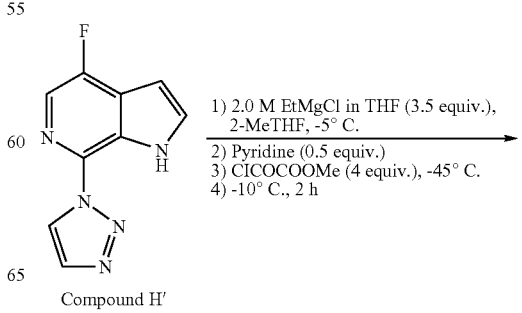

-continued

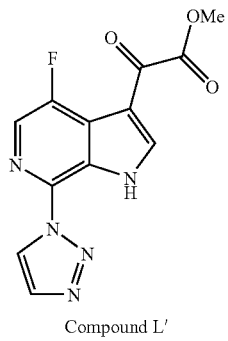

Compound L'

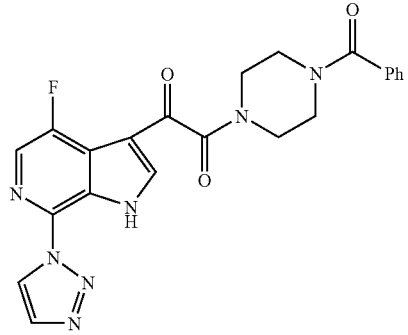

Compound II

Ethyl magnesium chloride (500 mL of a 2M solution in THF, 1000 mmol, 3.5 equiv.) was added to a solution of Compound H' (285.9 mmol) in THF (2324 mL) between −5 and −10° C. After 1 h of stirring at −10° C., pyridine (11.5 mL, 143 mmol, 0.5 equiv.) was added between −5 and −10° C. The mixture was cooled to between −40 and −50° C. and methyl chlorooxoacetate (109.5 mL, 145.9 g, 1143.6 mmol, 4 equiv.) was added between −40 and −50° C. The mixture was stirred for 1 h, warmed to −10° C. and stirred for 2 h. The mixture was quenched with methanol (116 mL, 91.9 g, 2868 mmol, 10 equiv.), followed by water (1452 g). The resulting slurry was filtered and the solids were washed with water (2×580 mL) followed by methanol (1×580 mL). The solids were dried between 35 and 45° C. under vacuum and a flow of nitrogen to a constant LOD (loss on drying) to yield 51.6 g of Compound L' (62% yield) as an off-white solid: $^1$H NMR (300 MHz, DMSO-$d_6$) δ 9.03 (d, 1H, J=1.1 Hz), 8.59 (s, 1H), 8.30 (d, 1H, J=2.3 Hz), 8.11 (d, 1H, J=1.1 Hz), 3.92 (s, 3H); $^{13}$C NMR (400 MHz, DMSO-$d_6$) δ 177.8, 163.7, 152.5 (d, J=259 Hz), 142.3, 134.3, 131.8, 126.4 (d, J=27.6 Hz), 125.8, 123.1, 122.6 (d, J=20.7 Hz), 112.5, 53.1; HMS: calcd for $C_{12}H_8FN_5O_3$ [(M+H) ion]: 290.0689, found: 290.0693.

Example 16

Preparation of Compound II from Compound L'

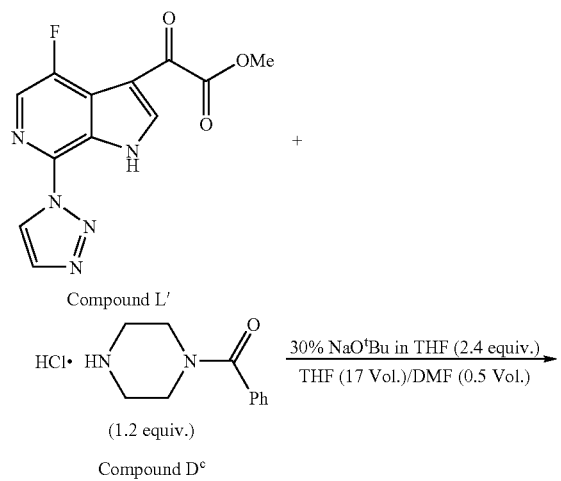

10.0 g (0.0345 mol) of compound L', 9.4 g (0.0415 mol, 1.2 mol eq based on potencies of both starting materials) of compound D$^c$, 170 mL (10 mL/g of compound L') of THF and 5.0 mL (0.5 mL/g of compound L') of DMF were charged to a 500 mL 3-necked Morton flask. The KF of the mixture was measured and 2.0 mol of trimethylorthoformate/mol of the total amount of water present in the reaction mixture was added followed by the addition of 0.53 mL (0.2 mol eq of compound L') of trifluoroacetic acid and the resulting mixture stirred at room temperature for 0.5 h. If the KF of the mixture is not below 100 PPM water an additional 1.0 mol eq of trimethylorthoformate may be added. When the KF is below 100 PPM the mixture is cooled to −10 to 0° C. 33.9 mL (30.8 g, 2.7 mol eq) of a 30 wt % solution of 97% sodium t-butoxide in THF was charged to the flask maintaining the temperature below 0° C. The reaction mixture was held at −5 to 0° C. and followed by HPLC. The reaction was determined to be complete when less than 1 relative area percent (RAP) of compound L' remained. Charge 1.0 mL of water (0.1 mL/g compound L' maintaining the temperature below 5° C. The reaction mixture was warmed to 20° C., held at this temperature for 1 h and then cooled back to 0° C. This step degrades an impurity present in the reaction mixture. Then 49 mL (1.9 mL/g compound L') of water was added maintaining the temperature below 5° C. and the resulting homogeneous solution filtered though a No. 4 Whatman filter paper. The apparent pH was adjusted to 6.3 to 6.8 with 51 mL of 1 N HCl. Water (160 mL, 16 mL/g compound L') was added. The resulting slurry containing the monohydrate form H1 of compound II was heated just to reflux (75 to 80° C.) and held at this temperature for 0.5 h and cooled to 18 to 20° C. over a 2 h period. The crystals were collected via filtration. The cake was washed with 200 mL of water followed by 50 mL of absolute ethanol, deliquored for 1 h and dried under vacuum at 50 to 55° C. to yield 12.8 g (83.0%) of a white crystalline solid. mp. 281.16. 1H NMR (300 MHz, d6-DMSO) δ 9.02 (s, 1H), 8.38 (s, 1H), 8.30 (s, 1H), 8.13 (s, 1H), 7.45 (s, 5H), 3.35-3.80 (m, 8H), 2.52 (s, 1H). 13C NMR 300 mHz, d6-DMSO δ 184.4, 169.6, 165.8, 152.5 (d, JF-C=258 Hz), 141.9. 135.8, 134.4, 131.8, 130.1, 128.8, 127.4, 126.3 (d, JF-C=28 HZ), 125.9 (d, JF-C=9 Hz), 123.2, 122.2 (d, JF-C=22 Hz), 113.4, 45.7, 41.2; HMS calcd for $C_{22}H_{18}FN_7O_3$ 448.1533, found 448.1530.

Figure 5:
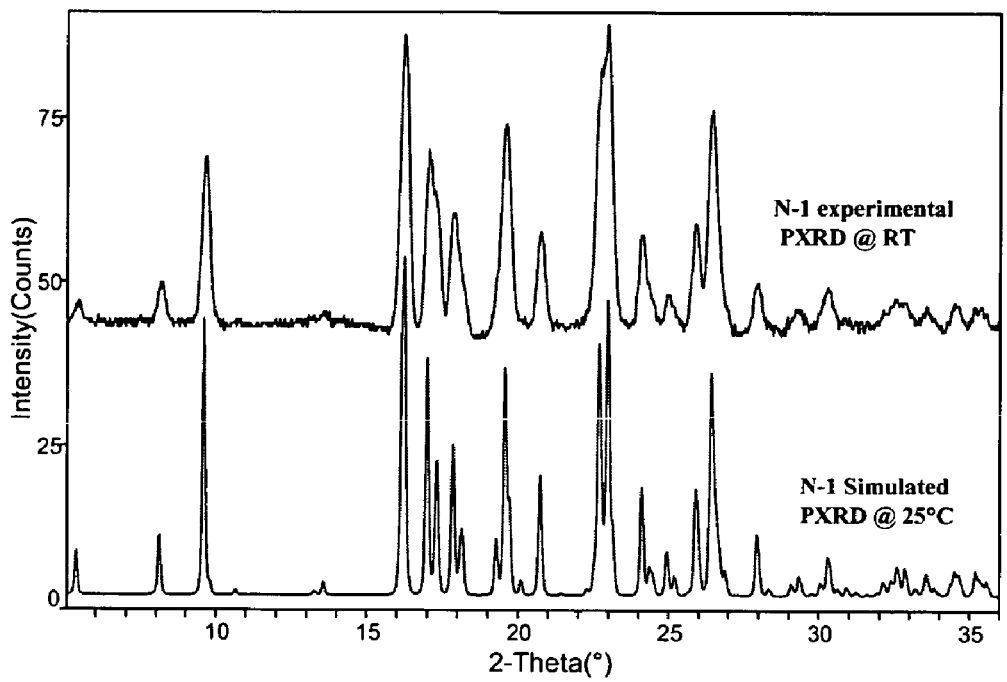
FIG. 5 shows calculated (simulated) (25° C.) and representative observed (experimental at room temperature) powder X-ray diffraction patterns (CuKα λ=1.5418 Å) of crystalline Form N-1 crystals of the 1,2,3-triazole derivative II.

The resulting crystals were identified as Form N-1 crystals of the 1,2,3-triazole derivative II. Calculated (simulated) and observed (experimental) powder X-ray diffraction patterns of Form N-1 crystals of the 1,2,3-triazole derivative II are shown in FIG. 5. The diffractogram exhibits specific peaks in the 2θ range of 5-36° including those at 2θ values (CuKα λ=1.5418 Å) 5.3±0.1, 8.1±0.1, 9.6±0.1, 16.2±0.1, 17.0±0.1, 19.6±0.1, 20.7±0.1 and 23.2±0.1.

Figure 6:
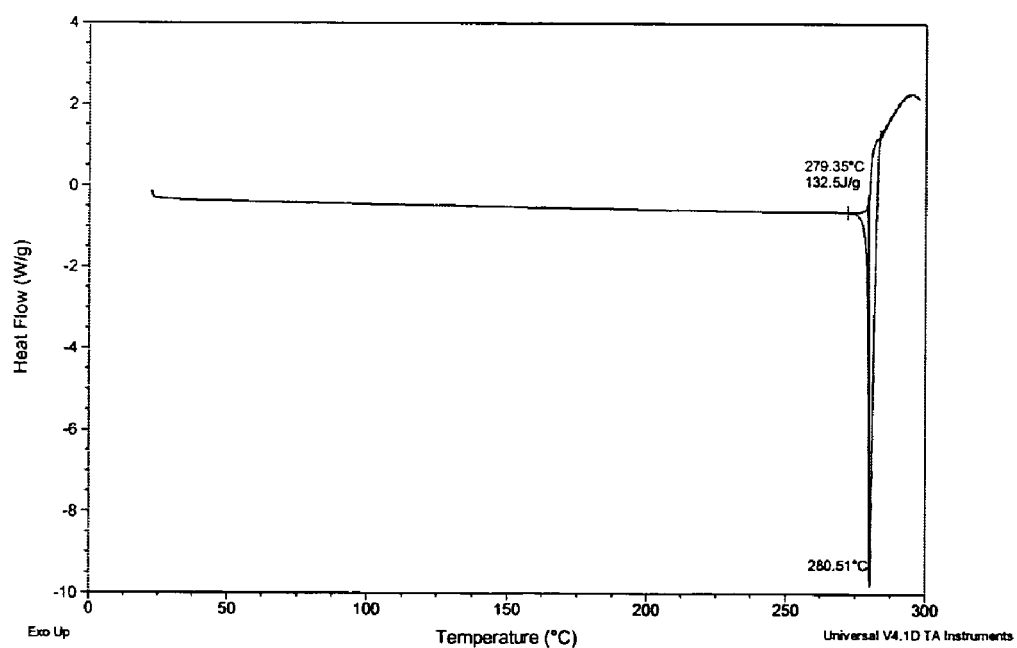
FIG. 6 shows a representative differential scanning calorimetry (DSC) thermogram of the Form N-1 crystals of the 1,2,3-triazole derivative II.
Figure 7:
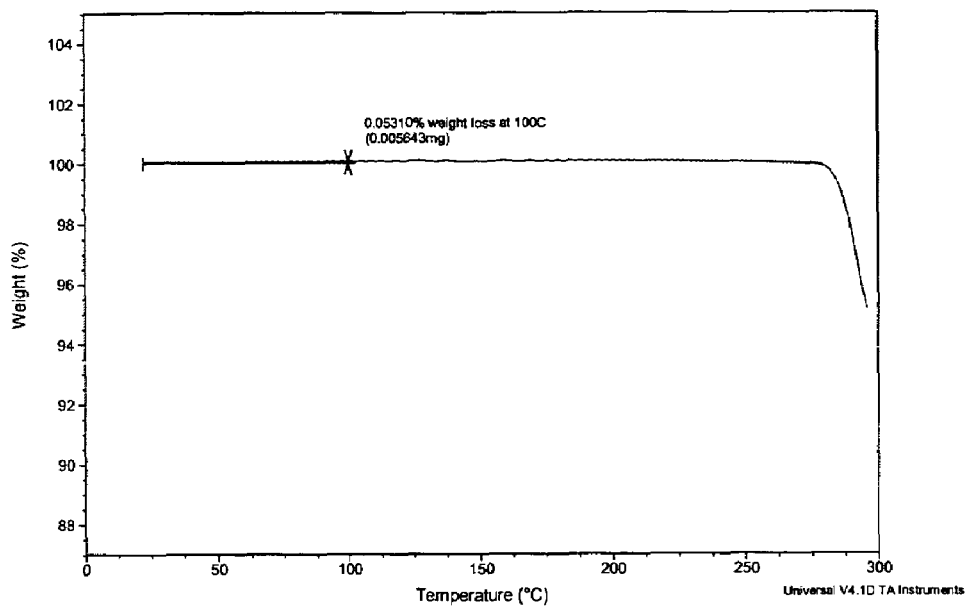
FIG. 7 shows a representative thermogravimetric analysis (TGA) curve of Form N-1 crystals of the 1,2,3-triazole derivative II.
Figure 8:
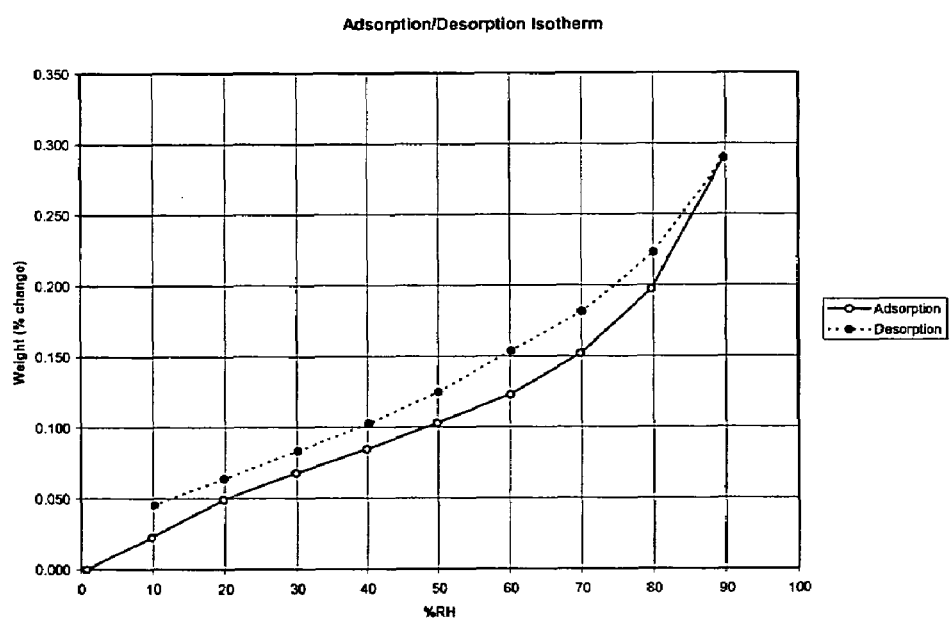
FIG. 8 shows a representative moisture-sorption isotherm of Form N-1 crystals of the 1,2,3-triazole derivative II.

The Form N-1 crystals typically exhibit a melt with decomposition with the endotherm onset at about 279° C. according to the differential scanning calorimetry (DSC) FIG. 6, and thermogravimetric analysis (TGA) (FIG. 7). TGA shows a negligible weight loss up to about 100° C., a moisture-sorption isotherm of Form N-1 crystals is shown in FIG. 8 which shows about 0.1% weight water uptake in the range from about 25% RH to about 75% RH at 25° C.

Example 16A

Preparation of N-1 Form of 1,2,3-Triazole Derivative II from the Corresponding P-6 Form Two 10 mg samples of the P-6 form of the 1,2,3-triazole derivative II were dissolved in aqueous acetonitrile and a mixture of solvents containing $CH_2Cl_2$, MeOH and acetonitrile. Clear solutions were obtained by heating. Tiny thin needles came out and were kept in the solutions at 45° C. for a few days and then at room tempearture for the crystals to grow larger. A 10 mg sample was dissolved in 0.7 mL acetonitrile and 0.7 mL MeOH. A clear solution was obtained by heating. Slow evaporation of the solution afforded large rods of crystals which were identified as the N-1 form of the 1,2,3-triazole derivative II.

The P-6 form of the 1,2,3-triazole derivative II was obtained by crystallization of the crude 1,2,3-triazole derivative II with MeOH followed by chomatography on silica gel using hexane/AcOEt/$CHCl_3$/MeOH.

Example 16B

Preparation of N-1 Form of 1,2,3-Triazole Derivative II from the Corresponding P-2 Form 4-10 mg samples of the P-2 form of 1,2,3-triazole were kept in an aluminum DSC pan. This pan was placed in the cell of DSC 2910 and heated to 265° C. at 10° C./min and air-cooled to RT. DSC analysis of the resulting material showed a single melting endotherm at 275° C. indicative of the neat N-1 Form.

Example 16C

Preparation of N-1 Form or 1,2,3-Triazole Derivative II by Solvent Mediated Transformation from the Corresponding P-2 Form 60 mg of P-2 form of 1,2,3-triazole derivative II were stirred in 3 mL of IPA for 1-2 days. The suspension was filtered and the solid residue was air dried. A white powder was obtained, the DSC analysis for which showed a single melting endotherm at 278.8° C. matching a neat N-1 form. Its PXRD was also different than original form.

The P-2 form was prepared by crystallization of crude 1,2,3-triazole derivative II with MeOH or by crystallization of the crude 1,2,3-triazole derivative II with MeOH followed by chomatography on silica gel using hexane/AcOEt/$CHCl_3$/MeOH.

Example 17

Preparation of Oral Solution Formulation of 1,2,3-Triazole Derivative II 1,2,3-Triazole derivative II oral solution formulations were prepared using N-1 crystalline 1,2,3-triazole derivative II material. The solutions were prepared in pharmaceutically acceptable solvent systems/vehicles in the concentration range of 0.5 mg/mL to 2.0 mg/mL as described below:

A vehicle for oral solution was initially prepared containing Polyethylene Glycol 400 (PEG 400), NF, d-Alpha Tocopheryl Polyethylene Glycol 1000-Succinate, NF (TPGS) and Ethyl Alcohol, USP. The vehicle was prepared by mixing the components at Polyethylene Glycol 400 (PEG 400), NF, ratio in the range of 40-100% (w/w), d-Alpha Tocopheryl Polyethylene Glycol 1000-Succinate, NF (TPGS) in the range of 0 to 25% (w/w), and Ethyl Alcohol, USP in the range of 0 to 25% (w/w). Other solvent systems were evaluated, and included mixtures of some or all of the above components and other pharmaceutically acceptable excipients such as Polyvinyl Pyrrolidone (PVP), HPMC, propylene glycol (PG) and others. Appropriate amounts of 1,2,3-triazole derivative II crystalline N-1 material were added to the above vehicles to provide the required concentrations in the 0.5 mg/mL to 2.0 mg/mL range.

Preparation of Vehicle for 1,2,3-Triazole Derivative II Oral Solution

Specifically a vehicle for 1,2,3-triazole derivative II oral solution at a composition of 75% (w/w) Polyethylene Glycol 400 (PEG 400), NF, 10% (w/w) d-Alpha Tocopheryl Polyethylene Glycol 1000-Succinate, NF (TPGS) and 15% (w/w) Ethyl Alcohol, USP was prepared by initially heating d-Alpha Tocopheryl Polyethylene Glycol 1000-Succinate, NF, in a 60° C. oven for 30-60 minutes until contents were completely melted. The required weight of d-Alpha Tocopheryl Polyethylene Glycol 1000-Succinate, NF, was transferred into an appropriate glass container/beaker/bottle. Polyethylene Glycol 400, NF, was then added into the container/beaker/bottle, followed by the addition of the required amount of Ethyl Alcohol, USP. The mixture was vortexed for 1 minute to mix the contents and placed in a 60° C. oven for 10-15 minutes until contents were completely melted.

Preparation of 1,2,3-Triazole Derivative II Oral Solution, 0.75 mg/mL

The vehicle for 1,2,3-triazole derivative II oral solution as prepared above was initially shaken/vortexed for 1-2 minutes and ~26.7 mL were drawn out using a 30 mL syringe and charged into a vial/glass container containing 20 mg of 1,2,3-triazole derivative II. The capped vial/glass container was vortexed for 2 minutes, placed into an ultrasonic water bath and sonicated at 50° C. (±5° C.) for no less than one (1) hour, or until all of the drug dissolved. The clear solution represented 1,2,3-triazole derivative II oral solution at 0.75 mg/mL. Other 1,2,3-triazole derivative II concentrations were prepared in a similar manner.

Example 17A

Preparation of Oral Suspension Formulation of 1,2,3-Triazole Derivative II Crystalline N-1 Form 1,2,3-Triazole Derivative II oral suspension formulations were prepared using N-1 crystalline 1,2,3-triazole derivative II material. The suspension was prepared in pharmaceutically acceptable solvent systems/vehicles in the concentration range of 0.5 mg/mL to 10.0 mg/mL as described below:

An aqueous suspending vehicle for oral suspension was prepared of Microcrystalline Cellulose (Avicel® RC 591), NF, Microcrystalline Cellulose (PH101), NF, and Denatonium Benzoate, NF (masking agent), in Purified Water, USP, or Water for Injection, USP. The vehicle was prepared by mixing the components at Microcrystalline Cellulose (Avicel® RC 591), NF, in the range of 0.25-2.0% w/v, Microcrystalline Cellulose (PH101), NF, in the range of 0-5% w/v, and Denatonium Benzoate, NF, at 0-0.0001% w/v, in Purified Water, USP, or Water for Injection, USP. Other suspending vehicles were evaluated, and included mixtures of some or all of the above components and other pharmaceutically acceptable excipients such as Pregelatinized Starch, calcium carbonate and others. Appropriate amounts of 1,2,3-triazole derivative II crystalline N-1 material were added to the above vehicles and mixed/sonicated to provide the required concentrations in the 0.5 mg/mL to 10.0 mg/mL range.

Preparation of Vehicle for 1,2,3-Triazole Derivative II Oral Suspension

Specifically, a vehicle for 1,2,3-triazole derivative II oral suspension at a composition of 1.25% w/v Microcrystalline Cellulose (Avicele RC 591), NF, 5% w/v Microcrystalline Cellulose (PH101), NF, and 0.0001% w/v Denatonium Benzoate, NF (masking agent), in Purified Water, USP, or Water for Injection, USP, was prepared. The required weight of Microcrystalline Cellulose (Avicel® RC 591), NF, was transferred into an appropriate glass container/beaker/bottle. Microcrystalline Cellulose (PH101), NF, was then added into the container/beaker/bottle, followed by the addition of the required volume of a stock solution of Denatonium Benzoate, NF. The required volume was then adjusted using Purified Water, USP, or Water for Injection, USP. The suspending vehicle was vortexed for 1 minute to mix the contents and placed in a sonicator for 10-15 minutes until contents were homogeneous.

Preparation of 1,2,3-Triazole Derivative II Oral Suspension, 8 mg/mL

The vehicle for 1,2,3-triazole derivative II oral suspension as prepared above was initially shaken/vortexed for 1-2 minutes and 25 mL were drawn out using a 30 mL syringe and charged into a vial/glass container containing 200 mg of 1,2,3-triazole derivative II. The capped vial/glass container was vortexed for 2 minutes, placed into an ultrasonic water bath and sonicated for 10-15 minutes, or until all of the contents were homogeneous. The suspension represented 1,2,3-triazole derivative II oral suspension at 8 mg/mL. Other 1,2,3-triazole derivative II concentrations were prepared in a similar manner.

Example 18

Preparation of Stabilized Amorphous 1,2,3-Triazole Derivative II/PVP (40/60 w/w) Using Flash Evaporation A mixture of 50 mL acetonitrile and 50 mL of ethanol was added to a mixture of crystalline Form N-1 of the 1,2,3-triazole derivative II (0.12 g) and polyvinylpyrrolidone (PVP K-30) (0.18 g). The resulting mixture was heated to about 70° C. to effect solubilization. The resulting solution was filtered though a 0.45 or 0.20 μm filter and the solvent was stripped using flash evaporation.

Figure 2:
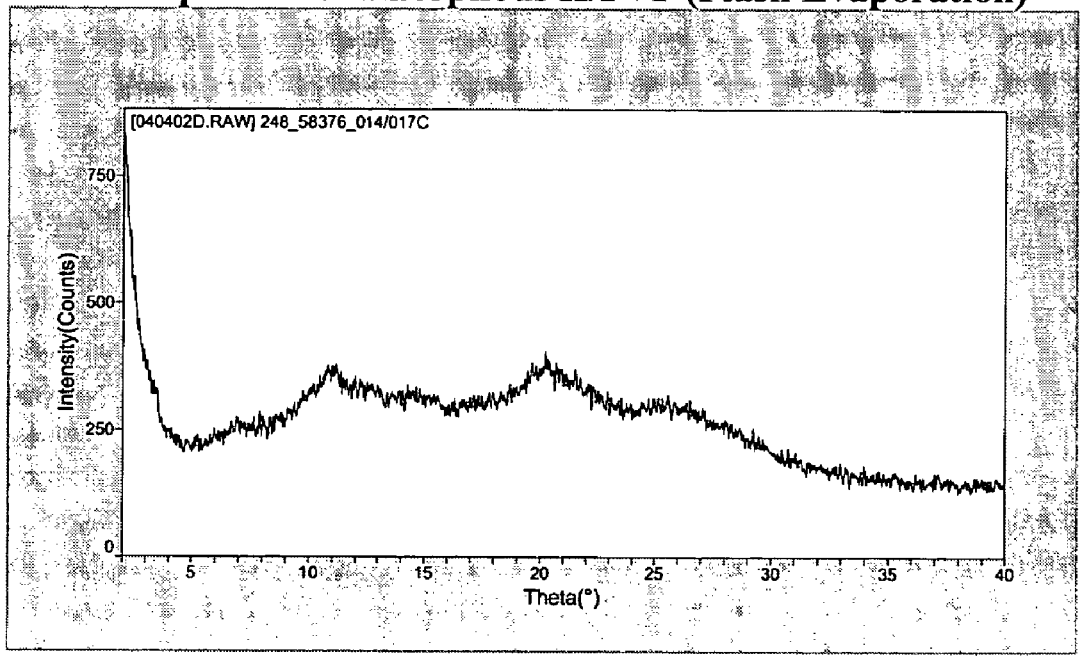
FIG. 2 shows an observed powder X-ray diffraction pattern (PXRD) of the stabilized amorphous form of the 1,2,3-triazole derivative II prepared by flash evaporation.

Complete amorphization was confirmed by DSC (FIG. 1) and PXRD (FIG. 2).

Example 19

Preparation of Stabilized Amorphous 1,2,3-Triazole Derivative II by Spray Drying (Spray Dried Intermediate, SDI)

Spray-drying of crystalline Form N-1 of the 1,2,3-triazole derivative II with various excipients at different compositions resulted in amorphous 1,2,3-triazole derivative II. The following compositions were used to prepare amorphous 1,2,3-triazole derivative II: 20% 1,2,3-triazole derivative 11/80% polyvinylpyrrolidone K30 (PVP, w/w), 20% 1,2,3-triazole derivative II/80% PVP-VA (polyvinylpyrrolidone-vinyl acetate copolymer, w/w), 40% 1,2,3-triazole derivative II/60% polyvinylpyrrolidone K30 (PVP, w/w), 40% 1,2,3-triazole derivative II/60% PVP-VA (polyvinylpyrrolidone-vinyl acetate copolymer, w/w), 20% 1,2,3-triazole derivative II/75% PVP-VA/5% d-alpha tocopheryl polyethylene glycol 1000 succinate (TPGS). The solvents used to dissolve the mixture for spray-drying included dichloromethane, dichloromethane/ethanol (80/20, v/v) and dichloromethane/ethanol/water (80/19/1, v/v/v).

The preferred method of preparing amorphous 1,2,3-triazole derivative II is to dissolve 40% 1,2,3-triazole derivative II/60% PVP K30 at 5 mg/mL in dichloromethane/ethanol/water (80/19/1, v/v/v). The solution is then spray-dried to give amorphous 40% 1,2,3-triazole derivative II/60% PVP-K30. Details of this process are provided in Example 19.

Example 20

Preparation of Amorphous 1,2,3-Triazole by Spray Drying

Form N-1 of the 1,2,3-triazole derivative II (4.0 g) and PVP-K30 (6.0 g) were dissolved in 800 mL of Jan. 19, 1980 (v/v) water/ethanol/dichloromethane, total solid concentration: 1.25% w/v. The solution was filtered to remove extraneous matter. The filtered solution was sprayed at the rate of 15% (~8 mL/min) with atomizing nitrogen of 400 Nl/hour. The inlet temperature of the spray dryer was maintained at 100±5° C. The outlet temperature was maintained at 65±5° C. The resulting particles were separated in a cyclone and collected in a receiving vessel.

Range of Processing Conditions Used in Buchi B-191 Spray Dryer:

Inlet temperature: 45-110° C.

Outlet temperature: 35-70° C.

Flow rate: ~8-15 mL/min

Solution concentration: 0.65-1.25% w/v

Figure 3:
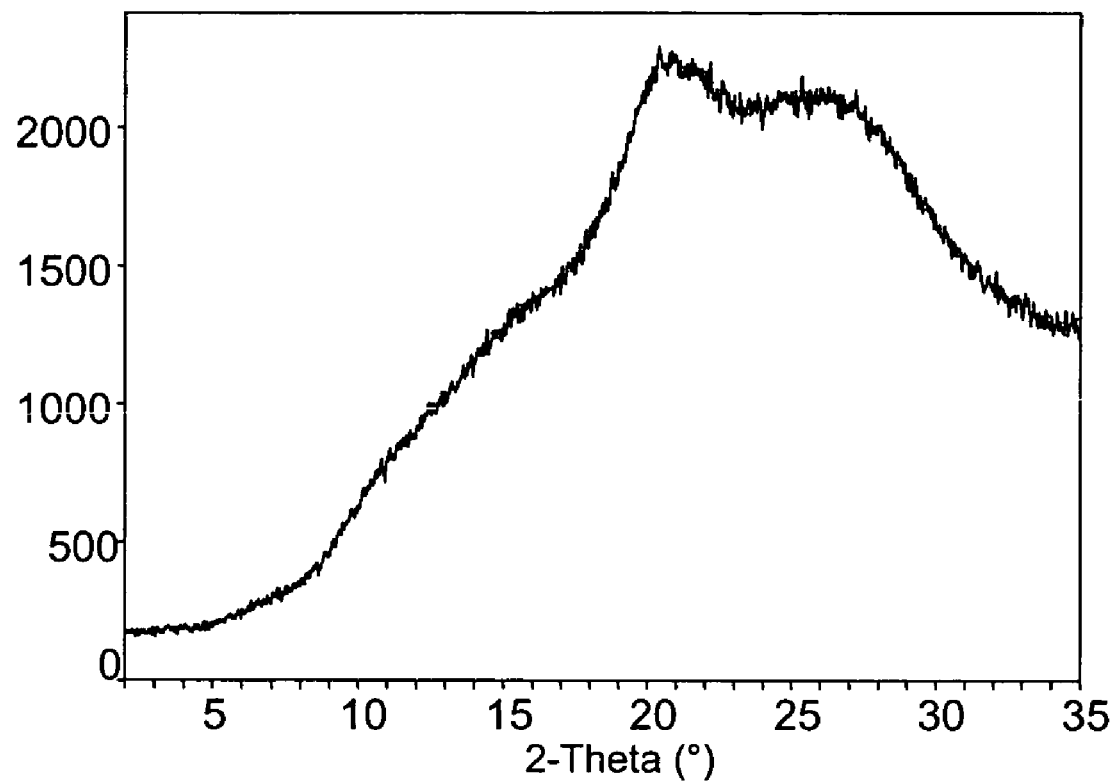
FIG. 3 shows an observed (experimental at 24±3° C.) powder X-ray diffraction pattern of the stabilized amorphous form of the 1,2,3-triazole derivative II prepared by spray drying.
Figure 4A:
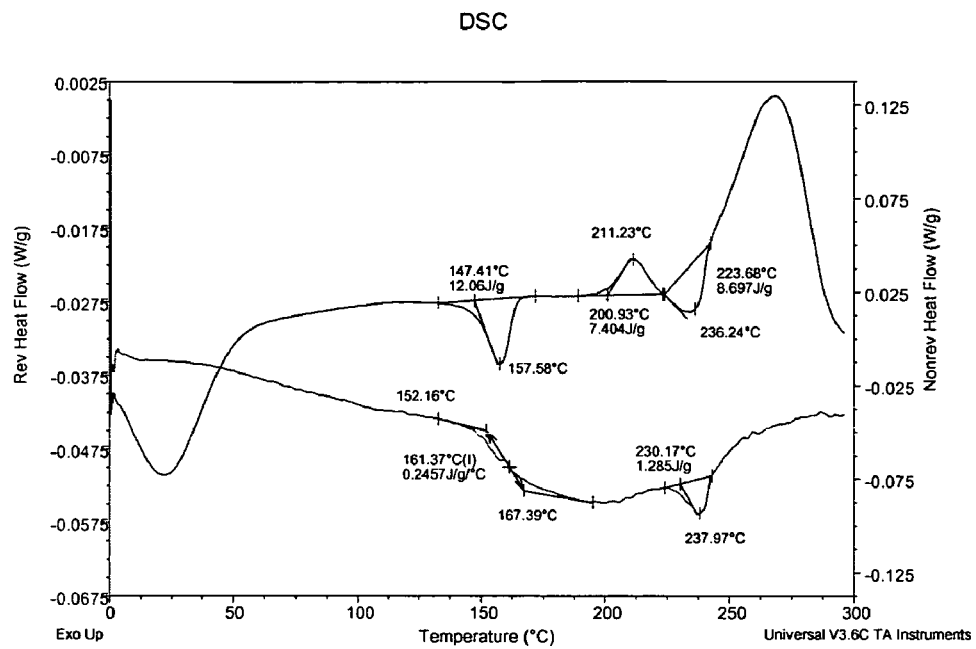
FIG. 4a shows a differential scanning calorimetry (DSC) thermogram of stabilized amorphous 1,2,3-triazole derivative II (open pan) prepared by spray drying.
Figure 4B:
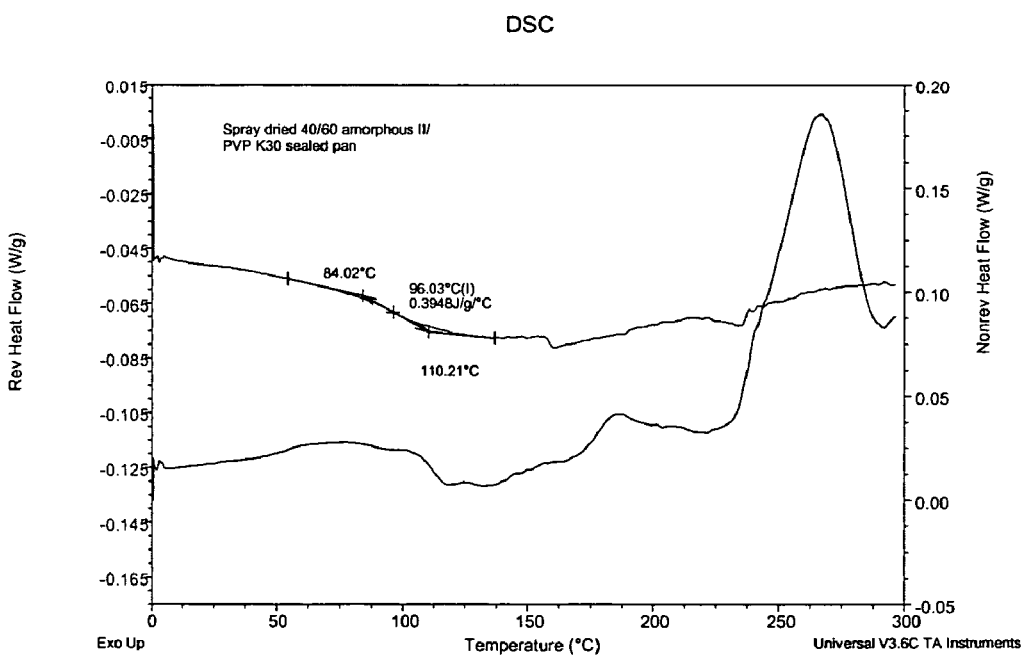
FIG. 4b shows a differential calorimetry (DSC) thermogram of the stabilized amorphous 1,2,3-triazole derivative II (sealed pan) prepared by spray drying.

A typical PXRD pattern of amorphous 1,2,3-triazole derivative II prepared by spray drying in the presence of excipients is given in FIG. 3. A typical modulated DSC (MDSC) curve of amorphous 1,2,3-triazole derivative II in the presence of excipients is given in FIG. 4a (open pan) and FIG. 4b (sealed pan).

Example 21

Preparation of Amorphous 1,2,3-Triazole Derviative II Employing an SD-Micro Spray Dryer Form N-1 of the 1,2,3-triazole derivative II (16 g) and PVP Plasdone-29/32 (equivelant to K30) (24 g) were dissolved in a mixed solvent of 3395.7 g DCM (dichloromethane) and 505.2 g absolute ethanol (200 proof). Total solid concentration was ~1.02% (w/w). The solution was sprayed though a two-fluid nozzle (0.5 mm diameter) with atomizing nitrogen pressure at 0.5 bar and a liquid flow rate of ~30 g/min. The processing gas flow rate (hot nitrogen) was set at ~25 kg/h. The inlet temperature of the spray dryer is maintained at 70±5° C. The outlet temperature was maintained at 45±5° C. The resulting particles were separated in a cyclone and collected in a receiving vessel.

Additional Conditions were Tested Using Niro's SDMicro Spray Dryer:
Range of Processing Conditions:
Inlet temperature: 60-100° C.
Outlet temperature: 40-80° C.
Flow rate: 20-30 g/min
Solution concentration is maintained around 1% w/w Example 22

Amorphous 1,2,3-Triazole Derivative II Prepared on a PSD-1 Spray Dryer

Form N-1 of the 1,2,3-triazole derivative II (134 g) and PVP (Plasdone-29/32, 201 g) were dissolved in a pre-mixed solvent containing absolute ethanol (200 proof) and DCM (4.2 kg/28.4 kg). Total solid concentration was ~1.03% (w/w). The solution was sprayed in a Niro PSD-1 spray dryer equipped with a two-fluid nozzle (1.0 mm diameter). An in-line filter (Demicap Peplyn Plus, 0.2-10 microns opening) was used (before the solution was pumped to the spraying nozzle) to remove any particulates in the solution. The filtered solution was then sprayed though the two-fluid nozzle with atomizing nitrogen pressure at 0.4 bar. The processing gas flow rate (hot nitrogen) was set at ~80 kg/h. The inlet temperature of the spray dryer was maintained at 110±2° C. and outlet temperature was maintained at 65±2° C. Feed solution flow rate was adjusted accordingly (to maintain the processing temperatures) but was measured to be ca. 80 g/min.

The resulting particles were separated in a cyclone and collected in a receiving vessel. Additional material was collected from the bag filter which was located after the cyclone. Material was further oven-dried to remove residual solvent DCM.

The same size batch was repeated in 3 sublets and a total of 631 g spray dried intermediate was collected. Total usable yield was 62.8%. Additional material was collected from the filter bag, from the brush-down of the drying chamber, and from vessels collecting the startup/shutdown and process tailings. Total accountability of material was added at 90%.

Example 23

Amorphous 1,2,3-Triazole Derivative II Prepared on a PSD-1 Spray Dryer

Form N-1 of the 1,2,3-triazole derivative II (138 g) and PVP (Plasdone-29/32, 207 g) were dissolved in a pre-mixed solvent containing absolute ethanol (200 proof) and DCM (4.4 kg/29.3 kg). Total solid concentration was ~1.03%. The solution was sprayed using a Niro PSD-1 spray dryer equipped with a two-fluid nozzle (1.0 mm diameter). An in-line filter (Demicap Peplyn Plus, 0.2-10 microns opening) was used (before the solution was pumped to the spraying nozzle) to remove any particulates in the solution. The filtered solution was then sprayed though the two-fluid nozzle with atomizing nitrogen pressure at 0.4 bar. The processing gas flow rate (hot nitrogen) was set at ~80 kg/h. The inlet temperature of the spray dryer was maintained at 110±2° C. and outlet temperature was maintained at 65±2° C. Feed solution flow rate was adjusted accordingly (to maintain the processing temperatures) but was measured to be ca. 80 g/min. The resulting particles were separated in a cyclone and collected in a receiving vessel. Material was further dried in a Niro-Aeromatic MP-1 Fluid Bed Processor to remove residual solvent. The same size batch was repeated in 6 sublets and a total of 1130 g spray dried intermediate was collected. Total useable yield was 54.6%. Additional material was collected from the filter bag, from the brush-down of the drying chamber, and from vessels collecting the startup/shutdown and process tailings. Total accountability of material was 89%.

Example 24

Preparation of Capsules Containing Stabilized Amorphous 1,2,3-Triazole Derivative II Amorphous 1,2,3-triazole derivative II capsules, 10 mg, 25 mg, 50 mg and 75 mg were prepared using 1,2,3-triazole derivative II/polyvinylpyrrolidone spray dried intermediate (SDI), prepared as described below, dry granulated with excipients to provide a 1,2,3-triazole derivative II stock granulation (25% w/w 1,2,3-triazole derivative II).

Amorphous 1,2,3-triazole derivative II/polyvinylpyrrolidone Spray Dried Intermediate was prepared as follows:

Polyvinylpyrrolidone (Plasdone® K-29/32, PVP) was added to a pre-mixed methylene chloride, ethanol, and water solvent mixture and stirred until a solution was obtained. 1,2,3-Triazole derivative II was then added to the above solution and the mixture was continuously stirred until 1,2,3-triazole derivative II was fully dissolved. The solution was then passed though the pre-heated spray dryer nozzle to prepare 1,2,3-triazole derivative II/polyvinylpyrrolidone spray dried powder. The powder was then subjected to additional drying in a fluid-bed dryer to remove residual solvents to generate the 1,2,3-triazole derivative II/polyvinylpyrrolidone spray dried intermediate (SDI) that was used in the manufacture of the capsules. 1,2,3-triazole derivative II/polyvinylpyrrolidone spray dried intermediate was dry granulated with other excipients (namely silicon dioxide, sodium lauryl sulfate, sodium starch glycolate, calcium carbonate and magnesium stearate) to prepare a common stock granulation (25% w/w 1,2,3-triazole derivative II). All capsule strengths were manufactured using the common stock granulation. The stock granulation was then filled into appropriate sized capsules.

Table A sets out the composition of stabilized amorphous 1,2,3-triazole derivative II containing capsules (10 mg, 25 mg, 50 mg and 75 mg).

TABLE A

Composition of 1,2,3-Triazole Derivative Capsules

| Component | Reference Standard | Function | 10 mg[b] | 25 mg[b] | 50 mg[b] | 75 mg[c] |
|---|---|---|---|---|---|---|
| | | | \multicolumn{4}{c}{Quantity per unit dose} | | | |
| 1,2,3-Triazole derivative/ Polyvinylpyrrolidone Spray Dried Intermediate[a] | | Active ingredient | 25.0 mg | 62.50 mg | 125.00 mg | 187.50 mg |
| Silicon Dioxide | NF | Filler/Flow aid | 7.6 mg | 19.00 mg | 38.00 mg | 57.00 mg |
| Calcium Carbonate | USP | Filler/Flow aid | 4.9 mg | 12.25 mg | 24.50 mg | 36.75 mg |
| Sodium Starch Glycolate | NF | Disintegrant | 2.0 mg | 5.00 mg | 10.00 mg | 15.00 mg |
| Sodium Lauryl Sulfate | NF | Dissolution Enhancer | 0.3 mg | 0.75 mg | 1.50 mg | 2.25 mg |
| Magnesium Stearate | NF | Lubricant | 0.2 mg | 0.50 mg | 1.00 mg | 1.50 mg |
| Total weight | — | — | 40.0 mg | 100.00 mg | 200.00 mg | 300.0 mg |
| Capsules | — | — | One capsule | One capsule | One capsule | One capsule |

[a]The composition of 1,2,3-triazole derivative II/polyvinylpyrrolidone spray dried intermediate (SDI) is 40% 1,2,3-triazole derivative II/60% polyvinylpyrrolidone (w/w). A commonstock granulation (25% w/w as 1,2,3-triazole derivative II) was prepared by mixing the SDI with excipients as a dry granulation. Different doses/potencies were derived by encapsulating the desired fill weight in size #0 or 00 capsules.
[b]Gray opaque #0 capsule
[c]Gray opaque #00 capsule

Example 25

Studies of Crystal Forms Prepared in Previous Examples

1. The X-ray powder diffraction (PXRD) data were obtained with a Bruker D8 Advance diffractometer (Karlsruhe, Germany) which was equipped with a monochomated CuKα source operating at a tube load of 40 KV and 40 mA. A system of divergence, anti-scatter and receiving slits of 1.0, 1.0 and 0.1 mm, respectively, was employed. The sample was scanned in a locked coupled scan mode (step size 0.05°; scan speed 0.4 s per step) from 5 to 40° 2θ.

2. X-ray powder diffraction (PXRD) data were also obtained using a Bruker GADDS (General Area Detector Diffraction System) manual. Powder samples were placed in thin walled glass capillaries of 1 mm or less in diameter; the capillary was rotated during data collection. The sample-detector distance was 15 cm. The radiation was Cu Kα (λ=1.5418 Ang). Data were collected for $3 \leq 2\theta \leq 35°$ with a sample exposure time of at least 1800 seconds.

3. All the simulated PXRD patterns were calculated from refined atomic coordinates of crystal structures at the room temperature, by using JPOWD software (JPOWD. Powder Diffraction Simulation and Structure Display. Materials Data Inc., Livermore, Calif., USA, 2000).

4. Single crystal X-ray data were collected on a Bruker SMART 2K CCD diffractometer equipped with graphite-monochomated Cu Kα radiation, (λ=1.54056 Å). A full data set was collected using the ω scan mode over the 2θ range with a crystal-to-detector distance of 4.98 cm. An empirical absorption correction utilized the SADABS routine associated with the diffractometer (Bruker AXS. 1998, SMART and SAINTPLUS. Area Detector Control and Integration Software, Bruker AXS, Madison, Wis., USA, 1998). The final unit cell parameters were determined using the entire data set.

5. All structures were solved by direct methods and refined by the full-matrix least-squares techniques, using SHELXTL (Sheldrick, G M. 1997, SHELXTL. Structure Determination Programs. Version 5.10, Bruker AXS, Madison, Wis., USA.).

6. The derived atomic parameters (coordinates and temperature factors) were refined though full matrix least-squares. The function minimized in the refinements was $\Sigma_w(|F_O|-|F_C|)^2$. R is defined as $\Sigma||F|-|F||/\Sigma|F_O|$ while $R_W = [\Sigma_w(|F_O|-|F_C|)^2/\Sigma_w|F_O|^2]^{1/2}$ where w is an appropriate weighting function based on errors in the observed intensities. Difference maps were examined at all stages of refinement. Hydrogen atoms were introduced in idealized positions with isotropic temperature factors.

7. The crystal data for N-1 form of the invention including unit cell constants, space group and atomic coordinates in the asymmetric unit are tabulated in Tables 1 and 2. A detailed account of the technique used for the sngle crystal analysis can be found in Stout & Jensen, "*X-Ray Structure Determination: A Practical Guide*", (MacMillian, 1968).

8. Differential scanning calorimetry (DSC) experiments were performed on a TA Instruments™ model Q1000. The sample (about 2-6 mg) was weighed in an open aluminum pan or sealed pan with pin hole and recorded accurately recorded to a hundredth of a milligram, and transferred to the DSC. The instrument was purged with nitrogen gas at 50 mL/min. Data were collected between room temperature and 300° C. at 10° C./min heating rate. The plot was made with the endothermic peaks pointing down.

9. Thermal gravimetric analysis (TGA) experiments were performed in a TA Instruments™ model Q500. The sample (about 10-30 mg) was placed in a platinum pan previously tared. The weight of the sample was measured accurately and recorded to a thousand of a milligram by the instrument. The furnace was purged with nitrogen gas at 100 mL/min. Data were collected between room temperature and 300° C. at 10° C./min heating rate.

10. Moisture-sorption isotherms were collected in a VTI SGA-100 Symmetric Vapor Analyzer using approximately 10 mg of sample. The sample was dried at 60° C. until the loss rate of 0.0005 wt %/min was obtained for 10 minutes. The sample was tested at 25° C. and 3 or 4, 5, 15, 25, 35, 45, 50, 65, 75, 85, and 95% RH. Equilibration at each RH was reached when the rate of 0.0003 wt %/min for 35 minutes was achieved or a maximum of 600 minutes.

TABLE 1

Single Crystal data and structure refinement for Form N-1 of the 1,2,3-Triazole Derivative II

| | |
|---|---|
| Empirical formula | $C_{22} H_{18} F_1 N_7 O_3$ |
| Formula weight | 447.43 |
| Temperature | 293(2) K |
| Wavelength | 1.54178 A |
| Crystal system, space group | Monoclinic, C2/c |
| Unit cell dimensions | a = 39.2481(14) Å   α = 90° |
| | b = 5.5577(2) Å    β = 122.399(4)° |
| | c = 21.8072(10) Å  γ = 90° |
| Volume | 4016.3(3) Å$^3$ |
| Z, Calculated density | 8, 1.480 Kg/m$^3$ |
| Absorption coefficient | 0.918 mm$^{-1}$ |
| Crystal size | 0.25 × 0.05 × 0.02 mm |
| θ range for data collection | 2.67 to 60.40° |

Fractional atomic coordinates for the Form N-1 of the 1,2,3-triazole derivative II are tabulated in Table 2.

TABLE 2

Atomic coordinates (×10$^4$) and equivalent isotropic displacement parameters (Å$^2$ × 10$^3$). U(eq) is defined as one third of the trace of the orthogonalized Uij tensor

| | x | y | z | U(eq) |
|---|---|---|---|---|
| O(1) | 5444(1) | −432(9) | 3445(2) | 67(1) |
| O(2) | 5456(1) | 993(7) | 4862(2) | 56(1) |
| O(3) | 3827(1) | 6741(12) | 1978(3) | 114(2) |
| N(1) | 6607(1) | 2448(8) | 4493(2) | 45(1) |
| N(2) | 6700(1) | 7748(8) | 5605(3) | 50(1) |
| N(3) | 7232(1) | 6128(8) | 5563(2) | 42(1) |
| N(4) | 7408(1) | 4199(8) | 5474(3) | 56(1) |
| N(5) | 7788(1) | 4753(9) | 5745(3) | 55(1) |
| N(6) | 4959(2) | 2636(10) | 3810(3) | 64(2) |
| N(7) | 4293(2) | 5667(13) | 3089(3) | 96(2) |
| F(1) | 5666(1) | 6028(6) | 4842(2) | 65(1) |
| C(1) | 6257(2) | 1249(10) | 4093(3) | 42(1) |
| C(2) | 6558(2) | 4283(9) | 4866(3) | 39(1) |
| C(3) | 6817(2) | 6046(10) | 5328(3) | 44(1) |
| C(4) | 6311(2) | 7685(11) | 5420(3) | 54(2) |
| C(5) | 6048(2) | 5980(10) | 4996(3) | 46(2) |
| C(6) | 6159(2) | 4181(9) | 4692(3) | 41(1) |
| C(7) | 5973(2) | 2191(10) | 4214(3) | 41(1) |
| C(8) | 7846(2) | 7025(12) | 5999(3) | 58(2) |
| C(9) | 7499(2) | 7938(11) | 5889(3) | 56(2) |
| C(10) | 5578(2) | 1128(11) | 3916(3) | 47(2) |
| C(11) | 5323(2) | 1688(10) | 4246(3) | 47(2) |
| C(12) | 4820(3) | 3682(18) | 3094(5) | 117(4) |
| C(13) | 4618(2) | 5763(19) | 2945(5) | 123(4) |
| C(14) | 4444(3) | 4810(20) | 3842(5) | 122(4) |
| C(15) | 4649(2) | 2648(14) | 3988(4) | 80(2) |
| C(16) | 3917(2) | 6071(12) | 2578(4) | 61(2) |
| C(17) | 3590(2) | 5667(11) | 2728(3) | 49(2) |
| C(18) | 3509(2) | 7309(12) | 3101(4) | 70(2) |
| C(19) | 3179(2) | 6970(15) | 3168(4) | 77(2) |
| C(20) | 2942(2) | 5019(18) | 2868(4) | 81(2) |
| C(21) | 3022(2) | 3372(14) | 2494(4) | 76(2) |
| C(22) | 3349(2) | 3710(12) | 2431(4) | 68(2) |
| H(1N) | 6827 | 2124 | 4513 | 70(20) |
| H(1A) | 6213 | −24 | 3782 | 50 |
| H(4A) | 6221 | 8889 | 5597 | 65 |
| H(8A) | 8091 | 7845 | 6218 | 70 |
| H(9A) | 7455 | 9460 | 6010 | 67 |
| H(12A) | 5053 | 3938 | 3058 | 140 |
| H(12B) | 4647 | 2519 | 2725 | 140 |
| H(13A) | 4503 | 6161 | 2438 | 148 |
| H(13B) | 4805 | 7033 | 3236 | 148 |
| H(14A) | 4622 | 6017 | 4187 | 147 |
| H(14B) | 4217 | 4613 | 3901 | 147 |
| H(15A) | 4456 | 1382 | 3715 | 96 |
| H(15B) | 4775 | 2283 | 4500 | 96 |

TABLE 2-continued

Atomic coordinates (×10$^4$) and equivalent isotropic displacement parameters (Å$^2$ × 10$^3$). U(eq) is defined as one third of the trace of the orthogonalized Uij tensor

| | x | y | z | U(eq) |
|---|---|---|---|---|
| H(18A) | 3674 | 8648 | 3309 | 84 |
| H(19A) | 3122 | 8087 | 3419 | 93 |
| H(20A) | 2722 | 4787 | 2915 | 97 |
| H(21A) | 2857 | 2035 | 2284 | 91 |
| H(22A) | 3405 | 2585 | 2182 | 82 |

What is claimed is:

1. A process for preparing compound IA having the structure

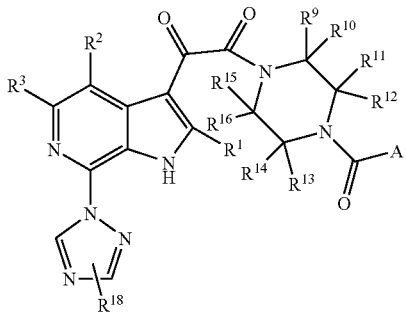

IA where A is selected from the group consisting of $C_{1-6}$alkoxy, aryl and heteroaryl; in which said aryl is phenyl or naphthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, —C(O)NH$_2$, $C_{1-6}$alkyl, —NHC(O)CH$_3$, halogen and trifluoromethyl; and R$^{18}$ is H or alkyl;

R$^9$, R$^{10}$, R$^{11}$, R$^{12}$, R$^{13}$, R$^{14}$, R$^{15}$ and R$^{16}$ are each independently H or (C$_{1-6}$)alkyl which may be optionally substituted with 1 to 3 same or different halogens;

which comprises reacting compound D having the structure

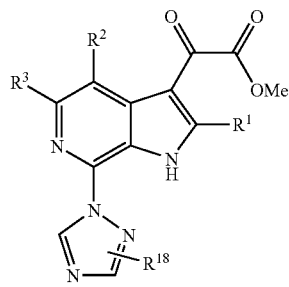

D with a compound of the structure

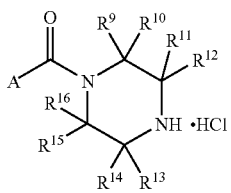

in the presence of an organometallic base to form compound IA,
  wherein the reaction is carried out at a temperature within the range from about −10 to about 30° C. and
  where in compounds D and IA, $R^2$ is $CH_3O$, $R^1$ is H and $R^3$ is H.

2. A process for preparing compound IIA as defined in claim 1 having the structure

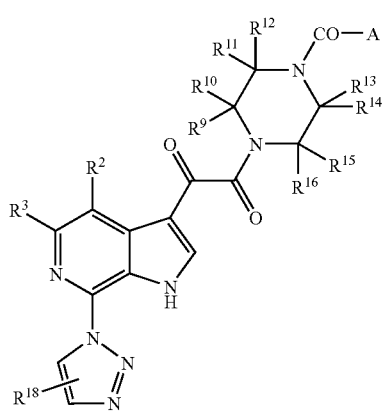

which comprises reacting compound L as defined in claim 1 of the structure

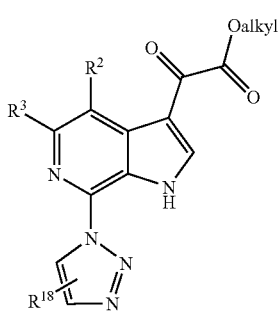

with a compound of the structure

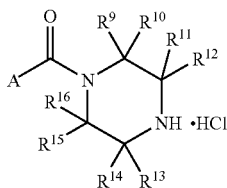

where $R^{18}$ is H or alkyl,
where A is selected from the group consisting of $C_{1-6}$alkoxy, aryl and heteroaryl; in which said aryl is phenyl or naphthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, —C(O)NH$_2$, $C_{1-6}$alkyl, —NHC(O)CH$_3$, halogen and trifluoromethyl; and
  $R^9$, $R^{10}$, $R^{11}$, $R^{12}$, $R^{13}$, $R^{14}$, $R^{15}$ and $R^{16}$ are each independently H or ($C_{1-6}$)alkyl which may be optionally substituted with 1 to 3 same or different halogens;
in the presence of an organometallic base to form compound IIA,
  wherein the reaction is carried out at a temperature within the range from about −20 to about 50° C. and
  where in the compounds IIA and L, $R^2$ is F, $R^3$ is H and $R^1$ is H.

3. A process for preparing compound IA having the structure

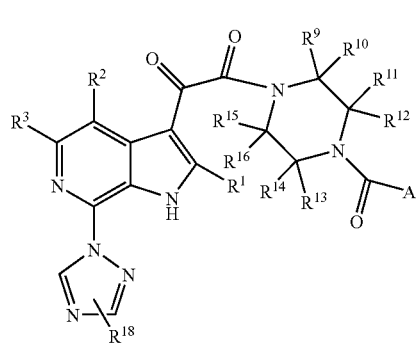

wherein $R^{18}$ is H or alkyl, $R^1$, $R^2$ and $R^3$ are independently selected from the group consisting of hydrogen, halogen, cyano, nitro, COOR$^{56}$, XR$^{57}$, C(O)R$^7$, C(O)NR$^{55}$R$^{56}$, B, D, and E;
  B is selected from the group consisting of —C(=NR$^{46}$)(R$^{47}$), C(O)NR$^{40}$R$^{41}$, aryl, heteroaryl, heteroalicyclic, S(O)$_2$R$^8$, C(O)R$^7$, XR$^{8a}$, (C$_{1-6}$)alkylNR$^{40}$R$^{41}$, (C$_{1-6}$)alkylCOOR$^{8b}$; wherein said aryl, heteroaryl, and heteroalicyclic are optionally substituted with one to three same or different halogens or from one to three same or different substituents selected from the group F; wherein aryl is naphthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;
  D is selected from the group consisting of (C$_{1-6}$)alkyl and (C$_{2-6}$)alkenyl; wherein said (C$_{1-6}$)alkyl and (C$_{2-6}$)alkenyl are optionally substituted with one to three same or different halogens or from one to three same or different substituents selected from the group consisting of C(O)NR$^{55}$R$^{56}$, hydroxy, cyano and XR$^{57}$;
  X is NH, NCH$_3$ O or S;
  E is selected from the group consisting of (C$_{1-6}$)alkyl and (C$_{2-6}$)alkenyl; wherein said (C$_{1-6}$)alkyl and (C$_{2-6}$)alkenyl are independently optionally substituted with a member selected from the group consisting of phenyl, heteroaryl, SMe, SPh, —C(O)NR$^{56}$R$^{57}$, C(O)R$^{57}$, SO$_2$ ($C_{1-6}$)alkyl and $SO_2Ph$; wherein heteroaryl is a monocyclic system which contains from 3 to 7 ring atoms, including from 1 to 4 heteroatoms;

F is selected from the group consisting of ($C_{1-6}$)alkyl, ($C_{3-7}$)cycloalkyl, aryl, heteroaryl, heteroalicyclic, hydroxy, ($C_{1-6}$)alkoxy, aryloxy, ($C_{1-6}$)thioalkoxy, cyano, halogen, nitro, —C(O)$R^{57}$, benzyl, —$NR^{42}$C(O)—($C_{1-6}$)alkyl, —$NR^{42}$C(O)—($C_{3-6}$)cycloalkyl, —$NR^{42}$C(O)-aryl, —$NR^{42}$C(O)-heteroaryl, —$NR^{42}$C(O)-heteroalicyclic, a 4, 5, or 6 membered ring cyclic N-lactam, —$NR^{42}S(O)_2$—($C_{1-6}$)alkyl, —$NR^{42}S(O)_2$—($C_{3-6}$)cycloalkyl, —$NR^{42}$S(O)2-aryl, —$NR^{42}S(O)_2$-heteroaryl, —$NR^{42}$S(O)2-heteroalicyclic, $S(O)_2(C_{1-6})$alkyl, $S(O)_2$aryl, —$S(O)2NR^{42}R^{43}$, $NR^{42}R^{43}$, ($C_{1-6}$)alkylC(O)$NR^{42}R^{43}$, C(O)$NR^{42}R^{43}$, NHC(O)$NR^{42}R^{43}$, OC(O)$NR^{42}R^{43}$, NHC(O)$OR^{54}$, ($C_{1-6}$)alkyl$NR^{42}R^{43}$, $COOR^{54}$, and ($C_{1-6}$)alkyl$COOR^{54}$; wherein said ($C_{1-6}$)alkyl, ($C_{3-7}$)cycloalkyl, aryl, heteroaryl, heteroalicyclic, ($C_{1-6}$)alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of ($C_{1-6}$)alkyl, ($C_{3-7}$)cycloalkyl, aryl, heteroaryl, heteroalicyclic, hydroxy, ($C_{1-6}$)alkoxy, aryloxy, cyano, halogen, nitro, —C(O)$R^{57}$, benzyl, —$NR^{48}$C(O)—($C_{1-6}$)alkyl, —$NR^{48}$C(O)—($C_{3-6}$)cycloalkyl, —$NR^{48}$C(O)-aryl, —$NR^{48}$C(O)-heteroaryl, —$NR^{48}$C(O)-heteroalicyclic, a 4, 5, or 6 membered ring cyclic N-lactam, —$NR^{48}S(O)_2$-($C_{1-6}$)alkyl, —$NR^{48}S(O)_2$—($C_{3-6}$)cycloalkyl, —$NR^{48}$S(O)2-aryl, —$NR^{48}S(O)_2$-heteroaryl, —$NR^{48}$S(O)2-heteroalicyclic, sulfinyl, sulfonyl, sulfonamide, $NR^{48}R^{49}$, ($C_{1-6}$)alkyl C(O)$NR^{48}R^{49}$, C(O)$NR^{48}R^{49}$, NHC(O)$NR^{48}R^{49}$, OC(O)$NR^{48}R^{49}$, NHC(O)$OR^{54}$, ($C_{1-6}$)alkyl$NR^{48}R^{49}$, $COOR^{54}$, and ($C_{1-6}$)alkyl$COOR^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

$R^7$ is selected from the group consisting of aryl, heteroaryl, and heteroalicyclic; wherein said aryl, heteroaryl, and heteroalicyclic are optionally substituted with one to three same or different halogens or with from one to three same or different substituents selected from the group F; wherein for $R^7$, $R^8$, $R^{8a}$, $R^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

$R^8$ is selected from the group consisting of hydrogen, ($C_{1-6}$)alkyl, ($C_{3-7}$)cycloalkyl, ($C_{2-6}$)alkenyl, ($C_{3-7}$)cycloalkenyl, ($C_{2-6}$)alkynyl, aryl, and heteroalicyclic; wherein said ($C_{1-6}$)alkyl, ($C_{3-7}$)cycloalkyl, ($C_{2-6}$)alkenyl, ($C_{3-7}$)cycloalkenyl, ($C_{2-6}$)alkynyl, aryl, heteroaryl, and heteroalicyclic are optionally substituted with one to six same or different halogens or from one to five same or different substituents selected from the group F;

$R^{8a}$ is a member selected from the group consisting of aryl, heteroaryl, and heteroalicyclic; wherein each member is independently optionally substituted with one to six same or different halogens or from one to five same or different substituents selected from the group F;

$R^{8b}$ is selected from the group consisting of hydrogen, ($C_{1-6}$)alkyl and phenyl;

$R^{40}$ and $R^{41}$ are independently selected from the group consisting of
(a) hydrogen;
(b) ($C_{1-6}$)alkyl or ($C_{3-7}$)cycloalkyl substituted with one to three same or different halogens or from one to two same or different substituents selected from the group F; and
(c) ($C_{1-6}$)alkoxy, aryl, heteroaryl or heteroalicyclic; or $R^{40}$ and $R^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for $R^{40}$ and $R^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is C(O)$NR^{40}R^{41}$, at least one of $R^{40}$ and $R^{41}$ is not selected from groups (a) or (b);

$R^{42}$ and $R^{43}$ are independently selected from the group consisting of hydrogen, ($C_{1-6}$)alkyl, allyl, ($C_{1-6}$)alkoxy, ($C_{3-7}$)cycloalkyl, aryl, heteroaryl and heteroalicyclic; or $R^{42}$ and $R^{43}$ taken together with the nitrogen to which they are attached form a member selected from the group consisting of aziridine, azetidine, pyrrolidine, piperazine, 4-NMe piperazine, piperidine, azepine, and morpholine; and wherein said ($C_{1-6}$)alkyl, ($C_{1-6}$)alkoxy, ($C_{3-7}$)cycloalkyl, heteroaryl, and heteroalicyclic are optionally substituted with one to three same or different halogens or from one to two same or different substituents selected from the group G; wherein for $R^{42}$ and $R^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

$R^{46}$ is selected from the group consisting of H, $OR^{57}$, and $NR^{55}R^{56}$;

$R^{47}$ is selected from the group consisting of H, amino, halogen, phenyl, and ($C_{1-6}$)alkyl;

$R^{48}$ and $R^{49}$ are independently selected from the group consisting of hydrogen, ($C_{1-6}$)alkyl and phenyl;

$R^{54}$ is selected from the group consisting of hydrogen and ($C_{1-6}$)alkyl;

$R^{56}$ is independently selected from the group consisting of hydrogen and ($C_{1-6}$)alkyl; and $R^{57}$ is selected from the group consisting of hydrogen, ($C_{1-6}$)alkyl and phenyl, where A is selected from the group consisting of $C_{1-6}$alkoxy, aryl and heteroaryl; in which said aryl is phenyl or naphthyl; said heteroaryl is selected from the group consisting of pyridinyl, pyrimidinyl, pyrazinyl, triazinyl, furanyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, —C(O)NH$_2$, $C_{1-6}$alkyl, —NHC(O)CH$_3$, halogen and trifluoromethyl; and $R^9$, $R^{10}$, $R^{11}$, $R^{12}$, $R^{13}$, $R^{14}$, $R^{15}$ and $R^{16}$ are each independently H or ($C_{1-6}$)alkyl which may be optionally substituted with 1 to 3 same or different halogens;

which comprises subjecting compound C as defined in claim 1 of the structure

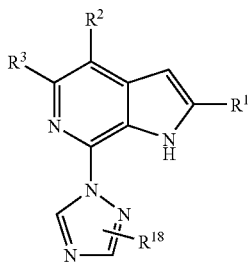

C to a Grignard acylation reaction wherein acid chloride 1

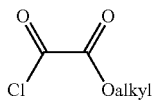

1 is reacted with compound C to form compound D

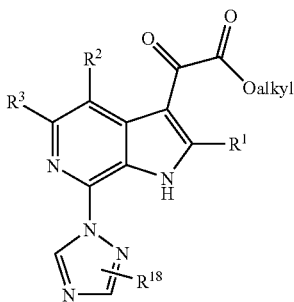

D and reacting compound D with a compound of the structure $D^a$

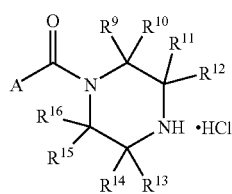

$D^a$ in the presence of an organometallic base to form compound IA.

4. The process as defined in claim 3 wherein the Grignard acylation reaction is carried out in the presence of $C_2H_5MgCl$, in an organic solvent, 2-CH$_3$THF and organic base,
wherein the Grignard acylation reaction is carried out at a temperature within the range from about −50 to about −40° C.,
where in compounds E, C and D, $R^2$ is CH$_3$O, $R^1$ is H and $R^3$ is H and
wherein the reaction of D and $D^a$ is carried out at a temperature within the range from about −5 to about 5° C.

5. A process for preparing compound IIA having the structure

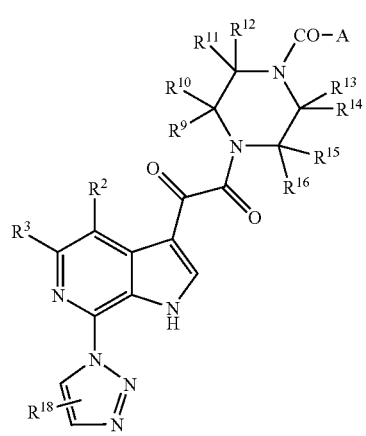

IIA wherein $R^{18}$ is H or alkyl, $R^1$, $R^2$ and $R^3$ are independently selected from the group consisting of hydrogen, halogen, cyano, nitro, COOR$^{56}$, XR$^{57}$, C(O)R$^7$, C(O)NR$^{55}$R$^{56}$, B, D, and E;

B is selected from the group consisting of —C(=NR$^{46}$)(R$^{47}$), C(O)NR$^{40}$R$^{41}$, aryl, heteroaryl, heteroalicyclic, S(O)$_2$R$^8$, C(O)R$^7$, XR$^{8a}$, (C$_{1-6}$)alkylNR$^{40}$R$^{41}$, (C$_{1-6}$)alkylCOOR$^{8b}$; wherein said aryl, heteroaryl, and heteroalicyclic are optionally substituted with one to three same or different halogens or from one to three same or different substituents selected from the group F; wherein aryl is naphthyl or substituted phenyl; wherein heteroaryl is a mono or bicyclic system which contains from 3 to 7 ring atoms for a mono cyclic system and up to 12 atoms in a fused bicyclic system, including from 1 to 4 heteroatoms; wherein heteroalicyclic is a 3 to 7 membered mono cyclic ring which may contain from 1 to 2 heteroatoms in the ring skeleton and which may be fused to a benzene or pyridine ring;

D is selected from the group consisting of (C$_{1-6}$)alkyl and (C$_{2-6}$)alkenyl; wherein said (C$_{1-6}$)alkyl and (C$_{2-6}$)alkenyl are optionally substituted with one to three same or different halogens or from one to three same or different substituents selected from the group consisting of C(O)NR$^{55}$R$^{56}$, hydroxy, cyano and XR$^{57}$;

E is selected from the group consisting of (C$_{1-6}$)alkyl and (C$_{2-6}$)alkenyl; wherein said (C$_{1-6}$)alkyl and (C$_{2-6}$)alkenyl are independently optionally substituted with a member selected from the group consisting of phenyl, heteroaryl, SMe, SPh, —C(O)NR$^{56}$R$^{57}$, C(O)R$^{57}$, SO$_2$(C$_{1-6}$)alkyl and SO$_2$Ph; wherein heteroaryl is a monocyclic system which contains from 3 to 7 ring atoms, including from 1 to 4 heteroatoms;

X is NH, NCH$_3$, O or S;

F is selected from the group consisting of $(C_{1-6})$alkyl, $(C_{3-7})$cycloalkyl, aryl, heteroaryl, heteroalicyclic, hydroxy, $(C_{1-6})$alkoxy, aryloxy, $(C_{1-6})$thioalkoxy, cyano, halogen, nitro, —C(O)R$^{57}$, benzyl, —NR$^{42}$C(O)—(C$_6$)alkyl, —NR$^{42}$C(O)—(C$_{3-6}$)cycloalkyl, —NR$^{42}$C(O)-aryl, —NR$^{42}$C(O)-heteroaryl, —NR$^{42}$C(O)-heteroalicyclic, a 4,5, or 6 membered ring cyclic N-lactam, —NR$^{42}$S(O)$_2$—(C$_{1-6}$)alkyl, —NR$^{42}$S(O)$_2$—(C$_{3-6}$)cycloalkyl, —NR$^{42}$S(O)2-aryl, —NR$^{42}$S(O)$_2$-heteroaryl, —NR$^{42}$S(O)2-heteroalicyclic, S(O)$_2$(C$_{1-6}$)alkyl, S(O)$_2$aryl, —S(O)$_2$NR$^{42}$R$^{43}$, NR$^{42}$R$^{43}$, (C$_{1-6}$)alkylC(O)NR$^{42}$R$^{43}$, C(O)N$^{42}$R$^{43}$, NHC(O)NR$^{42}$R$^{43}$, OC(O)NR$^{42}$R$^{43}$, NHC(O)OR$^{54}$, (C$_{1-6}$)alkylNR$^{42}$R$^{43}$, COOR$^{54}$, and (C$_{1-6}$)alkylCOOR$^{54}$; wherein said (C$_{1-6}$)alkyl, (C$_{3-7}$)cycloalkyl, aryl, heteroaryl, heteroalicyclic, (C$_{1-6}$)alkoxy, and aryloxy, are optionally substituted with one to nine same or different halogens or from one to five same or different substituents selected from the group G; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

G is selected from the group consisting of (C$_{1-6}$)alkyl, (C$_{3-7}$)cycloalkyl, aryl, heteroaryl, heteroalicyclic, hydroxy, (C$_{1-6}$)alkoxy, aryloxy, cyano, halogen, nitro, —C(O)R$^{57}$, benzyl, —NR$^{48}$C(O)—(C$_{1-6}$)alkyl, —NR$^{48}$C(O)—(C$_{3-6}$)cycloalkyl, —NR$^{48}$C(O)-aryl, —NR$^{48}$C(O)-heteroaryl, —NR$^{48}$C(O)-heteroalicyclic, a 4,5, or 6 membered ring cyclic N-lactam, —NR$^{48}$S(O)$_2$—(C$_{1-6}$)alkyl, —NR$^{48}$S(O)$_2$—(C$_{3-6}$)cycloalkyl, —NR$^{48}$S(O)2-aryl, —NR$^{48}$S(O)$_2$-heteroaryl, —NR$^{48}$S(O)2-heteroalicyclic, sulfinyl, sulfonyl, sulfonamide, NR$^{48}$R$^{49}$, (C$_{1-6}$)alkyl C(O)NR$^{48}$R$^{49}$, C(O)NR$^{48}$R$^{49}$, NHC(O)NR$^{48}$R$^{49}$, OC(O)NR$^{48}$R$^{49}$, NHC(O)OR$^{54}$, (C$_{1-6}$)alkylNR$^{48}$R$^{49}$, COOR$^{54}$, and (C$_{1-6}$)alkylCOOR$^{54}$; wherein aryl is phenyl; heteroaryl is a monocyclic system which contains from 3 to 7 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine;

R$^7$ is selected from the group consisting of aryl, heteroaryl, and heteroalicyclic; wherein said aryl, heteroaryl, and heteroalicyclic are optionally substituted with one to three same or different halogens or with from one to three same or different substituents selected from the group F; wherein for R$^7$, R$^8$, R$^{8a}$, R$^{8b}$ aryl is phenyl; heteroaryl is a mono or bicyclic system which contains from 3 to 7 ring atoms for mono cyclic systems and up to 10 atoms in a bicyclic system, including from 1 to 4 heteroatoms; wherein heteroalicyclic is selected from the group consisting of aziridine, azetidine, pyrrolidine, piperazine, piperidine, tetrahydrofuran, tetrahydropyran, azepine, and morpholine;

R$^8$ is selected from the group consisting of hydrogen, (C$_{1-6}$)alkyl, (C$_{3-7}$)cycloalkyl, (C$_{2-6}$)alkenyl, (C$_{3-7}$)cycloalkenyl, (C$_{2-6}$)alkynyl, aryl, heteroaryl, and heteroalicyclic; wherein said (C$_{1-6}$)alkyl, (C$_{3-7}$)cycloalkyl, (C$_{2-6}$)alkenyl, (C$_{3-7}$)cycloalkenyl, (C$_{2-6}$)alkynyl, aryl, heteroaryl, and heteroalicyclic are optionally substituted with one to six same or different halogens or from one to five same or different substituents selected from the group F;

R$^{8a}$ is a member selected from the group consisting of aryl, heteroaryl, and heteroalicyclic; wherein each member is independently optionally substituted with one to six same or different halogens or from one to five same or different substituents selected from the group F;

R$^{8b}$ is selected from the group consisting of hydrogen, (C$_{1-6}$)alkyl and phenyl;

R$^{40}$ and R$^{41}$ are independently selected from the group consisting of (a) hydrogen;

(b) (C$_{1-6}$)alkyl or (C$_{3-7}$)cycloalkyl substituted with one to three same or different halogens or from one to two same or different substituents selected from the group F; and (c) (C$_{1-6}$)alkoxy, aryl, heteroaryl or heteroalicyclic; or R$^{40}$ and R$^{41}$ taken together with the nitrogen to which they are attached form a member selected from the group consisting of aziridine, azetidine, pyrrolidine, piperazine, 4-NMe piperazine, piperidine, azepine, and morpholine; and wherein said aryl, heteroaryl, and heteroalicyclic are optionally substituted with one to three same or different halogens or from one to two same or different substituents selected from the group F; wherein for R$^{40}$ and R$^{41}$ aryl is phenyl; heteroaryl is a monocyclic system which contains from 3 to 6 ring atoms, including from 1 to 4 heteroatoms; heteroalicyclic is selected from the group consisting of aziridine, azetidine, pyrrolidine, piperazine, piperidine, tetrahydrofuran, tetrahydropyran, azepine, and morpholine; provided when B is C(O)NR$^{40}$R$^{41}$, at least one of R$^{40}$ and R$^{41}$ is not selected from groups (a) or (b);

R$^{42}$ and R$^{43}$ are independently selected from the group consisting of hydrogen, (C$_{1-6}$)alkyl, allyl, (C$_{1-6}$)alkoxy, (C$_{3-7}$)cycloalkyl, aryl, heteroaryl and heteroalicyclic; or R$^{42}$ and R$^{43}$ taken together with the nitrogen to which they are attached form a member selected from the group consisting of aziridine, azetidine, pyrrolidine, piperazine, 4-NMe piperazine, piperidine, azepine, and morpholine; and wherein said (C$_{1-6}$)alkyl, (C$_{1-6}$)alkoxy, (C$_{3-7}$)cycloalkyl, aryl, heteroaryl, and heteroalicyclic are optionally substituted with one to three same or different halogens or from one to two same or different substituents selected from the group G; wherein for R$^{42}$ and R$^{43}$ aryl is phenyl; heteroaryl is a monocyclic system which contains from 3 to 6 ring atoms, including from 1 to 4 heteroatoms; heteroalicyclic is a member selected from the group consisting of aziridine, azetidine, pyrrolidine, piperazine, piperidine, tetrahydrofuran, tetrahydropyran, azepine, and morpholine;

R$^{46}$ is selected from the group consisting of H, OR$^{57}$, and NR$^{55}$R$^{56}$;

R$^{47}$ is selected from the group consisting of H, amino, halogen, phenyl, and (C$_{1-6}$)alkyl;

R$^{48}$ and R$^{49}$ are independently selected from the group consisting of hydrogen, (C$^{1-6}$)alkyl and phenyl;

R$^{54}$ is selected from the group consisting of hydrogen and (C$_{1-6}$)alkyl;

R$^{56}$ is independently selected from the group consisting of hydrogen and (C$_{1-6}$)alkyl; and R$^{57}$ is selected from the group consisting of hydrogen, (C$_{1-6}$)alkyl and phenyl, where A is selected from the group consisting of C$_{1-6}$alkoxy, aryl and heteroaryl; in which said aryl is phenyl or naphthyl; said heteroaryl is selected from the group consisting of pyridinyl, pyrimidinyl, pyrazinyl, triazinyl, ftzranyl, thienyl, pyrrolyl, imidazolyl, thiazolyl, isothiazolyl, oxazolyl, isoxazolyl, quinolinyl, isoquinolinyl, benzofuranyl, benzothienyl, benzoimidazolyl and benzothiazolyl; and said aryl or heteroaryl is optionally substituted with one or two of the same or different members selected from the group consisting of amino, nitro, cyano, hydroxy, $C_{1-6}$alkoxy, —C(O)NH$_2$, $C_{1-6}$alkyl, —NHC(O)CH$_3$, halogen and trifluoromethyl; and $R^9$, $R^{10}$, $R^{11}$, $R^{12}$, $R^{13}$, $R^{14}$, $R^{15}$ and $R^{16}$ are each independently H or ($C_{1-6}$)alkyl which may be optionally substituted with 1 to 3 same or different halogens; which comprises subjecting compound H as defined in claim 1 of the structure

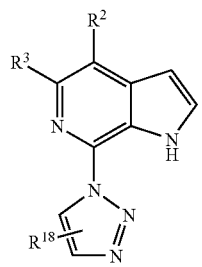

to a Grignard acylation reaction wherein acid chloride 1

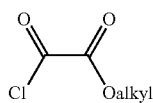

is reacted with compound H to form compound L

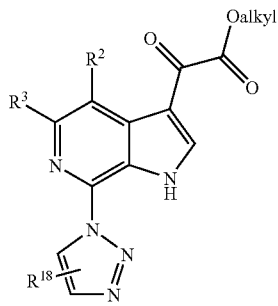

and reacting compound L with a compound $D^a$ of the structure

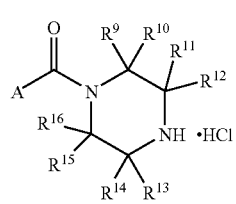

in the presence of an organometallic base to form compound IIA.

6. The process as defined in claim 5 wherein the Grignard acylation reaction is carried out in the presence of $C_2H_5MgCl$ in an organic solvent, 2-CH$_3$THF and organic base, wherein the Grignard acylation reaction is carried out at a temperature within the range from about −40 to about −50° C., where in compounds IIA, L and H, $R^2$ is F, and $R^3$ is H and wherein the reaction of compound L and compound $D^a$ is carried out at a temperature within the range from about −5 to about 5° C.

7. A pharmaceutical formulation in the form of an aqueous oral suspension comprising:

a) the crystalline form of the 1,2,3-triazine derivative IIA having the structure

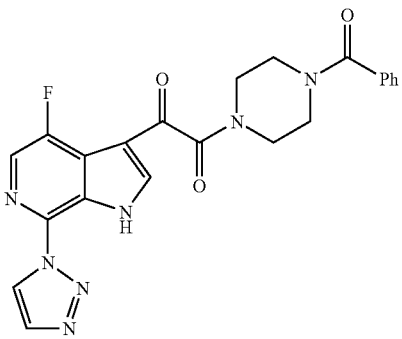

b) 6.25% w/v Microcrystalline Cellulose;
c) 0.0001% w/v Denatonium Benzoate; and
d) Purified Water, or Water for Injection; wherein said crystalline form is the N-1 form of the free base, and is characterized by one or more of the following:

a) unit cell parameters substantially equal to the following:
Cell Dimensions:
a=39.2481(14) Å
b=5.5577(2) Å
c=21.8072(10) Å
α=90°
β=122.399(4) °
γ=90°
Space group C2/c
wherein said crystalline form is at about 25° C.;

b) fractional atomic coordinates substantially as listed in Table 2;
c) a powder X-ray diffraction pattern substantially in accordance with that shown in FIG. 5;
d) a powder X-ray diffraction pattern comprising the following typical and representative 2θ values (CuKα λ=1.5418 Å) 5.3±0.1, 8.1+0.1, 9.6±0.1, 16.2±0.1, 17.0±0.1, 19.6±0.1, 20.7±0.1 and 23.0±0.1 at about room temperature;
e) a differential scanning calorimetry thermogram substantially in accordance with that shown in FIG. 6;
f) a thermal gravimetric analysis curve substantially in accordance with that shown in FIG. 7; and/or
g) a moisture-sorption isotherm substantially as shown in FIG. 8.

8. A process for preparing a stabilized amorphous form of a 1,2,3-triazole derivative IIA having the structure

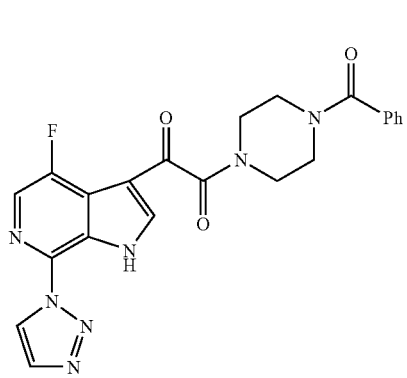

which comprises flash evaporating or spray drying a solution of the crystalline Form N-1 of the 1,2,3-triazole derivative and a stabilizer in an organic solvent and recovering the stabilized amorphous form of the 1,2,3-triazole derivative II; wherein said crystalline Form N-1 is characterized by one or more of the following:

a) unit cell parameters substantially equal to the following:
Cell Dimensions:
a=39.2481(14) Å
b=5.5577(2) Å
c=21.8072(10) Å
α=90°
β=122.399(4)°
γ=90°
Space group C2/c
wherein said crystalline form is at about 25° C.;

b) fractional atomic coordinates substantially as listed in Table 2;

c) a powder X-ray diffraction pattern substantially in accordance with that shown in FIG. 5;

d) a powder X-ray diffraction pattern comprising the following typical and representative 2θ values (CuKα λ=1.5418 Å) 5.3±0.1, 8.1+0.1, 9.6±0.1, 16.2±0.1, 17.0±0.1, 19.6±0.1, 20.7±0.1 and 23.0±0.1 at about room temperature;

e) a differential scanning calorimetry thermogram substantially in accordance with that shown in FIG. 6;

f) a thermal gravimetric analysis curve substantially in accordance with that shown in FIG. 7; and/or g) a moisture-sorption isotherm substantially as shown in FIG. 8.

9. The process as defined in claim 8 wherein the stabilizer is polyvinylpyrrolidone, polyvinylpyrrolidone-vinyl acetate copolymer, or polyvinylpyrrolidone-vinyl acetate copolymer and d-α-tocopheryl polyethylene glycol 1000 succinate.

10. A pharmaceutical formulation in the form of an oral solution comprising
a) the crystalline form of the 1,2,3-triazole derivative IIA having the structure;

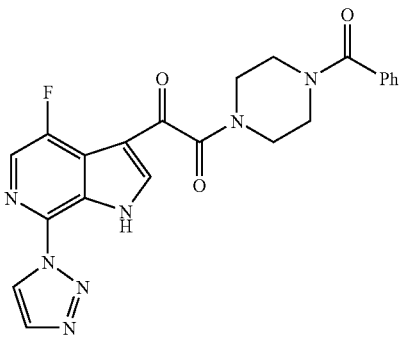

and
b) a vehicle comprising
1) 75% (w/w) polyethylene glycol 400;
2) 10% (w/w) d-alpha tocopheryl polyethylene glycol 1000-succinate; and
3) 15% (w/w) ethyl alcohol; wherein said crystalline form is the N-1 form of the free base, and is characterized by one or more of the following:

a) unit cell parameters substantially equal to the following:
Cell Dimensions:
a=39.2481(14) Å
b=5.5577(2) Å
c=21.8072(10) Å
α=90°
β=122.399(4)°
γ=90°
Space group C2/c
wherein said crystalline form is at about 25° C.;

b) fractional atomic coordinates substantially as listed in Table 2;

c) a powder X-ray diffraction pattern substantially in accordance with that shown in FIG. 5;

d) a powder X-ray diffraction pattern comprising the following typical and representative 2θ values (CuKα λ=1.5418 Å) 5.3±0.1, 8.1+0.1, 9.6±0.1, 16.2±0.1, 17.0±0.1, 19.6±0.1, 20.7±0.1 and 23.0±0.1 at about room temperature;

e) a differential scanning calorimetry thermogram substantially in accordance with that shown in FIG. 6;

f) a thermal gravimetric analysis curve substantially in accordance with that shown in FIG. 7; and/or g) a moisture-sorption isotherm substantially as shown in FIG. 8.

11. A pharmaceutical formulation comprising the 1,2,3-triazole derivative II prepared as defined in claim 8 in the form of a spray-dried intermediate, a filler, a disintegrant, a dissolution enhancer and a lubricant.

12. A process for preparing the N-1 crystalline form of the 1,2,3-triazole derivative IIA of the structure II

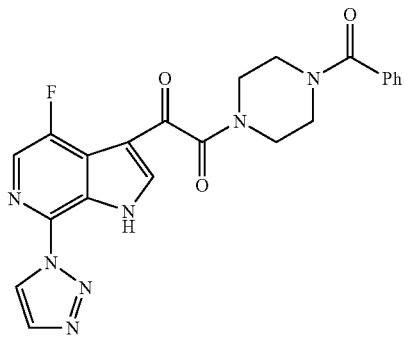

as defined in claim 7, which comprises dissolving or slurrying or suspending the 1,2,3-triazole derivative IIA in an aqueous organic solvent or organic solvent to form a solution, slurry or suspension of the 1,2,3-triazole derivative II, removing the solvent and recovering the 1,2,3-triazole derivative II in the form of Form N-1 crystals, wherein the solvent employed is water/ethanol, acetonitrile, acetonitrile/methanol, dichloromethane, methanol, ethanol, and/or isopropyl alcohol.

* * * * *

UNITED STATES PATENT AND TRADEMARK OFFICE
CERTIFICATE OF CORRECTION

PATENT NO. : 7,601,715 B2 Page 1 of 1
APPLICATION NO. : 11/455338
DATED : October 13, 2009
INVENTOR(S) : Soundararajan et al.

It is certified that error appears in the above-identified patent and that said Letters Patent is hereby corrected as shown below:

Claim 2, delete the text "as defined in claim 1" appearing in col. 77, lines 18 to 19 and line 37.

Claim 3, delete the text "as defined in claim 1" appearing in col. 81, lines 12 to 13.

Signed and Sealed this

Tenth Day of August, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,601,715 B2 | |
| APPLICATION NO. | : 11/455338 | |
| DATED | : October 13, 2009 | |
| INVENTOR(S) | : Nachimuthu Soundararajan et al. | |

It is certified that error appears in the above-identified patent and that said Letters Patent is hereby corrected as shown below:

On the Title Page:

Item (56), References Cited, under OTHER PUBLICATIONS:

Column 2, J.E. Francis et al. reference, change "disubsituted" to -- disubstituted --.

The reference should read:

-- J.E. Francis et al., "A convenient synthesis of 3,5-disubstituted-1,2,4-triazoles", Tetrahedron Letters vol. 28, No. 43, 1987, pp. 5133-5136. --.

Item (57), ABSTRACT: ,

Column 2, line 1 and 2, change "azaindoloxoacetic" to -- azaindoleoxoacetic --.

In the Claims:

Claim 1:

Column 77, line 16, change "where in" to -- wherein --.

Claim 2:

Column 78, line 16, change "where in" to -- wherein --.

Claim 3:

Column 78, line 62, after "NCH$_3$", insert -- , --.

Signed and Sealed this
First Day of November, 2011

David J. Kappos
*Director of the United States Patent and Trademark Office*

CERTIFICATE OF CORRECTION (continued)
U.S. Pat. No. 7,601,715 B2

In the Claims:

Claim 3 (continued):

Column 79, line 13, change "—$NR^{42}S(O)2$-aryl" to -- —$NR^{42}S(O)_2$-aryl --.

Column 79, line 14, change "—$NR^{42}S(O)2$-heteroalicyclic" to -- —$NR^{42}S(O)_2$-heteroalicyclic --.

Column 79, line 15, change "—$S(O)2NR^{42}R^{43}$" to -- —$S(O)_2NR^{42}R^{43}$ --.

Column 79, line 38, change "—$NR^{48}S(O)2$-aryl" to -- —$NR^{48}S(O)_2$-aryl --.

Column 79, lines 38 and 39, change "—$NR^{48}S(O)2$-heteroalicyclic" to -- —$NR^{48}S(O)_2$-heteroalicyclic --.

Column 79, line 40, change "$(C_{1-6})$alkyl $C(O)NR^{48}R^{49}$" to -- $(C_{1-6})$alkyl$C(O)NR^{48}R^{49}$ --.

Column 79, line 41, change "$NHC(O)OR^{54}$'" to -- "$NHC(O)OR^{54}$ --.

Column 80, line 42, before "heteroaryl", insert -- aryl, --.

Claim 4:

Column 82, line 10, change "where in" to -- wherein --.

Claim 5:

Column 83, line 9, change "$(C_6)$alkyl" to -- $(C_{1-6})$alkyl --.

Column 83, line 11, change "4,5" to -- 4, 5 --.

Column 83, line 13, change "—$NR^{42}S(O)2$-aryl" to -- —$NR^{42}S(O)_2$-aryl --.

Column 83, line 14, change "—$NR^{42}S(O)2$-heteroalicyclic" to -- —$NR^{42}S(O)_2$-heteroalicyclic --.

Column 83, line 16, change "$C(O)N^{42}R^{43}$" to -- $C(O)NR^{42}R^{43}$ --.

Column 83, line 36, change "4,5" to -- 4, 5 --.

Column 83, line 38, change "—$NR^{48}S(O)2$-aryl" to -- —$NR^{48}S(O)_2$-aryl --.

Column 83, lines 38 and 39, change "—$NR^{48}S(O)2$-heteroalicyclic" to -- —$NR^{48}S(O)_2$-heteroalicyclic --.

CERTIFICATE OF CORRECTION (continued)
U.S. Pat. No. 7,601,715 B2

In the Claims:
Claim 5 (continued):

Column 83, line 40, change "$(C_{1-6})$alkyl C(O)NR$^{48}$R$^{49}$" to -- $(C_{1-6})$alkylC(O)NR$^{48}$R$^{49}$ --.

Column 83, line 41, change "NHC(O)OR$^{54}$'" to -- "NHC(O)OR$^{54}$ --.

Column 84, line 57, change "(C$^{1-6}$)alkyl" to -- $(C_{1-6})$alkyl --.

Column 84, line 67, change "ftzranyl" to -- "furanyl --.

Column 86, line 8, change "where in" to -- "wherein --.